United States Patent [19]
Bergeron et al.

[11] Patent Number: 6,001,564
[45] Date of Patent: Dec. 14, 1999

[54] SPECIES SPECIFIC AND UNIVERSAL DNA PROBES AND AMPLIFICATION PRIMERS TO RAPIDLY DETECT AND IDENTIFY COMMON BACTERIAL PATHOGENS AND ASSOCIATED ANTIBIOTIC RESISTANCE GENES FROM CLINICAL SPECIMENS FOR ROUTINE DIAGNOSIS IN MICROBIOLOGY LABORATORIES

[75] Inventors: Michel G. Bergeron, Sillery; Marc Ouellette, Québec; Paul H. Roy, Loretteville, all of Canada

[73] Assignee: Infectio Diagnostic, Inc., Canada

[21] Appl. No.: 08/526,840

[22] Filed: Sep. 11, 1995

Related U.S. Application Data

[63] Continuation-in-part of application No. 08/304,732, Sep. 12, 1994.

[51] Int. Cl.⁶ .............................. C12Q 1/68; C12P 19/34
[52] U.S. Cl. ............................................. 435/6; 435/91.2
[58] Field of Search ........................ 435/6, 91.2; 536/22.1

[56] References Cited

U.S. PATENT DOCUMENTS

| | | | |
|---|---|---|---|
| 4,816,389 | 3/1989 | Sansonnetti et al. | 435/6 |
| 5,030,556 | 7/1991 | Beaulieu et al. | 435/6 |
| 5,041,372 | 8/1991 | Lampel et al. | 435/6 |
| 5,084,565 | 1/1992 | Parodos et al. | 536/27 |
| 5,232,831 | 8/1993 | Milliman et al. | 435/6 |
| 5,292,874 | 3/1994 | Milliman | 536/24 |
| 5,298,392 | 3/1994 | Atlas et al. | 435/600 |
| 5,334,501 | 8/1994 | Adams et al. | 435/6 |
| 5,401,631 | 3/1995 | Lane et al. | 435/6 |
| 5,437,978 | 8/1995 | Ubukata et al. | 435/6 |
| 5,472,843 | 12/1995 | Milliman | 435/6 |

FOREIGN PATENT DOCUMENTS

| | | | |
|---|---|---|---|
| 2052822 | 4/1992 | Canada | C12Q 1/68 |
| 0272009 | 6/1988 | European Pat. Off. . | |
| 0277237 | 8/1988 | European Pat. Off. . | |
| 0297291 | 1/1989 | European Pat. Off. . | |
| 0 438 115 | 7/1991 | European Pat. Off. . | |
| 0527628 | 2/1993 | European Pat. Off. . | |
| 0577523 | 1/1994 | European Pat. Off. . | |
| 0652291 | 5/1995 | European Pat. Off. . | |
| 0695803 | 2/1996 | European Pat. Off. . | |
| 2 584 419 | 1/1987 | France . | |
| 2584419 | 1/1987 | France | C12N 15/00 |
| 2 599 743 | 12/1987 | France . | |
| 2599743 | 12/1987 | France | C12N 15/00 |
| 2636075 | 3/1990 | France | C12Q 1/68 |
| 2685334 | 6/1993 | France | C07K 7/10 |
| 2 699 539 | 6/1994 | France . | |
| 2699539 | 6/1994 | France . | |
| 6-54700 | 3/1994 | Japan . | |
| 6-90798 | 4/1994 | Japan . | |
| 6-165681 | 6/1994 | Japan . | |
| 7-67657 | 3/1995 | Japan . | |
| 7-209294 | 8/1995 | Japan . | |
| 90/14444 | 11/1990 | WIPO . | |
| 91/08 305 | 6/1991 | WIPO . | |
| 91/08305 | 6/1991 | WIPO . | |
| 91/11531 | 8/1991 | WIPO . | |
| 91/16454 | 10/1991 | WIPO . | |
| 91/18926 | 12/1991 | WIPO . | |
| 92/14488 | 9/1992 | WIPO . | |
| 93/03 186 | 2/1993 | WIPO . | |
| 93/03186 | 2/1993 | WIPO . | |
| 94/02 645 | 2/1994 | WIPO . | |
| 95/00650 | 1/1995 | WIPO . | |
| 95/09025 | 4/1995 | WIPO . | |
| 95/20055 | 7/1995 | WIPO . | |
| 96/00298 | 1/1996 | WIPO . | |
| 96/02648 | 2/1996 | WIPO . | |

OTHER PUBLICATIONS

Johnson and Stamm. (1989). Ann. Intern. Med. 111: 906–917.
Koening et al. (1992). J. Clin. Microbiol. 30(2): 342–345.
Pezzlo. (1988). Clin. Microbiol. Rev. 1(2): 268–280.
Pezzlo et al. (1992). J. Clin. Microbiol. 30: 680–684.
Sanger et al. (1977). P.N.A.S. 74(12): 5463–5467.
Stark and Maki. (1984). N. Engl. J. Med. 311: 560–564.
Tenover and Unger. (1993). in Persing et al. *Diagnostic Molecular Microbiology: Principles and Applications*. pp. 3–25.
York et al. (1992). J. Clin. Microbiol. 30(11): 2903–2910.

*Primary Examiner*—Eggerton A. Campbell
*Attorney, Agent, or Firm*—Quarles & Brady LLP

[57] ABSTRACT

The present invention relates to DNA-based methods for universal bacterial detection, for specific detection of the common bacterial pathogens *Escherichia coli, Klebsiella pneumoniae, Pseudomonas aeruginosa, Proteus mirabilis, Streptococcus pneumoniae, Staphylococcus aureus, Staphylococcus epidermidis, Enterococcus faecalis, Staphylococcus saprophyticus, Streptococcus pyogenes, Haemophilus influenzae* and *Moraxella catarrhalis* as well as for specific detection of commonly encountered and clinically relevant bacterial antibiotic resistance genes directly from clinical specimens or, alternatively, from a bacterial colony. The above bacterial species can account for as much as 80% of bacterial pathogens isolated in routine microbiology laboratories.

78 Claims, No Drawings

SEQUENCE LISTING (1) GENERAL INFORMATION:

(iii) NUMBER OF SEQUENCES: 177

(2) INFORMATION FOR SEQ ID NO:1:

(i) SEQUENCE CHARACTERISTICS:
      (A) LENGTH: 1817 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Enterococcus faecalis (xi) SEQUENCE DESCRIPTION: SEQ ID NO:1:

```
ACAGTAAAAA AGTTGTTAAC GAATGAATTT GTTAACAACT TTTTTGCTAT GGTATTGAGT        60
TATGAGGGGC AATACAGGGA AAAATGTCGG CTGATTAAGG AATTTAGATA GTGCCGGTTA       120
GTAGTTGTCT ATAATGAAAA TAGCAACAAA TATTTACGCA GGGAAAGGGG CGGTCGTTTA       180
ACGGAAAAAA TTAGGGAGGA TAAAGCAATA CTTTTGTTGG GAAAGAAAT AAAAGGAAAC        240
TGGGGAAGGA GTTAATTGTT TGATGAAGGG AAATAAAATT TTATACATTT TAGGTACAGG      300
CATCTTTGTT GGAAGTTCAT GTCTATTTTC TTCACTTTTT GTAGCCGCAG AAGAACAAGT      360
TTATTCAGAA AGTGAAGTTT CAACAGTTTT ATCGAAGTTG GAAAAGGAGG CAATTTCTGA      420
GGCAGCTGCT GAACAATATA CGGTTGTAGA TCGAAAAGAA GACGCGTGGG GGATGAAGCA      480
TCTTAAGTTA GAAAAGCAAA CGGAAGGCGT TACTGTTGAT TCAGATAATG TGATTATTCA      540
TTTAGATAAA AACGGTGCAG TAACAAGTGT TACAGGAAAT CCAGTTGATC AAGTTGTGAA      600
AATTCAATCG GTTGATGCAA TCGGTGAAGA AGGAGTTAAA AAAATTGTTG CTTCTGATAA      660
TCCAGAAACT AAAGATCTTG TCTTTTTAGC TATTGACAAA CGTGTAAATA ATGAAGGGCA      720
ATTATTTTAT AAAGTCAGAG TAACTTCTTC ACCAACTGGT GACCCCGTAT CATTGGTTTA      780
TAAAGTGAAC GCTACAGATG GAACAATTAT GGAAAAACAA GATTTAACGG AACATGTCGG      840
TAGTGAAGTA ACGTTAAAAA ACTCTTTTCA AGTAACGTTT AATGTACCAG TTGAAAAAAG      900
CAATACGGGA ATTGCTTTAC ACGGAACGGA TAACACAGGG GTTTACCATG CAGTAGTTGA      960
TGGCAAAAAT AATTATTCTA TTATTCAAGC GCCATCACTA GCGACATTAA ATCAGAATGC     1020
TATTGACGCC TATACGCATG GAAAATTTGT GAAAACATAT TATGAAGATC ATTTCCAACG     1080
ACACAGTATT GATGATCGAG GGATGCCCAT CTTGTCAGTT GTTGATGAAC AACATCCAGA     1140
TGCTTATGAC AATGCTTTTT GGGATGGAAA AGCAATGCGT TATGGTGAAA CAAGTACACC     1200
AACAGGAAAA ACGTATGCTT CCTCTTTAGA TGTAGTTGGT CATGAAATGA CACATGGTGT     1260
GACGGAACAT ACTGCCGGTT TAGAATATTT AGGACAATCA GGTGCCTTGA ATGAATCTTA     1320
```

```
TTCTGATTTG ATGGGTTATA TTATTTCGGG TGCATCTAAT CCAGAAATTG GTGCGGATAC    1380

TCAGAGTGTT GACCGAAAAA CAGGTATTCG AAATTTACAA ACGCCAAGTA AACACGGACA    1440

ACCAGAAACC ATGGCTCAAT ACGACGATCG AGCACGGTAT AAAGGAACGC CTTATTATGA    1500

TCAAGGCGGT GTTCATTATA ACAGTGGAAT TATTAATCGG ATTGGTTACA CCATTATCCA    1560

GAACTTAGGC ATTGAAAAAG CACAGACTAT TTTCTACAGC TCGTTAGTAA ATTACTTAAC    1620

ACCTAAAGCA CAATTCAGTG ATGCTCGTGA TGCGATGCTT GCTGCTGCAA AAGTTCAATA    1680

TGGCGATGAA GCAGCTTCAG TGGTGTCAGC AGCCTTTAAC TCTGCTGGAA TCGGAGCTAA    1740

AGAAGACATT CAGGTAAACC AACCAAGTGA ATCTGTTCTG GTCAATGAAT GAAAAAAATT    1800

CCCCAATTAA ATAAAAA                                                   1817

(2) INFORMATION FOR SEQ ID NO:2:

(i) SEQUENCE CHARACTERISTICS:
        (A) LENGTH: 2275 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Enterococcus faecalis (xi) SEQUENCE DESCRIPTION: SEQ ID NO:2:

GGTACCAAAG AAAAAAACGA ACGCCACAAC CAACAGCCTC TAAAGCAACA CCTGCTTCTG      60

AAATTGAGGG AGATTTAGCA ATGTCAATG AGATTCTTTT GGTTCACGAT GATCGTGTCG     120

GGTCAGCAAC GATGGGAATG AAAGTCTTAG AAGAAATTTT AGATAAAGAG AAATTTCAA     180

TGCCGATTCG AAAAATTAAT ATTAATGAAT TAACTCAACA ACACAGGCT TTAATTGTCA     240

CAAAAGCTGA ACTAACGGAA CAAGCACGTA AAAAGCACC GAAAGCGACA CACTTATCAG     300

TAAAAAGTTA TGGTTAATCC CCAAAAATAT GAAACAGTGG GTTTCGCTCT TAAAAGAAAG   360

TGCCTAGAGA GGAAGAAAAC AATGGAAAAT CTTACGAATA TTTCAATTGA ATTAAATCAA   420

CAGTTTAATA CAAAAGAAGA AGCTATTCGC TTTTCCGGCC AGAAACTAGT CGAGGCAGGC   480

TGTGTTGAGC CCGCTTATAT CGAAGCAATG ATTGAAAGAG ACCAATTGCT ATCTGCCCAT   540

ATGGGGAATT TTATTGCCAT TCCTCATGGA ACAGAAGAAG CCAAAAAATT AGTGAAAAAA   600

TCAGGAATCT GTGTAGTGCA AGTCCCAGAG GGCGTTAATT TTGGCACCGA AGAAGATGAA   660

AAAATTGCTA CCGTATTATT TGGGATTGCC GGAGTCGGTG AAGAACATTT GCAATTAGTC   720

CAACAAATTG CACTTTATTG TAGTGATATG GATAACGTGG TGCAACTTGC CGATGCATTA   780

AGTAAAGAAG AAATAACAGA AAATTTAGCC ATTGCTTAAA GGAGAGAATA AGAATGAACG   840

CAGTACATTT TGGAGCAGGA AATATTGGAC GCGGCTTTAT TGGCGAAATT TTAGCTAAAA   900

CGGGTTTCAT ATTACCGTTT GTGGATGTTA ATGGAAACCA TCATCAAGCG TTAAAAGAAC   960

GTAAAAGTTA TACAATTGAA TTGGCCGATG CCTCACATCA ACAAATTAAC GTTGAAAATG  1020

TGACCGGGTT AAATAACATG ACAGAACCAG AAAAAGTAGT AGAAGCAATT GCGGAAGCCG  1080

ATTTAGTCAC GACGGCAATT GGTCCTAATA TTTTACCAAG AATTGCTGAA TTAATTGCTC  1140

AAGGAATTGA TGCACGTGCC GAAGCAAATT GTCAAAACGG CCCGCTGGAT ATTATCGCTT  1200

GTGAAAATAT GATTGGTGGT TCAACCTTTT TAGCAGAAGA AGTGGCCATA ATATTTGAAA  1260

AACCCAGCTT ATCTGAACAA TGGATTGGTT TTCCTGATGC GGCAGTTGAT CGGATTGTTC  1320

CATTACAAAA ACATAAAGAT CCACTTTTTG TTCAAGTTGA GCCTTTTTGT GAATGGGTCA  1380
```

```
TTGATGATAC CAACCGAAAA GCCAAAGAGA TTCAGTTAGA AGGCGTCATT ACTTGTCGAT      1440

TAGAGCCGTA TATTGAACGA AAATTATTTA GTGTAACCAG TGGCCATGCT ACAGTTGCCT      1500

ATACAGGGGC GTTGTTAGGC TATCAAACCA TTGACGAAGC GATGCAGGAC GCCTTAGTGG      1560

TAGCGCAACT CAAATCAGTT TTGCAGGAAA CCGGTAAACT TTTAGTGGCC AAATGGAATT      1620

TTGATGAACA AGAACATGCA GCCTATATTG AAAAAATTAT CAACCGTTTC CAAAATAAAT      1680

ATATTTCAGA TGCTATTACA CGTGTAGCAC GGACACCAAT CAGAAAATTA GGTGCGCAAG      1740

AACGGTTTAT TCGACCAATC CGTGAATTAC AGGAACGCAA TCTAGTGTCG GCCGCATTTA      1800

TAGCAATGAT TGGTATTGTC TTTAATTATC ATGATCCAGA AGATGAACAA AGCCGTCAAT      1860

TACAGGAAAT GCTTGACCAA GAAAGTGTTG ATACAGTGGA TCGCTGAAGT AACGGGCATT      1920

GAAGATCCAG AAACGGTTAA AAATATTAAA CAAAACGTAG AACTGCTATG CGCGACCACA      1980

AGTAGCATAA TTAACAAAAT CCTTCTACCA AGATACTTCA CATTTCTTAA TTAAAGAAAA      2040

AACAACCGCG CCTCACCTGA GCCGACCCCC AAAAGTTAGA CCTAGAAATC TAACTTTTGG      2100

AGGTTTTTTT GTATGGCAAA ATACAGTTTT GAAATTTAAA CTTAAACTTG TTCATGACTA      2160

CTTATATGGT CAAGGAGGTC TAAGGTTTCT CGCAAAGAAG TATGGGTTTA AAGATAGTCT      2220

CAAATAAGCA AATGGATAAA TGCCTATAAA GAACTTGGTG AAGAAGGGGG GATCC          2275

(2) INFORMATION FOR SEQ ID NO:3:

(i) SEQUENCE CHARACTERISTICS:
        (A) LENGTH: 227 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:3:

GATCCGCCAT GGGTTGTTTT CCGATTGAGG ATTTTATAGA TGGTTTCTGG CGACCTGCAC        60

AGGAGTACGG TGATTTTTAA TTATTGCAAT TGCACAAGAG TCAGTTCTCC CCCAAAGACA       120

GCACCGGTAT CAATATAATG CAGGTTGCCA ATATCCACGC GATGGCGCAA AGGTGTATGA       180

CCAAACCAGA AATGATCGGC CACCTGCATC GCCAGTTCGC GAGTCGG                    227

(2) INFORMATION FOR SEQ ID NO:4:

(i) SEQUENCE CHARACTERISTICS:
        (A) LENGTH: 278 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:4:

GATCTAAATC AAATTAATTG GTTAAAGATA ACCACAGCGG GGCCGACATA AACTCTGACA        60

AGAAGTTAAC AACCATATAA CCTGCACAGG ACGCGAACAT GTCTTCTCAT CCGTATGTCA       120

CCCAGCAAAA TACCCCGCTG GCGGACGACA CCACTCTGAT GTCCACTACC GATCTCGCTT       180

TCCAGCGTCA TATTGGGGCG CGCTACGTTG GGCGTGGGC GTAATTGGTC AATCAGGCGC        240

GGGGTCAGCG GATAAACATT CACCATTTTG TCGAGATC                              278
```

(2) INFORMATION FOR SEQ ID NO:5:

(i) SEQUENCE CHARACTERISTICS:
        (A) LENGTH: 1596 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:5:

```
ATGGCTGACA TTCTGCTGCT CGATAATATC GACTCTTTTA CGTACAACCT GGCAGATCAG        60

TTGCGCAGCA ATGGGCATAA CGTGGTGATT TACCGCAACC ATATACCGGC GCAAACCTTA       120

ATTGAACGCT TGGCGACCAT GAGTAATCCG GTGCTGATGC TTTCTCCTGG CCCCGGTGTG       180

CCGAGCGAAG CCGGTTGTAT GCCGGAACTC CTCACCCGCT TGCGTGGCAA GCTGCCCATT       240

ATTGGCATTT GCCTCGGACA TCAGGCGATT GTCGAAGCTT ACGGGGGCTA TGTCGGTCAG       300

GCGGGCGAAA TTCTCCACGG TAAAGCCTCC AGCATTGAAC ATGACGGTCA GGCGATGTTT       360

GCCGGATTAA CAAACCCGCT GCCGGTGGCG CGTTATCACT CGCTGGTTGG CAGTAACATT       420

CCGGCCGGTT TAACCATCAA CGCCCATTTT AATGGCATGG TGATGGCAGT ACGTCACGAT       480

GCGGATCGCG TTTGTGGATT CCAGTTCCAT CCGGAATCCA TTCTCACCAC CCAGGGCGCT       540

CGCCTGCTGG AACAAACGCT GGCCTGGGCG CAGCATAAAC TAGAGCCAGC CAACACGCTG       600

CAACCGATTC TGGAAAAACT GTATCAGGCG CAGACGCTTA GCCAACAAGA AAGCCACCAG       660

CTGTTTTCAG CGGTGGTGCG TGGCGAGCTG AAGCCGGAAC AACTGGCGGC GGCGCTGGTG       720

AGCATGAAAA TTCGCGGTGA GCACCCGAAC GAGATCGCCG GGGCAGCAAC CGCGCTACTG       780

GAAAACGCAG CGCCGTTCCC GCGCCCGGAT TATCTGTTTG CTGATATCGT CGGTACTGGC       840

GGTGACGGCA GCAACAGTAT CAATATTTCT ACCGCCAGTG CGTTTGTCGC CGCGGCCTGT       900

GGGCTGAAAG TGGCGAAACA CGGCAACCGT AGCGTCTCCA GTAAATCTGG TTCGTCCGAT       960

CTGCTGGCGG CGTTCGGTAT TAATCTTGAT ATGAACGCCG ATAAATCGCG CCAGGCGCTG      1020

GATGAGTTAG GTGTATGTTT CCTCTTTGCG CCGAAGTATC ACACCGGATT CCGCCACGCG      1080

ATGCCGGTTC GCCAGCAACT GAAAACCCGC ACCCTGTTCA ATGTGCTGGG GCCATTGATT      1140

AACCCGGCGC ATCCGCCGCT GGCGTTAATT GGTGTTTATA GTCCGGAACT GGTGCTGCCG      1200

ATTGCCGAAA CCTTGCGCGT GCTGGGGTAT CAACGCGCGG CGGTGGTGCA CAGCGGCGGG      1260

ATGGATGAAG TTTCATTACA CGCGCCGACA ATCGTTGCCG AACTGCATGA CGGCGAAATT      1320

AAAAGCTATC AGCTCACCGC AGAAGACTTT GGCCTGACAC CCTACCACCA GGAGCAACTG      1380

GCAGGCGGAA CACCGGAAGA AAACCGTGAC ATTTTAACAC GTTTGTTACA AGGTAAAGGC      1440

GACGCCGCCC ATGAAGCAGC CGTCGCTGCG AACGTCGCCA TGTTAATGCG CCTGCATGGC      1500

CATGAAGATC TGCAAGCCAA TGCGCAAACC GTTCTTGAGG TACTGCGCAG TGGTTCCGCT      1560

TACGACAGAG TCACCGCACT GGCGGCACGA GGGTAA                                1596
```

(2) INFORMATION FOR SEQ ID NO:6:

(i) SEQUENCE CHARACTERISTICS:
        (A) LENGTH: 2703 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
    (A) ORGANISM: Escherichia coli (xi) SEQUENCE DESCRIPTION: SEQ ID NO:6:

| | | | | | |
|---|---|---|---|---|---|
| GACGACTTAG | TTTTGACGGA | ATCAGCATAG | TTAATCACTT | CACTGTGGAA | AATGAGGAAA | 60
| TATTATTTTT | TTTGCGCTTC | GTAATTAATG | GTTATAAGGT | CGGCCAGAAA | CCTTTCTAAT | 120
| GCAAGCGATG | ACGTTTTTTT | ATGTGTCTGA | ATTTGCACTG | TGTCACAATT | CCAAATCTTT | 180
| ATTAACAACT | CACCTAAAAC | GACGCTGATC | CAGCGTGAAT | ACTGGTTTCC | CTTATGTTCA | 240
| TCAGATTCAT | TTAAGCAAGG | GTTTCTTCTT | CATTCCTGAT | GAAAGTGCCA | TCTAAAAAGA | 300
| TGATCTTAAT | AAATCTATTA | AGAATGAGAT | GGAGCACACT | GGATATTTTA | CTTATGAAAC | 360
| TGTTTCACTC | CTTTACTTAA | TTTATAGAGT | TACCTTCCGC | TTTTTGAAAA | TACGCAACGG | 420
| CCATTTTTTG | CACTTAGATA | CAGATTTTCT | GCGCTGTATT | GCATTGATTT | GATGCTAATC | 480
| CTGTGGTTTG | CACTAGCTTT | AAGTGGTTGA | GATCACATTT | CCTTGCTCAT | CCCCGCAACT | 540
| CCTCCCTGCC | TAATCCCCCG | CAGGATGAGG | AAGGTCAACA | TCGAGCCTGG | CAAACTAGCG | 600
| ATAACGTTGT | GTTGAAAATC | TAAGAAAAGT | GGAACTCCTA | TGTCACAACC | TATTTTTAAC | 660
| GATAAGCAAT | TTCAGGAAGC | GCTTTCACGT | CAGTGGCAGC | GTTATGGCTT | AAATTCTGCG | 720
| GCTGAAATGA | CTCCTCGCCA | GTGGTGGCTA | GCAGTGAGTG | AAGCACTGGC | CGAAATGCTG | 780
| CGTGCTCAGC | CATTCGCCAA | GCCGGTGGCG | AATCAGCGAC | ATGTTAACTA | CATCTCAATG | 840
| GAGTTTTTGA | TTGGTCGCCT | GACGGGCAAC | AACCTGTTGA | ATCTCGGCTG | GTATCAGGAT | 900
| GTACAGGATT | CGTTGAAGGC | TTATGACATC | AATCTGACGG | ACCTGCTGGA | AGAAGAGATC | 960
| GACCCGGCGC | TGGGTAACGG | TGGTCTGGGA | CGTCTGGCGG | CGTGCTTCCT | CGACTCAATG | 1020
| GCAACTGTCG | GTCAGTCTGC | GACGGGTTAC | GGTCTGAACT | ATCAATATGG | TTTGTTCCGC | 1080
| CAGTCTTTTG | TCGATGGCAA | ACAGGTTGAA | GCGCCGGATG | ACTGGCATCG | CAGTAACTAC | 1140
| CCGTGGTTCC | GCCACAACGA | AGCACTGGAT | GTGCAGGTAG | GGATTGGCGG | TAAAGTGACG | 1200
| AAAGACGGAC | GCTGGGAGCC | GGAGTTTACC | ATTACCGGTC | AAGCGTGGGA | TCTCCCCGTT | 1260
| GTCGGCTATC | GTAATGGCGT | GGCGCAGCCG | CTGCGTCTGT | GGCAGGCGAC | GCACGCGCAT | 1320
| CCGTTTGATC | TGACTAAATT | TAACGACGGT | GATTTCTTGC | GTGCCGAACA | GCAGGGCATC | 1380
| AATGCGGAAA | AACTGACCAA | AGTTCTCTAT | CCAAACGACA | ACCATACTGC | CGGTAAAAAG | 1440
| CTGCGCCTGA | TGCAGCAATA | CTTCCAGTGT | GCCTGTTCGG | TAGCGGATAT | TTTGCGTCGC | 1500
| CATCATCTGG | CGGGGCGTGA | ACTGCACGAA | CTGGCGGATT | ACTAAGTTAT | TCAGCTGAAC | 1560
| GATACCCACC | CAACTATCGC | GATTCCAGAA | CTGCTGCGCG | TGCTGATCGA | TGAGCACCAG | 1620
| ATGAGCTGGG | ATGACGCTTG | GGCCATTACC | AGCAAAACTT | TCGCTTACAC | CAACCATACC | 1680
| CTGATGCCAG | AAGCGCTGGA | ACGCTGGGAT | GTGAAACTGG | TGAAAGGCTT | ACTGCCGCGC | 1740
| CACATGCAGA | TTATTAACGA | AATTAATACT | CGCTTTAAAA | CGCTGGTAGA | GAAAACCTGG | 1800
| CCGGGCGATG | AAAAAGTGTG | GGCCAAACTG | GCGGTGGTGC | ACGACAAACA | AGTGCATATG | 1860
| GCGAACCTGT | GTGTGGTTGG | CGGTTTCGCG | GTGAACGGTG | TTGCGGCGCT | GCACTCGGAT | 1920
| CTGGTGGTGA | AGATCTGTT  | CCCGGAATAT | CACCAGCTAT | GGCCGAACAA | ATTCCATAAC | 1980
| GTCACCAACG | GTATTACCCC | ACGTCGCTGG | ATCAAACAGT | GCAACCCGGC | ACTGGCGGCT | 2040
| CTGTTGGATA | AATCACTGCA | AAAAGAGTGG | GCTAACGATC | TCGATCAGCT | GATCAATCTG | 2100
| GTTAAATTGG | CTGATGATGC | GAAATTCCGT | CAGCTTTATC | GCGTGATCAA | GCAGGCGAAT | 2160
| AAAGTCCGTC | TGGCGGAGTT | TGTGAAAGTT | CGTACCGGTA | TTGACATCAA | TCCACAGGCG | 2220

-continued

| | |
|---|---|
| ATTTTCGATA TTCAGATCAA ACGTTTGCAC GAGTACAAAC GCCAGCACCT GAATCTGCTG | 2280 |
| CGTATTCTGG CGTTGTACAA AGAAATTCGT GAAAACCCGC AGGCTGATCG CGTACCGCGC | 2340 |
| GTCTTCCTCT TCGGCGCGAA AGCGGCACCG GGCTACTACC TGGCTAAGAA TATTATCTTT | 2400 |
| GCGATCAACA AAGTGGCTGA CGTGATCAAC AACGATCCGC TGGTTGGCGA TAAGTTGAAG | 2460 |
| GTGGTGTTCC TGCCGGATTA TTGCGTTTCG GCGGCGAAA AACTGATCCC GGCGGCGGAT | 2520 |
| ATCTCCGAAC AAATTTCGAC TGCAGGTAAA GAAGCTTCCG GTACCGGCAA TATGAAACTG | 2580 |
| GCGCTCAATG GTGCGCTTAC TGTCGGTACG CTGGATGGGG CGAACGTTGA AATCGCCGAG | 2640 |
| AAAGTCGGTG AAGAAAATAT CTTTATTTTT GGTCATACGG TCAAACAAGT GAAGGCAATC | 2700 |
| GAC | 2703 |

(2) INFORMATION FOR SEQ ID NO:7:

(i) SEQUENCE CHARACTERISTICS:
      (A) LENGTH: 1391 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Escherichia coli (xi) SEQUENCE DESCRIPTION: SEQ ID NO:7:

| | |
|---|---|
| AGAGAAGCCT GTCGGCACCG TCTGGTTTGC TTTTGCCACT GCCCGCGGTG AAGGCATTAC | 60 |
| CCGGCGGGAT GCTTCAGCGG CGACCGTGAT GCGGTGCGTC GTCAGGCTAC TGCGTATGCA | 120 |
| TTGCAGACCT TGTGGCAACA ATTTCTACAA AACACTTGAT ACTGTATGAG CATACAGTAT | 180 |
| AATTGCTTCA ACAGAACATA TTGACTATCC GGTATTACCC GGCATGACAG GAGTAAAAAT | 240 |
| GGCTATCGAC GAAAACAAAC AGAAAGCGTT GGCGGCAGCA CTGGGCCAGA TTGAGAAACA | 300 |
| ATTTGGTAAA GGCTCCATCA TGCGCCTGGG TGAAGACCGT TCCATGGATG TGGAAACCAT | 360 |
| CTCTACCGGT TCGCTTTCAC TGGATATCGC GCTTGGGGCA GGTGGTCTGC CGATGGGCCG | 420 |
| TATCGTCGAA ATCTACGGAC CGGAATCTTC CGGTAAAACC ACGCTGACGC TGCAGGTGAT | 480 |
| CGCCGCAGCG CAGCGTGAAG GTAAAACCTG TGCGTTTATC GATGCTGAAC ACGCGCTGGA | 540 |
| CCCAATCTAC GCACGTAAAC TGGGCGTCGA TATCGACAAC CTGCTGTGCT CCCAGCCGGA | 600 |
| CACCGGCGAG CAGGCACTGG AAATCTGTGA CGCCCTGGCG CGTTCTGGCG CAGTAGACGT | 660 |
| TATCGTCGTT GACTCCGTGG CGGCACTGAC GCCGAAAGCG GAAATCGAAG GCGAAATCGG | 720 |
| CGACTCTCAC ATGGGCCTTG CGGCACGTAT GATGAGCCAG GCGATGCGTA AGCTGGCGGG | 780 |
| TAACCTGAAG CAGTCCAACA CGCTGCTGAT CTTCATCAAC CAGATCCGTA TGAAAATTGG | 840 |
| TGTGATGTTC GGTAACCCGG AAACCACTAC CGGTGGTAAC GCGCTGAAAT TCTACGCCTC | 900 |
| TGTTCGTCTC GACATCCGTC GTATCGGCGC GGTGAAAGAG GGCGAAAACG TGGTGGGTAG | 960 |
| CGAAACCCGC GTGAAAGTGG TGAAGAACAA AATCGCTGCG CCGTTTAAAC AGGCTGAATT | 1020 |
| CCAGATCCTC TACGGCGAAG GTATCAACTT CTACGGCGAA CTGGTTGACC TGGGCGTAAA | 1080 |
| AGAGAAGCTG ATCGAGAAAG CAGGCGCGTG GTACAGCTAC AAAGGTGAGA AGATCGGTCA | 1140 |
| GGGTAAAGCG AATGCGACTG CCTGGCTGAA AGATAACCCG GAAACCGCGA AAGAGATCGA | 1200 |
| GAAGAAAGTA CGTGAGTTGC TGCTGAGCAA CCCGAACTCA ACGCCGGATT TCTCTGTAGA | 1260 |
| TGATAGCGAA GGCGTAGCAG AAACTAACGA AGATTTTTAA TCGTCTTGTT TGATACACAA | 1320 |
| GGGTCGCATC TGCGGCCCTT TTGCTTTTTT AAGTTGTAAG GATATGCCAT GACAGAATCA | 1380 |

ACATCCCGTC G                                                         1391

(2) INFORMATION FOR SEQ ID NO:8:

(i) SEQUENCE CHARACTERISTICS:
        (A) LENGTH: 238 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:8:

TCGCCAGGAA GGCGGCATTC GGCTGGGTCA GAGTGACCTG CAGCGTGGTG TCGTTCAGCG    60

CTTTCACCCC CAACGTCTCG GGTCCCTTTT GCCCGAGGGC AATCTCGCGG GCGTTGGCGA   120

TATGCATATT GCCAGGGTAG CTCGCGTAGG GGGAGGCTGT TGCCGGCGAG ACCAGCCGTT   180

GCCAGCTCCA GACGATATCC TGCGCTGTAA TGGCCGTGCC GTCAGACCAG GTCAGACC    238

(2) INFORMATION FOR SEQ ID NO:9:

(i) SEQUENCE CHARACTERISTICS:
        (A) LENGTH: 385 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:9:

CAGCGTAATG CGCCGCGGCA TAACGGCGCC ACTATCGACA GTCAGTTCGT CAGCCTGCAG    60

CCTGGGCTGA ATCTGGGACC ATGGCGCCTG CCGAACTACA GCACCTATAG CCACAGCGAT   120

AACAACAGCC GCTGGGAGTC GGTTTACTCC TATCTTGCCC GCGATATTCA CACCCTACGC   180

AGCCAGCTGG TGGTCGGTAA TACGTATACC TCTTCCGGCA TTTTCGACAG TTTGAGTTTT   240

ACCGGTCTGC AGCTCAGTTC GACAAAGAGA TGCTGCCGGA TAGCCTGCAT GCTTTGCGCC   300

GACGATTCGA GGGATCGCGC GCACCACCGC GGAGGTCTCG GTTTATCAGA ATGGTTACAG   360

CATTTATAAA ACCACCGTCG CTACC                                         385

(2) INFORMATION FOR SEQ ID NO:10:

(i) SEQUENCE CHARACTERISTICS:
        (A) LENGTH: 462 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:10:

CTCTATATTC AGGACGAACA TATCTGGACC TCTGGCGGGG TCAGTTCCGG CTTTGATCGC    60

CCTGCACCCG CAGCGGGTGA TCGCCCCTCA TCTGCTACTG CGGCGCTGCA ACAGGCGACG   120

ATCGATGACG TTATTCCTGG CCAGCAAACA GCAGACCAAT TAAGGTCTGA TAGTGGCTCT   180

CTTCCTCCGG CGCGCGACGG TCCAGGCGGC TCAACAGTTT GGTGCATAGC GCTTTGCGGT   240

-continued

| | |
|---|---|
| TGAGATGACG CCCTTCGTTA AGAATATCCA TCACGATCTC CGTCCATGGA GAGTAGCGTT | 300 |
| TATTCCAGAA TAGGGTTTTT CAGGATCTCA TGGATCTGCG CCTGCTTATC GCTATTTTGT | 360 |
| AACCAGATCG CATAAAGTGG ACGGGATAAC GTAGCGCTGT CCATGACCGT ATGTAACCCA | 420 |
| TGCTTCTCTT TCGCCCAGCG AGCAGGTAGC CAACAGCAGC CG | 462 |

(2) INFORMATION FOR SEQ ID NO:11:

(i) SEQUENCE CHARACTERISTICS:
        (A) LENGTH: 730 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:11:

| | |
|---|---|
| GCTGACCGCT AAACTGGGTT ACCCGATCAC TGACGATCTG GACATCTACA CCCGTCTGGG | 60 |
| CGGCATGGTT TGGCGCGCTG ACTCCAAAGG CAACTACGCT TCAACCGGCG TTTCCCGTAG | 120 |
| CGAACACGAC ACTGGCGTTT CCCCAGTATT TGCTGGCGGC GTAGAGTGGG CTGTTACTCG | 180 |
| TGACATCGCT ACCCGTCTGG AATACCAGTG GGTTAACAAC ATCGGCGACG CGGGCACTGT | 240 |
| GGGTACCCGT CCTGATAACG GCATGCTGAG CCTGGGCGTT TCCTACCGCT TCGGTCAGGA | 300 |
| AGATGCTGCA CCGGTTGTTG CTCCGGCTCC GGCTCCGGCT CCGGAAGTGG CTACCAAGCA | 360 |
| CTTCACCCTG AAGTCTGACG TTCTGTTCAA CTTCAACAAA GCTACCCTGA AACCGGAAGG | 420 |
| TCAGCAGGCT CTGGATCAGC TGTACACTCA GCTGAGCAAC ATGGATCCGA AAGACGGTTC | 480 |
| CGCTGTTGTT CTGGGCTACA CCGACCGCAT CGGTTCCGAA GCTTACAACC AGCAGCTGTC | 540 |
| TGAGAAACGT GCTCAGTCCG TTGTTGACTA CCTGGTTGCT AAAGGCATCC CGGCTGGCAA | 600 |
| AATCTCCGCT CGCGGCATGG GTGAATCCAA CCCGGTTACT GGCAACACCT GTGACAACGT | 660 |
| GAAAGCTCGC GCTGCCCTGA TCGATTGCCT GGCTCCGGAT CGTCGTGTAG AGATCGAAGT | 720 |
| TAAAGGTATC | 730 |

(2) INFORMATION FOR SEQ ID NO:12:

(i) SEQUENCE CHARACTERISTICS:
        (A) LENGTH: 225 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:12:

| | |
|---|---|
| CGCTACTGTT TAAATCTCAT TTGAAACATC GCAAAGTCAG TGAACCACAT ATTCGAGGAT | 60 |
| GGCATGCACT AGAAAATATT AATAAGATTT TAGCGAAACC TAATCAGCGC AATATCGCTT | 120 |
| AATTATTTTA GGTATGTTCT CTTCTATCCT ACAGTCACGA GGCAGTGTCG AACTTGATCC | 180 |
| TCATTTTATT AATCACATGA CCAATGGTAT AAGCGTCGTC ACATA | 225 |

(2) INFORMATION FOR SEQ ID NO:13:

(i) SEQUENCE CHARACTERISTICS:
        (A) LENGTH: 402 base pairs
        (B) TYPE: nucleic acid (C) STRANDEDNESS: double
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:13:

```
ACATTTTAAA TAGGAAGCCA CCTGATAACA TCCCCGCAGT TGGATCATCA GATTTATAGC      60
GGCATTTGGT ATCCGCTAGA TAAAAGCAGT CCAACGATCC CGCCAATTGT TAGATGAAAT     120
TGGACTATTC TTTTTATTTG CTCCGCTTTA TCACAGTGGT TTTCGCTTTG CCGCCCCTGT     180
GCGCCAACAG CTAAGAACAC GCACGCTCTT TAATGTGTTA GGCCCATTAA TTAATCCAGC     240
GCGTTCCGCC TTTAGCATTA ATTGGTGTTT ATAGTCCTGA ATTATTAATG CCTATTGCAG     300
ATACCTTAAA TGTCTTGGGC TACAAACGTG CGGCAGTGGT CCATAGTGGT GGAATGGATG     360
AAGTGTCATT ACATGCTCCC ACACAAGTGG CTGAGTTACA CA                        402
```

(2) INFORMATION FOR SEQ ID NO:14:

(i) SEQUENCE CHARACTERISTICS:
        (A) LENGTH: 157 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:14:

```
CTGAAACGCA TTTATGCGGG AGTCAGTGAA ATCATCACTC AATTTTCACC CGATGTATTT      60
TCTGTTGAAC AAGTCTTTAT GGCAAAAAAT GCAGACTCAG CATTAAAATT AGGCCAAGCA     120
AGAGGTGTGG CGATTTTAGC GGCAGTCAAT AATGATC                              157
```

(2) INFORMATION FOR SEQ ID NO:15:

(i) SEQUENCE CHARACTERISTICS:
        (A) LENGTH: 1348 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:15:

```
TTTCTCTTTA AAATCAATTC TTAAAGAAAT TATTAATAAT TAACTTGATA CTGTATGATT      60
ATACAGTATA ATGAGTTTCA ACAAGCAAAA TCATATACGT TTTAATGGTA GTGACCCATC     120
TTTATGCTTC ACTGCCCAGA GGGAGATAAC ATGGCTATTG ATGAAAACAA ACAAAAAGCA     180
TTGGCCGCAG CACTTGGTCA AATTGAAAAG CAATTTGGTA AAGGTTCTAT CATGCGTCTG     240
GGCGAAGACC GTTCCATGAA CGTAGAAACT ATCTCTACAG GATCTTTATC ATTAGACGTT     300
GCTTTAGGTG CAGGTGGATT GCCACGTGGC CGTATTGTTG AAATCTATGG CCCTGAATCT     360
TCTGGTAAAA CAACCTTGAC TCTACAAGTT ATTGCCTCTG CTCAGCGTGA AGGAAAAATT     420
TGTGCATTTA TTGATGCTGA ACATGCATTA GACCCAATTT ATGCTCAAAA GCTAGGTGTC     480
GATATCGATA ATCTACTCTG CTCTCAACCT GACACAGGTG AACAAGCTCT GGAAATTTGT     540
```

```
GATGCATTAT CTCGCTCTGG TGCGGTCGAT GTTATTGTCG TGGACTCCGT GGCAGCATTA      600

ACACCAAAAG CTGAAATTGA AGGTGAAATT GGTGATTCAC ACGTTGGTTT AGCCGCACGT      660

ATGATGAGCC AAGCTATGCG TAAACTAGCG GGTAACCTTA AAAACTCTAA TACACTGCTG      720

ATTTTCATTA ACCAAATTCG TATGAAAATC GGTGTTATGT TTGGTAACCC AGAAACCACG      780

ACCGGTGGTA ATGCGCTTAA ATTCTATGCT TCTGTTCGTT TAGACATTCG TCGCATTGGC      840

TCTGTCAAAA ATGGTGATGA AGTCATTGGT AGTGAGACTC GCGTTAAAGT TGTTAAAAAT      900

AAAGTGGCTG CACCGTTTAA ACAAGCTGAA TTCCAAATTA TGTACGGTGA AGGTATTAAT      960

ACCTATGGCG AACTGATTGA TTTAGGTGTT AAACATAAGT TAGTAGAGAA AGCAGGTGCT     1020

TGGTATAGCT ACAATGGCGA AAAAATTGGT CAAGGTAAAG CTAACGCAAC CAATTACTTA     1080

AAAGAACATC CTGAAATGTA CAATGAGTTA AACACTAAAT TGCGTGAAAT GTTGTTAAAT     1140

CATGCTGGTG AATTCACAAG TGCTGCGGAT TTTGCAGGTG AAGAGTCAGA CAGTGATGCT     1200

GACGACACAA AAGAGTAATT AGCTGGTTGT CATGCTGTTT GTGTGAAAAT AGACCTTAAA     1260

TCATTGGCTA TTATCACGAC AGCATCCCAT AGAATAACTT GTTTGTATAA ATTTTATTCA     1320

GATGGCAAAG GAAGCCTTAA AAAAGCTT                                         1348
```

(2) INFORMATION FOR SEQ ID NO:16:

(i) SEQUENCE CHARACTERISTICS:
        (A) LENGTH: 2167 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:16:

```
GGTACCGCTG GCCGAGCATC TGCTCGATCA CCACCAGCCG GGCGACGGGA ACTGCACGAT       60

CTACCTGGCG AGCCTGGAGC ACGAGCGGGT TCGCTTCGTA CGGCGCTGAG CGACAGTCAC      120

AGGAGAGGAA ACGGATGGGA TCGCACCAGG AGCGGCCGCT GATCGGCCTG CTGTTCTCCG      180

AAACCGGCGT CACCGCCGAT ATCGAGCGCT CGCACGCGTA TGGCGCATTG CTCGCGGTCG      240

AGCAACTGAA CCGCGAGGGC GGCGTCGGCG GTCGCCCGAT CGAAACGCTG TCCCAGGACC      300

CCGGCGGCGA CCCGGACCGC TATCGGCTGT GCGCCGAGGA CTTCATTCGC AACCGGGGGG      360

TACGGTTCCT CGTGGGCTGC TACATGTCGC ACACGCGCAA GGCGGTGATG CCGGTGGTCG      420

AGCGCGCCGA CGCGCTGCTC TGCTACCCGA CCCCCTACGA GGGCTTCGAG TATTCGCCGA      480

ACATCGTCTA CGGCGGTCCG GCGCCGAACC AGAACAGTGC GCCGCTGGCG GCGTACCTGA      540

TTCGCCACTA CGGCGAGCGG GTGGTGTTCA TCGGCTCGGA CTACATCTAT CCGCGGGAAA      600

GCAACCATGT GATGCGCCAC CTGTATCGCC AGCACGGCGG CACGGTGCTC GAGGAAATCT      660

ACATTCCGCT GTATCCCTCC GACGACGACT TGCAGCGCGC CGTCGAGCGC ATCTACCAGG      720

CGCGCGCCGA CGTGGTCTTC TCCACCGTGG TGGGCACCGG CACCGCCGAG CTGTATCGCG      780

CCATCGCCCG TCGCTACGGC GACGGCAGGC GGCCGCCGAT CGCCAGCCTG ACCACCAGCG      840

AGGCGGAGGT GGCGAAGATG GAGAGTGACG TGGCAGAGGG GCAGGTGGTG GTCGCGCCTT      900

ACTTCTCCAG CATCGATACG CCCGCCAGCC GGGCCTTCGT CCAGGCCTGC CATGGTTTCT      960

TCCCGGAGAA CGCGACCATC ACCGCCTGGG CCGAGGCGG CTACTGGCAG ACCTTGTTGC     1020

TCGGCCGCGC CGCGCAGGCC GCAGGCAACT GGCGGGTGGA AGACGTGCAG CGGCACCTGT     1080
```

-continued

| | |
|---|---|
| ACGACATCGA CATCGACGCG CCACAGGGGC CGGTCCGGGT GGAGCGCCAG AACAACCACA | 1140 |
| GCCGCCTGTC TTCGCGCATC GCGGAAATCG ATGCGCGCGG CGTGTTCCAG GTCCGCTGGC | 1200 |
| AGTCGCCCGA ACCGATTCGC CCCGACCCTT ATGTCGTCGT GCATAACCTC GACGACTGGT | 1260 |
| CCGCCAGCAT GGGCGGGGGA CCGCTCCCAT GAGCGCCAAC TCGCTGCTCG GCAGCCTGCG | 1320 |
| CGAGTTGCAG GTGCTGGTCC TCAACCCGCC GGGGGAGGTC AGCGACGCCC TGGTCTTGCA | 1380 |
| GCTGATCCGC ATCGGTTGTT CGGTGCGCCA GTGCTGGCCG CCGCCGGAAG CCTTCGACGT | 1440 |
| GCCGGTGGAC GTGGTCTTCA CCAGCATTTT CCAGAATGGC CACCACGACG AGATCGCTGC | 1500 |
| GCTGCTCGCC GCCGGGACTC CGCGCACTAC CCTGGTGGCG CTGGTGGAGT ACGAAAGCCC | 1560 |
| CGCGGTGCTC TCGCAGATCA TCGAGCTGGA GTGCCACGGC GTGATCACCC AGCCGCTCGA | 1620 |
| TGCCCACCGG GTGCTGCCTG TGCTGGTATC GGCGCGGCGC ATCAGCGAGG AAATGGCGAA | 1680 |
| GCTGAAGCAG AAGACCGAGC AGCTCCAGGA CCGCATCGCC GGCCAGGCCC GGATCAACCA | 1740 |
| GGCCAAGGTG TTGCTGATGC AGCGCCATGG CTGGACGAG CGCGAGGCGC ACCAGCACCT | 1800 |
| GTCGCGGGAA GCGATGAAGC GGCGCGAGCC GATCCTGAAG ATCGCTCAGG AGTTGCTGGG | 1860 |
| AAACGAGCCG TCCGCCTGAG CGATCCCGGGC CGACCAGAAC AATAACAAGA GGGGTATCGT | 1920 |
| CATCATGCTG GGACTGGTTC TGCTGTACGT TGGCGCGGTG CTGTTTCTCA ATGCCGTCTG | 1980 |
| GTTGCTGGGC AAGATCAGCG GTCGGGAGGT GGCGGTGATC AACTTCCTGG TCGGCGTGCT | 2040 |
| GAGCGCCTGC GTCGCGTTCT ACCTGATCTT TTCCGCAGCA GCCGGGCAGG GCTCGCTGAA | 2100 |
| GGCCGGAGCG CTGACCCTGC TATTCGCTTT TACCTATCTG TGGGTGGCCG CCAACCAGTT | 2160 |
| CCTCGAG | 2167 |

(2) INFORMATION FOR SEQ ID NO:17:

(i) SEQUENCE CHARACTERISTICS:
        (A) LENGTH: 1872 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:17:

| | |
|---|---|
| GAATTCCCGG GAGTTCCCGA CGCAGCCACC CCCAAAACAC TGCTAAGGGA GCGCCTCGCA | 60 |
| GGGCTCCTGA GGAGATAGAC CATGCCATTT GGCAAGCCAC TGGTGGGCAC CTTGCTCGCC | 120 |
| TCGCTGACGC TGCTGGGCCT GGCCACCGCT CACGCCAAGG ACGACATGAA AGCCGCCGAG | 180 |
| CAATACCAGG GTGCCGCTTC CGCCGTCGAT CCCGCTCACG TGGTGCGCAC CAACGGCGCT | 240 |
| CCCGACATGA GTGAAAGCGA GTTCAACGAG GCCAAGCAGA TCTACTTCCA ACGCTGCGCC | 300 |
| GGTTGCCACG GCGTCCTGCG CAAGGGCGCC ACCGGCAAGC CGCTGACCCC GGACATCACC | 360 |
| CAGCAACGCG GCCAGCAATA CCTGGAAGCG CTGATCACCT ACGGCACCCC GCTGGGCATG | 420 |
| CCGAACTGGG GCAGCTCCGG CGAGCTGAGC AAGGAACAGA TCACCCTGAT GGCCAAGTAC | 480 |
| ATCCAGCACA CCCCGCCGCA ACCGCCGGAG TGGGGCATGC CGGAGATGCG CGAATCGTGG | 540 |
| AAGGTGCTGG TGAAGCCGGA GGACCGGCCG AAGAACAGC TCAACGACCT CGACCTGCCC | 600 |
| AACCTGTTCT CGGTGACCCT GCGCGACGCC GGGCAGATCG CCCTGGTCGA CGGCGACAGC | 660 |
| AAAAAGATCG TCAAGGTCAT CGATACCGGC TATGCCGTGC ATATCTCGCG GATGTCCGCT | 720 |
| TCCGGCCGCT ACCTGCTGGT GATCGGCCGC GACGCGCGGA TCGACATGAT CGACCTGTGG | 780 |

-continued

| | |
|---|---|
| GCCAAGGAGC CGACCAAGGT CGCCGAGATC AAGATCGGCA TCGAGGCGCG CTCGGTGGAA | 840 |
| AGCTCCAAGT TCAAGGGCTA CGAGGACCGC TACACCATCG CCGGCGCCTA CTGGCCGCCG | 900 |
| CAGTTCGCGA TCATGGACGG CGAGACCCTG GAACCGAAGC AGATCGTCTC CACCCGCGGC | 960 |
| ATGACCGTAG ACACCCAGAC CTACCACCCG GAACCGCGCG TGGCGGCGAT CATCGCCTCC | 1020 |
| CACGAGCACC CCGAGTTCAT CGTCAACGTG AAGGAGACCG GCAAGGTCCT GCTGGTCAAC | 1080 |
| TACAAGGATA TCGACAACCT CACCGTCACC AGCATCGGTG CGGCGCCGTT CCTCCACGAC | 1140 |
| GGCGGCTGGG ACAGCAGCCA CCGCTACTTC ATGACCGCCG CCAACAACTC CAACAAGGTT | 1200 |
| GCCGTGATCG ACTCCAAGGA CCGTCGCCTG TCGGCCCTGG TCGACGTCGG CAAGACCCCG | 1260 |
| CACCCGGGGC GTGGCGCCAA CTTCGTGCAT CCCAAGTACG GCCCGGTGTG GAGCACCAGC | 1320 |
| CACCTGGGCG ACGGCAGCAT CTCGCTGATC GGCACCGATC CGAAGAACCA TCCGCAGTAC | 1380 |
| GCCTGGAAGA AAGTCGCCGA ACTACAGGGC CAGGGCGGCG GCTCGCTGTT CATCAAGACC | 1440 |
| CATCCGAAGT CCTCGCACCT CTACGTCGAC ACCACCTTCA ACCCCGACGC CAGGATCAGC | 1500 |
| CAGAGCGTCG CGGTGTTCGA CCTGAAGAAC CTCGACGCCA AGTACCAGGT GCTGCCGATC | 1560 |
| GCCGAATGGG CCGATCTCGG CGAAGGCGCC AAGCGGGTGG TGCAGCCCGA GTACAACAAG | 1620 |
| CGCGGCGATG AAGTCTGGTT CTCGGTGTGG AACGGCAAGA ACGACAGCTC CGCGCTGGTG | 1680 |
| GTGGTGGACG ACAAGACCCT GAAGCTCAAG GCCGTGGTCA AGGACCCGCG GCTGATCACC | 1740 |
| CCGACCGGTA AGTTCAACGT CTACAACACC CAGCACGACG TGTACTGAGA CCCGCGTGCG | 1800 |
| GGGCACGCCC CGCACGCTCC CCCCTACGAG GAACCGTGAT GAAACCGTAC GCACTGCTTT | 1860 |
| CGCTGCTCGC CA | 1872 |

(2) INFORMATION FOR SEQ ID NO:18:

(i) SEQUENCE CHARACTERISTICS:
        (A) LENGTH: 3451 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:18:

| | |
|---|---|
| TCGAGACGGG AAGCCACTCT CTACGAGAAG ACAGAAGCCC CTCACAGAGG CCTCTGTCTA | 60 |
| CGCCTACTAA AGCTCGGCTT ATTCATATGT ATTTATATTC TTTCAATAGA TCACTCAGCG | 120 |
| CTATTTTAAG TTCACCCTCT GTAAGTTCAC CTGGGCGCTC TTTCTTTCCT TCGGTAAAGC | 180 |
| TGTCGGCCAG ACCAAACATT AAACTCAAGC ATCTCCCAAG CGATGCATCA TCTTGGGCCA | 240 |
| GCATCCCTGA ATCGCGCGTC GGACCTCCAA GTCTTAAAAA ATTCTTCGCT GAAGGTTTTC | 300 |
| CCATCAATCG ATGAGGCTAA TAGCTTCTTT GCAATATCTA TCATTTCCAT GCTCACCTTA | 360 |
| AAGCACCTCA TTTTTCATGT AAAAATTGTA TTGATCCGTG CCAGACTCAA TCCTCCACCC | 420 |
| AGAAACAAAC ATCCCATCCT CTCCAATGAT AACAACAATA TTAGTCCTGG CATTGTAATG | 480 |
| TACTTTTGAG TTTACTTCGG AGTGGTAAGT CCCTTTTTCT ACGGTTGCAG GATCAGCAAG | 540 |
| GTGCTCAAGA ATTTTATCCC TAAACTCTGC AAGCGTTCCA TTGTTGGCGC TTTTTTCACC | 600 |
| CAGCCCAAAA TCATATTTGT GGCTATCAAA TTTTTTCTGT AGTTGCCTCC GTGTGAAGAT | 660 |
| ACCACTATCA AGAGGACTAC TGAGCATTAC ATAAACAGGT TTGACTCCAG AATCCGCCGG | 720 |
| GAAAATCACG ATCAGATCGT TTAGGTCCAG TAGCATTCCC GGATAGGACT CCGGGCCGGT | 780 |

-continued

| | |
|---|---|
| CTTCAACGGT GTGAGGGCCG CTCCCTCATA TACCGGCACC GGCTTCGGTA TGACCGGAGT | 840 |
| GGTACTCGAA GGGTTCTGGT TTCCTGGAGG ACTCGCCGGC GTCCAAGTCA GGATCAGTGG | 900 |
| CGGCGCTTCT GCGACCGTAG AGGGAACCGT AACCTCGTAC AGTCCTGTTG CGGCGTTATA | 960 |
| GGCCCCATCC GGACCGGAAC GCTTTCGGAA CGCTCACACC ATCGGTCTGA CCACCGAAAG | 1020 |
| GTCGTCGTGT TGCCTCGCGC CTCGTTGGTC AGGCGCATCG GCAGATCGAC GGTACCGCTG | 1080 |
| GCTTTTGCAA CCGCGTTCAG GTTTACGCTT GGGGGAAGCC CCAATTTAGC GGCATCCATG | 1140 |
| CCCAGGGCGT AACGAACGCT ATCGGGCGTT TGGTCCTGCC ATTGCTCGGC AGTCCGGGAG | 1200 |
| AGTAGGTCAG ACTGGCAAGC CACGGCCATC ACCGAGGTGC TGAAGCCAGG ACCGCCAGGA | 1260 |
| CGGCAATCGC ATCGGAGATC GCTTGAGCAA GGGATGCGGC GCCTGTGCGA CCTGGATCAG | 1320 |
| ACCCCGCTGC GGCGGTGGCG CACCCGCTGC CATTGGCTGG CATGGCATAA GTATTGGCAG | 1380 |
| CCCTGATCGC CGCTTGACGA GCGATTTCCT TGCGCCTTGC CGTTTCGGCG TTCAGCTTGT | 1440 |
| CCAGCCGTGC TTGCAGGCTG GCGATTTCAT CCACTAGGTA GGACATCGGC GTTGTAGGTT | 1500 |
| GCCTTTTGTT TCTCCAGTGC ATTGGGTGCC TTGGCAATCA AGGCATTGTT TGCAGTCTGC | 1560 |
| AATTCTTCTT ATTGCGATCG CCTGCGTAAG GAGTTGAGTA GCGCGTTCAA GCCACTGCTC | 1620 |
| TGGCGTTGGA TTGGTCAGTT GAGGCAAAGC ATTCCCAGCC TGGTCAAGCT CGGACTGCAC | 1680 |
| TTTTTTCTCG ACATTTGCCT TCCTGGCCTT GTAGTCCGCC TCCACCTCAG CAGCGGCTCG | 1740 |
| CTGGGCTTCT GCTTCCAATG ACCGGGCTTT ATTCTCCAGC TCTTGAGACG TTTGTTTCAA | 1800 |
| GATAGCGATT TGCGCCTTAT AGATATCGGC GCTGTACGCT TTGGCCAGCT CACTCATATG | 1860 |
| GCGATCCAGG AACTCTCCAT AGAATTTTCG GCTGGCCAGC AACTGACTCT GGTACATCGA | 1920 |
| CTCTGACTTC TGAGGAAAGT CTGAAGCCGT ATAAAGATTG GCCGGGCGAT CCTCAATGAC | 1980 |
| CTTTAGCGAT TTTGCTTTGG CATCCATGAG TGCATCAACG ATACTCTTTT CATCGCGGAT | 2040 |
| GTCATTGGCA CTGACCGCTT TACCTGGCAA CCCCGCTTCA CTCTTGAGTT CATCAACCTC | 2100 |
| CTTCAGGGTT TCATTTTTCA GGTTTTTCTT GAGTTCTGAA TGGGACTTAT CAAGCGTACT | 2160 |
| TCTTAGCTTC CTGTACTCCT GCATTCCAGT ACCGACATAC GGACTTGGTC CTGGTGGGAC | 2220 |
| AAATGGTGGA GTACCGTAGC TTGATCGAGC AGGAATATAC TGGATTATGT CACGCCCACC | 2280 |
| ACCCTGCACA TGTGTAATAA CCATCGAACC AGGTTCGTAA TCATTGACAG CCATAGATCG | 2340 |
| CCCCTACATT AATTTGAAAG TGTAATGTAT TGAGCGACTC CCACCTAGAG AACCCTCTCC | 2400 |
| CAGTCAATAA GCCCCAATGC ATCGGCAATA CACTGCAATC AACTTCAATA TCCCGTGTTT | 2460 |
| AGATGATCCA GAAGGTGCGC TCTCTCGCCT CTTATAATCG CGCCTGCGTC AAACGGTCAT | 2520 |
| TTCCTTAACG CACACCTCAT CTACCCCGGC CAGTCACGGA AGCCGCATAC CTTCGGTTCA | 2580 |
| TTAACGAACT CCCACTTTCA AAATTCATCC ATGCCGCCCC TTCGCGAGCT TCCGGACAAA | 2640 |
| GCCACGCTGA TTGCGAGCCC AGCGTTTTTG ATTGCAAGCC GCTGCAGCTG GTCAGGCCGT | 2700 |
| TTCCGCAACG CTTGAAGTCC TGGCCGATAT ACCGGCAGGG CCAGCCATCG TTCGACGAAT | 2760 |
| AAAGCCACCT CAGCCATGAT GCCCTTTCCA TCCCCAGCGG AACCCGACA TGGACGCCAA | 2820 |
| AGCCCTGCTC CTCGGCAGCC TCTGCCTGGC CGCCCCATTC GCCGACGCGG CGACGCTCGA | 2880 |
| CAATGCTCTC TCCGCCTGCC TCGCCGCCCG GCTCGGTGCA CCGCACACGG CGGAGGGCCA | 2940 |
| GTTGCACCTG CCACTCACCC TTGAGGCCCG GCGCTCCACC GGCGAATGCG GCTGTACCTC | 3000 |
| GGCGCTGGTG CGATATCGGC TGCTGGCCAG GGGCGCCAGC GCCGACAGCC TCGTGCTTCA | 3060 |
| AGAGGGCTGC TCGATAGTCG CCAGGACACG CCGCGCACGC TGACCCTGGC GGCGGACGCC | 3120 |
| GGCTTGGCGA GCGGCCGCGA ACTGGTCGTC ACCCTGGGTT GTCAGGCGCC TGACTGACAG | 3180 |

-continued

```
GCCGGGCTGC CACCACCAGG CCGAGATGGA CGCCCTGCAT GTATCCTCCG ATCGGCAAGC      3240

CTCCCGTTCG CACATTCACC ACTCTGCAAT CCAGTTCATA AATCCCATAA AAGCCCTCTT      3300

CCGCTCCCCG CCAGCCTCCC CGCATCCCGC ACCCTAGACG CCCCGCCGCT CTCCGCCGGC      3360

TCGCCCGACA AGAAAAACCA ACCGCTCGAT CAGCCTCATC CTTCACCCAT CACAGGAGCC      3420

ATCGCGATGC ACCTGATACC CCATTGGATC C                                     3451
```

(2) INFORMATION FOR SEQ ID NO:19:

(i) SEQUENCE CHARACTERISTICS:
        (A) LENGTH: 744 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:19:

```
GGGTTCAGCA AGCGTTCAGG GGCGGTTCAG TACCCTGTCC GTACTCTGCA AGCCGTGAAC       60

GACACGACTC TCGCAGAACG GAGAAACACC ATGAAAGCAC TCAAGACTCT CTTCATCGCC      120

ACCGCCCTGC TGGGTTCCGC CGCCGGCGTC CAGGCCGCCG ACAACTTCGT CGGCCTGACC      180

TGGGGCGAGA CCAGCAACAA CATCCAGAAA TCCAAGTCGC TGAACCGCAA CCTGAACAGC      240

CCGAACCTCG ACAAGGTGAT CGACAACACC GGCACCTGGG GCATCCGCGC CGGCCAGCAG      300

TTCGAGCAGG GCCGCTACTA CGCGACCTAC GAGAACATCT CCGACACCAG CAGCGGCAAC      360

AAGCTGCGCC AGCAGAACCT GCTCGGCAGC TACGACGCCT TCCTGCCGAT CGGCGACAAC      420

AACACCAAGC TGTTCGGCGG TGCCACCCTC GGCCTGGTCA AGCTGGAACA GGACGGCAAG      480

GGCTTCAAGC GCGACAGCGA TGTCGGCTAC GCTGCCGGGC TGCAGGCCGG TATCCTGCAG      540

GAGCTGAGCA AGAATGCCTC GATCGAAGGC GGCTATCGTT ACCTGCGCAC CAACGCCAGC      600

ACCGAGATGA CCCCGCATGG CGGCAACAAG CTGGGCTCCC TGGACCTGCA CAGCAGCTCG      660

CAATTCTACC TGGGCGCCAA CTACAAGTTC TAAATGACCG CGCAGCGCCC GCGAGGGCAT      720

GCTTCGATGG CCGGGCCGGA AGGT                                             744
```

(2) INFORMATION FOR SEQ ID NO:20:

(i) SEQUENCE CHARACTERISTICS:
        (A) LENGTH: 2760 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:20:

```
CTGCAGCTGG TCAGGCCGTT TCCGCAACGC TTGAAGTCCT GGCCGATATA CCGGCAGGGC       60

CAGCCATCGT TCGACGAATA AAGCCACCTC AGCCATGATG CCCTTTCCAT CCCCAGCGGA      120

ACCCCGACAT GGACGCCAAA GCCCTGCTCC TCGGCAGCCT CTGCCTGGCC GCCCCATTCG      180

CCGACGCGGC GACGCTCGAC AATGCTCTCT CCGCCTGCCT CGCCGCCCGG CTCGGTGCAC      240

CGCACACGGC GGAGGGCCAG TTGCACCTGC CACTCACCCT TGAGGCCCGG CGCTCCACCG      300

GCGAATGCGG CTGTACCTCG GCGCTGGTGC GATATCGGCT GCTGGCCAGG GGCGCCAGCG      360
```

-continued

```
CCGACAGCCT CGTGCTTCAA GAGGGCTGCT CGATAGTCGC CAGGACACGC CGCGCACGCT    420
GACCCTGGCG GCGGACGCCG GCTTGGCGAG CGGCCGCGAA CTGGTCGTCA CCCTGGGTTG    480
TCAGGCGCCT GACTGACAGG CCGGGCTGCC ACCACCAGGC CGAGATGGAC GCCCTGCATG    540
TATCCTCCGA TCGGCAAGCC TCCCGTTCGC ACATTCACCA CTCTGCAATC CAGTTCATAA    600
ATCCCATAAA AGCCCTCTTC CGCTCCCCGC CAGCCTCCCC GCATCCCGCA CCCTAGACGC    660
CCCGCCGCTC TCCGCCGGCT CGCCCGACAA GAAAAACCAA CCGCTCGATC AGCCTCATCC    720
TTCACCCATC ACAGGAGCCA TCGCGATGCA CCTGATACCC CATTGGATCC CCCTGGTCGC    780
CAGCCTCGGC CTGCTCGCCG GCGGCTCGTC CGCGTCCGCC GCCGAGGAAG CCTTCGACCT    840
CTGGAACGAA TGCGCCAAAG CCTGCGTGCT CGACCTCAAG GACGGCGTGC GTTCCAGCCG    900
CATGAGCGTC GACCCGGCCA TCGCCGACAC CAACGGCCAG GGCGTGCTGC ACTACTCCAT    960
GGTCCTGGAG GGCGGCAACG ACGCGCTCAA GCTGGCCATC GACAACGCCC TCAGCATCAC   1020
CAGCGACGGC CTGACCATCC GCCTCGAAGG CGGCGTCGAG CCGAACAAGC CGGTGCGCTA   1080
CAGCTACACG CGCCAGGCGC GCGGCAGTTG GTCGCTGAAC TGGCTGGTAC CGATCGGCCA   1140
CGAGAAGCCC TCGAACATCA AGGTGTTCAT CCACGAACTG AACGCCGGCA ACCAGCTCAG   1200
CCACATGTCG CCGATCTACA CCATCGAGAT GGGCGACGAG TTGCTGGCGA AGCTGGCGCG   1260
CGATGCCACC TTCTTCGTCA GGGCGCACGA GAGCAACGAG ATGCAGCCGA CGCTCGCCAT   1320
CAGCCATGCC GGGGTCAGCG TGGTCATGGC CCAGACCCAG CCGCGCCGGG AAAAGCGCTG   1380
GAGCGAATGG GCCAGCGGCA AGGTGTTGTG CCTGCTCGAC CCGCTGGACG GGGTCTACAA   1440
CTACCTCGCC CAGCAACGCT GCAACCTCGA CGATACCTGG GAAGGCAAGA TCTACCGGGT   1500
GCTCGCCGGC AACCCGGCGA AGCATGACCT GGACATCAAA CCCACGGTCA TCAGTCATCG   1560
CCTGCACTTT CCCGAGGGCG GCAGCCTGGC CGCGCTGACC GCGCACCAGG CTTGCCACCT   1620
GCCGCTGGAG ACTTTCACCC GTCATCGCCA GCCGCGCGGC TGGAACAAC  TGGAGCAGTG   1680
CGGCTATCCG GTGCAGCGGC TGGTCGCCCT CTACCTGGCG GCGCGGCTGT CGTGGAACCA   1740
GGTCGACCAG GTGATCCGCA ACGCCCTGGC CAGCCCCGGC AGCGGCGGCG ACCTGGGCGA   1800
AGCGATCCGC GAGCAGCCGG AGCAGGCCCG TCTGGCCCTG ACCCTGGCCG CCGCCGAGAG   1860
CGAGCGCTTC GTCCGGCAGG GCACCGGCAA CGACGAGGCC GGCGCGGCCA ACGCCGACGT   1920
GGTGAGCCTG ACCTGCCCGG TCGCCGCCGG TGAATGCGCG GGCCCGGCGG ACAGCGGCGA   1980
CGCCCTGCTG GAGCGCAACT ATCCCACTGG CGCGGAGTTC CTCGGCGACG GCGGCGACGT   2040
CAGCTTCAGC ACCCGCGGCA CGCAGAACTG GACGGTGGAG CGGCTGCTCC AGGCGCACCG   2100
CCAACTGGAG GAGCGCGGCT ATGTGTTCGT CGGCTACCAC GGCACCTTCC TCGAAGCGGC   2160
GCAAAGCATC GTCTTCGGCG GGGTGCGCGC GCGCAGCCAG GACCTCGACG CGATCTGGCG   2220
CGGTTTCTAT ATCGCCGGCG ATCCGGCGCT GGCCTACGGC TACGCCCAGG ACCAGGAACC   2280
CGACGCACGC GGCCGGATCC GCAACGGTGC CCTGCTGCGG GTCTATGTGC CGCGCTCGAG   2340
CCTGCCGGGC TTCTACCGCA CCAGCCTGAC CCTGGCCGCG CCGGAGGCGG CGGGCGAGGT   2400
CGAACGGCTG ATCGGCCATC CGCTGCCGCT GCGCCTGGAC GCCATCACCG GCCCCGAGGA   2460
GGAAGGCGGG CGCCTGGAGA CCATTCTCGG CTGGCCGCTG GCCGAGCGCA CCGTGGTGAT   2520
TCCCTCGGCG ATCCCCACCG ACCCGCGCAA CGTCGGCGGC GACCTCGACC CGTCCAGCAT   2580
CCCCGACAAG GAACAGGCGA TCAGCGCCCT GCCGGACTAC GCCAGCCAGC CCGGCAAACC   2640
GCCGCGCGAG GACCTGAAGT AACTGCCGCG ACCGGCCGGC TCCCTTCGCA GGAGCCGGCC   2700
TTCTCGGGGC CTGGCCATAC ATCAGGTTTT CCTGATGCCA GCCCAATCGA ATATGAATTC   2760
```

(2) INFORMATION FOR SEQ ID NO:21:

(i) SEQUENCE CHARACTERISTICS:
        (A) LENGTH: 172 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:21:

```
TTGATGAAAT GCATCGATTA ATAAATTTTC ATGTACGATT AAAACGTTTT TACCCTTACC        60

TTTTCGTACT ACCTCTGCCT GAAGTTGACC ACCTTTAAAG TGATTCGTTG AAATCCATTA       120

TGCTCATTAT TAATACGATC TATAAAAACA AATGGAATGT GATGATCGAT GA              172
```

(2) INFORMATION FOR SEQ ID NO:22:

(i) SEQUENCE CHARACTERISTICS:
        (A) LENGTH: 155 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:22:

```
GTTCCATTGA CTCTGTATCA CCTGTTGTAA CGAACATCCA TATGTCCTGA AACTCCAACC        60

ACAGGTTTGA CCACTTCCAA TTTCAGACCA CCAAGTTTGA CACGTGAAGA TTCATCTTCT       120

AATATTTCGG AATTAATATC ATATTATTTA AATAG                                  155
```

(2) INFORMATION FOR SEQ ID NO:23:

(i) SEQUENCE CHARACTERISTICS:
        (A) LENGTH: 145 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:23:

```
ACATAGAAAA ACTCAAAAGA TTTACTTTTT TCAAATGGAA AATAAGGGTA CACACGATAT        60

TTCCCGTCAT CTTCAGTTAC CGGTACAACA TCCTCTTTAT TAACCTGCAC ATAATCTGAC       120

TCCGCTTCAC TCATCAAACT ACTAA                                             145
```

(2) INFORMATION FOR SEQ ID NO:24:

(i) SEQUENCE CHARACTERISTICS:
        (A) LENGTH: 266 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:24:

| | | | | | |
|---|---|---|---|---|---|
| TTTCACTGGA | ATTACATTTC | GCTCATTACG | TACAGTGACA | ATCGCGTCAG | ATAGTTTCTT | 60 |
| CTGGTTAGCT | TGACTCTTAA | CAATCTTGTC | TAAATTTTGT | TTAATTCTTT | GATTCGTACT | 120 |
| AGAAATTTTA | CTTCTAATTC | CTTGTAATTC | ATAACTTGCA | TTATCATATA | AATCATAAGT | 180 |
| ATCACATTTT | TGATGAATAC | TTTGATATAA | ATCTGACAAT | ACAGGCAGTT | GCTCCATTCT | 240 |
| ATCGTTAAGA | ATAGGGTAAT | TAATAG | | | | 266 |

(2) INFORMATION FOR SEQ ID NO:25:

(i) SEQUENCE CHARACTERISTICS:
        (A) LENGTH: 845 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:25:

| | | | | | |
|---|---|---|---|---|---|
| TGTTAAATTT | CTTTAACAGG | GATTTTGTTA | TTTAAATTAA | ACCTATTATT | TTGTCGCTTC | 60 |
| TTTCACTGCA | TCTACTGCTT | GAGTTGCTTT | TTCTGAAACC | GCCTCTTTCA | TTTCACTTGC | 120 |
| TTTTTCTGAT | GCTGCTTCTT | TCATTTCGCC | TACTTTTTCT | GACGCTGCTT | CTGTTGCTGA | 180 |
| TTTAATTACT | TCTTTCGCAT | CTTCCACTTT | CTCTGCTACT | TTATTTTTCA | CGTCTGTAGA | 240 |
| AAGCTGCTGT | GCTTTTTCCT | TTACTTCAGT | CATTGTATTA | GCTGCAGCAT | CTTTTGTTTC | 300 |
| TGATGCGACT | GATGCTACAG | TTTGCTTCGT | ATCCTCAACT | TTTTGTTTTG | CTTCTTGCTT | 360 |
| ATCAAAACAA | CCTGTCACGA | CTAAAGCTGA | ACCTAAAACC | AATGCTAATG | TTAATTTTTT | 420 |
| CATTATTTTC | TCCATAGAAT | AATTTGATTG | TTACAAAGCC | CTATTACTTT | GATGCAGTTT | 480 |
| AGTTTACGGG | AATTTTCATA | AAAAGAAAAA | CAGTAATAGT | AAAACTTTAC | CTTTCTTTAA | 540 |
| AAAGATTACT | TTATAAAAAA | ACATCTAAGA | TATTGATTTT | TAATAGATTA | TAAAAAACCA | 600 |
| ATAAAAATTT | TATTTTTTGT | AAAAAAAAAG | AATAGTTTAT | TTTAAATAAA | TTACAGGAGA | 660 |
| TGCTTGATGC | ATCAATATTT | CTGATTTATT | ACCATCCCAT | AATAATTGAG | CAATAGTTGC | 720 |
| AGGATAAAAT | GATATTGGAT | TTCGTTTTCC | ATACAGTTCA | GCAACAATTT | CTCCCACTAA | 780 |
| GGGCAAATGG | GAAACAATTA | ATACAGATTT | AACGCCCTCG | TCTTTTAGCA | CTTCTAAATA | 840 |
| ATCAA | | | | | | 845 |

(2) INFORMATION FOR SEQ ID NO:26:

(i) SEQUENCE CHARACTERISTICS:
        (A) LENGTH: 1598 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:26:

| | | | | | |
|---|---|---|---|---|---|
| GAATAGAGTT | GCACTCAATA | GATTCGGGCT | TTATAATTGC | CCAGATTTTT | ATTTATAACA | 60 |
| AAGGGTTCCA | AATGAAAAAA | TTTAATCAAT | CTCTATTAGC | AACTGCAATG | TTGTTGGCTG | 120 |
| CAGGTGGTGC | AAATGCGGCA | GCGTTTCAAT | TGGCGGAAGT | TTCTACTTCA | GGTCTTGGTC | 180 |

```
GTGCCTATGC GGGTGAAGCG GCGATTGCAG ATAATGCTTC TGTCGTGGCA ACTAACCCAG    240

CTTTGATGAG TTTATTTAAA ACGGCACAGT TTTCCACAGG TGGCGTTTAT ATTGATTCTA    300

GAATTAATAT GAATGGTGAT GTAACTTCTT ATGCTCAGAT AATAACAAAT CAGATTGGAA    360

TGAAAGCAAT AAAGGACGGC TCAGCTTCAC AGCGTAATGT TGTTCCCGGT GCTTTTGTGC    420

CAAATCTTTA TTTCGTTGCG CCAGTGAATG ATAAATTCGC GCTGGGTGCT GGAATGAATG    480

TCAATTTCGG TCTAAAAAGT GAATATGACG ATAGTTATGA TGCTGGTGTA TTTGGTGGAA    540

AAACTGACTT GAGTGCTATC AACTTAAATT TAAGTGGTGC TTATCGAGTA ACAGAAGGTT    600

TGAGCCTAGG TTTAGGGGTA AATGCGGTTT ATGCTAAAGC CCAAGTTGAA CGGAATGCTG    660

GTCTTATTGC GGATAGTGTT AAGGATAACC AAATAACAAG CGCACTCTCA ACACAGCAAG    720

AACCATTCAG AGATCTTAAG AAGTATTTGC CCTCTAAGGA CAAATCTGTT GTGTCATTAC    780

AAGATAGAGC CGCTTGGGGC TTTGGCTGGA ATGCAGGTGT AATGTATCAA TTAATGAAG    840

CTAACAGAAT TGGTTTAGCC TATCATTCTA AAGTGGACAT TGATTTTGCT GACCGCACTG    900

CTACTAGTTT AGAAGCAAAT GTCATCAAAG AAGGTAAAAA AGGTAATTTA ACCTTTACAT    960

TGCCAGATTA CTTAGAACTT TCTGGTTTCC ATCAATTAAC TGACAAACTT GCAGTGCATT   1020

ATAGTTATAA ATATACCCAT TGGAGTCGTT TAACAAAATT ACATGCCAGC TTCGAAGATG   1080

GTAAAAAAGC TTTTGATAAA GAATTACAAT ACAGTAATAA CTCTCGTGTT GCATTAGGGG   1140

CAAGTTATAA TCTTTATGAA AAATTGACCT TACGTGCGGG TATTGCTTAC GATCAAGCGG   1200

CATCTCGTCA TCACCGTAGT GCTGCAATTC AGATACCGA TCGCACTTGG TATAGTTTAG   1260

GTGCAACCTA TAAATTCACG CCGAATTTAT CTGTTGATCT TGGCTATGCT TACTTAAAAG   1320

GCAAAAAAGT TCACTTTAAA GAAGTAAAAA CAATAGGTGA CAAACGTACA TTGACATTGA   1380

ATACAACTGC AAATTATACT TCTCAAGCAC ACGCAAATCT TTACGGTTTG AATTTAAATT   1440

ATAGTTTCTA ATCCGTTAAA AAATTTAGCA TAATAAAGCA CAATTCCACA CTAAGTGTGC   1500

TTTTCTTTTA TAAAACAAGG CGAAAAATGA CCGCACTTTA TTACACTTAT TACCCCTCGC   1560

CAGTCGGACG GCTTTTGATT TTATCTGACG GCGAAACA                           1598
```

(2) INFORMATION FOR SEQ ID NO:27:

(i) SEQUENCE CHARACTERISTICS:
        (A) LENGTH: 9100 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:27:

```
GTCAAAAATT GCGTGCATTC TAGCGAAAAA ATGGGCTTTT GGGAACTGTG GGATTTATTT     60

AAAATCTTAG AAAATCTTAC CGCACTTTTA AGCTATAAAG TGCGGTGAAA TTTAGTGGCG    120

TTTATAATGG AGAATTACTC TGGTGTAATC CATTCGACTG TCCAGCTTCC AGTACCTTCT    180

GGAACTAATG TTTTTGTGAG ATAAGGCAAA ATTTCTTTCA TTTGGGTTTC TAATGTCCAA    240

GGTGGATTAA TTACCACCAT ACCGCTCGCA GTCATTCCTC GTTGATCGCT ATCTGGGCGA    300

ACGGCGAGTT CAATTTTTAG AATTTTTCTA ATTCCCGTTG CTTCTAAACC CTTAAAAATA    360

CGTTTAGTTT GTTGGCGTAA TACAACAGGA TACCAAATCG CATAAGTGCC AGTGGCAAAA    420

CGTTTATAGC CCTCTTCAAT GGCTTTAACA ACGAGATCAT AATCATCTTT TAATTCATAA    480
```

-continued

```
GGCGGATCGA TGAGTACTAA GCCTCGGCGT TCTTTTGGCG GAAGCGTTGC TTTGACTTGT    540

TGAAAGCCAT TGTCACATTT TACGGTGACA TTTTTGTCGT CGCTAAAATT ATTGCGAAGA    600

ATTGGATAAT CGCTAGGATG AAGCTCGGTC AATAGTGCGC GATCTTGTGA GCGCAACAAT    660

TCCGCGGCAA TTAATGGAGA ACCCGCGTAA TAACGTAGTT CTTTGCCACC ATAATTGAGT    720

TTTTTGATCA TTTTTACATA ACGAGCAATA TCTTCGGGTA AATCTGTTTG ATCCCACAGG    780

CGTCCAATAC CTTCTTTATA TTCCCCCGTT TTTTCTGATT CATTTGAGGA TAAACGATAA    840

CGCCCCACAC CAGAGTGCGT ATCCAAATAA AAAAAGCCTT TTTCTTTGAG TTAAGATTT     900

TCCAAAATGA GCATTAAAAC AATATGTTTC AAGACATCGG CATGATTGCC AGCGTGAAAT    960

GAGTGATGAT AACTCAGCAT AATATATTCC TTATATATTC CTTATTTGTT TAATAACGAA   1020

GGCGAGCCAA TTGACTCGCC CGATTACACA CTAAAGTGCG GTCATTTTTA GAAGAGTTCT   1080

TGTGGTTGCG TCGCTGGCGT ATTGCCTTCA TTATTTAAGC GTTGCTGTAA CTCAGTAGGA   1140

ACATAATAAC CACGCTCTTG CATTTCCGAA AGATAGGTAC GTGTCGGTTC TGTTCCCGCA   1200

ATAAAATATT CTTTGCGCCC ACCGTTTGGA GAAAGCAAAC CTGTCAAAGT ATCAATGTTT   1260

TTTTCCACAA TTTTTGGCGG TAGCGACAAT TTACGTTCTG GCTTATCACT CAAAGCCGTT   1320

TTCATATAAG TGATCCAAGC AGGCATTGCT GTTTTTGCTC CTGCTTCTCC ACGCCCAAGT   1380

ACTCGTTTGT TATCATCAAA CCCGACATAA GTTGTGGTTA CTAAGTTTGC ACCAAATCCC   1440

GCATACCAAG CCACTTTTGA ACTGTTGGTA GTACCTGTTT TACCGCCTAT ATCGCTACGT   1500

TTAATGCTTT GTGCAATACG CCAGCTGGTG CCTTTCCAGT CTAAACCTTG TTCGCCATAA   1560

ATTGCCGTAT TTAAGGCACT ACGAATGAGA AAAGCAAGTT CGCCACTAAT GACACGTGGC   1620

GCATATTCTA TTTTCGACGA AGCATTTTTT GCAGCAGCCA TTAAATCAAT CGCATCTTCT   1680

TTAAGTGCGG TCATATTTGA TTGTAATTCT GGCAGTTCAG GCACAGTTTC AGGTTGTTGA   1740

TCTAATTCTT CGCCATTGGT GCTGTCATCT GTTGGTTTTA AGGCATTCTC GCCTAAAGGA   1800

ATATTGGCAA AGCCGTTGAT TTTGTCTTTG GTTTCGCCAT AAATTACAGG TATATCATTA   1860

CATTCAATGC AAGCAATTTT AGGGTTTGCA ATAAATAAGT CTTTACCCGT GTTATCTTGA   1920

ATTTTTTCAA TGATATAAGG TTCAATGAGG AAGCCACCAT TATCAAACAC CGCATAAGCT   1980

CGCGCCATTT CTAATGGTGT GAAAGAGGCT GCGCCAAGTG CTAAGGCTTC ACTGGCAAAA   2040

TATTGATCAC GTTTAAAACC AAAACGTTGT AAAAATTCTG CTGTGAAATC AATACCTGCC   2100

GTTTGGATAG CACGAATAGC AATTATATTT TTGGATTGAC CTAATCCTAC GCGTAAACGC   2160

ATCGGGCCAT CATAACGATC AGGCGAGTTT TTCGGTTGCC ACATTTTTTG TCCCGGTTTT   2220

TGAATAGAAA TCGGGCTGTC TTGTAATACG CTTGAAAGTG TTAAGCCTTT TTCTAATGCT   2280

GCCGCGTAAA TAAATGGTTT GATAGAAGAA CCCACTTGAA CTAAAGACTG TGTGGCTCGA   2340

TTGAATTTAC TTTGTTCATA GCTAAAGCCA CCGACCACTG CTTCAATCGC ACCATTATCT   2400

GAATTAAGAG AAACTAATGC TGAATTTGCT GCGGGAATTT GTCCTAATTG CCATTCCCCA   2460

TTAGCACGCT GATGAATCCA AATTTGCTCG CCGACTTTCA CAGGATTGCT TCTGCCTGTC   2520

CAACGCATTG CATTGGTTGA TAAGGTCATT TTTTCCCCAG AAGCGAGCAA TATATCAGCA   2580

CCGCCTTTTA CAATTCCAAT CACTGCCGCA GGAATAAATG GCTCTGAATC AGGTAGTTTG   2640

CGTAGAAAAC CGACAATGCG ATCATTGTCC CAAGCGGCTT CATTTTTTTG CCATAATGGC   2700

GCGCCACCGC GATAACCGTG ACGCATATCG TAATCAATCA AGTTATTACG CACAGCTTTT   2760

TGGGCTTCAG CTTGGTCTTT TGAAAGTACA GTGGTAAATA CTTTATAACC ACTGGTGTAA   2820

GCATTTTCTT CGCCAAAACG ACGCACCATT TCTTGACGCA CCATTTCAGT GACATAATCG   2880
```

```
GCTCGAAATT CAAATTTTGC GCCGTGATAG CTCGCCACAA TCGGCTCTTT CAATGCAGCA    2940

TCATATTCTT CTTTGCTGAT GTATTTTCA TCTAACATAC GGCTTAGCAC CACATTGCGG     3000

CGTTCTTCTG AACGTTTTAA AGAATAAAGC GGGTTCATTG TTGAAGGTGC TTTAGGTAAA    3060

CCAGCAATAA TCGCCATTTC CGATAAGGTC AATTCATTCA ATGATTTACC GAAATAGGTT    3120

TGTGCTGCCG CTGCAACACC ATAAGAACGA TAGCCTAAAA AGATTTTGTT TAAATAAAGC    3180

TCTAATATTT CTTGTTTGTT GAGAGTATTT TCGATTTCTA CCGCAAGCAC GGCTTCACGA    3240

GCTTTACGAA TAATGGTTTT TTCTGAGGTT AAGAAAAAGT TACGCGCTAA TTGTTGAGTA    3300

ATCGTACTTG CGCCTTGTGA TGCACCGCCA TTACTCACTG CGACAAACAA TGCACGGGCA    3360

ATGCCGATAG GGTCTAATCC GTGATGATCG TAAAAACGAC TGTCTTCCGT CGCTAAAAAT    3420

GCGTCAATTA AGCGTTGTGG CACATCGGCT AATTTCACTG GAATACGGCG TTGCTCACCC    3480

ACTTCGCCAA TTAATTTACC GTCAGCCGTA TAAATCTGCA TTGGTTGCTG TAATTCAACG    3540

GTTTTTAATG TTTCTACTGA GGGCAATTCA GATTTTAAGT GGAAATACAA CATTCCGCCT    3600

GCTACTAAAC CTAAAATACA TAAAGTTAAT AGGGTGTTTA ATATTAATTT TGCGATCCGC    3660

ATCGTAAAAT TCTCGCTTCG TTAATGAATA TTCTTGTCAA GAGACCTATG ATTTGGCTGT    3720

TAAGTATAAA AGATTCAGCC TTTAAAGAAT AGGAAGAAT ATGCAATTCT CCCTGAAAAA     3780

TTACCGCACT TTACAAATCG GCATTCATCG TAAGCAGAGT TATTTTGATT TTGTGTGGTT    3840

TGATGATCTC GAACAGCCAC AAAGTTATCA AATCTTTGTT AATGATCGTT ATTTTAAAAA    3900

TCGTTTTTTA CAACAGCTAA AAACACAATA TCAAGGGAAA ACCTTTCCTT TGCAGTTTGT    3960

AGCAAGCATT CCCGCCCACT TAACTTGGTC GAAAGTATTA ATGTTGCCAC AAGTGTTAAA    4020

TGCGCAAGAA TGTCATCAAC AATGTAAATT TGTGATTGAA AAAGAGCTGC CTATTTTTTT    4080

AGAAGAATTG TGGTTTGATT ATCGTTCTAC CCCGTTAAAG CAAGGTTTTC GATTAGAGGT    4140

TACTGCAATT CGTAAAAGTA GCGCTCAAAC TTATTTGCAA GATTTCAGC CATTTAATAT     4200

TAATATATTG GATGTTGCGT CAAATGCTGT TTTGCGTGCA TTTCAATATC TGTTGAATGA    4260

ACAAGTGCGG TCAGAAAATA CCTTATTTTT ATTTCAAGAA GATGACTATT GCTTGGCGAT    4320

TTGTGAAAGA TCTCAGCAAT CACAAATTTT ACAATCTCAC GAAAATTTGA CCGCACTTTA    4380

TGAACAATTT ACCGAACGTT TTGAAGGACA ACTTGAACAA GTTTTTGTTT ATCAAATTCC    4440

CTCAAGTCAT ACACCATTAC CCGAAAACTG GCAGCGAGTA GAAACAGAAC TCCCTTTTAT    4500

TGCGCTGGGC AACGCGCTAT GGCAAAAAGA TTTACATCAA CAAAAAGTGG GTGGTTAAAT    4560

GTCGATGAAT TTATTGCCTT GGCGTACTTA TCAACATCAA AAGCGTTTAC GTCGTTTAGC    4620

TTTTTATATC GCTTTATTTA TCTTGCTTGC TATTAATTTA ATGTTGGCTT TTAGCAATTT    4680

GATTGAACAA CAGAAACAAA ATTTGCAGGC ACAGCAAAAG TCGTTTGAAC AACTTAATCA    4740

ACAGCTTCAT AAAACTACCA TGCAAATTGA TCAGTTACGC ATTGCGGTGA AGTTGGTGA    4800

AGTTTTGACA TCTATTCCCA ACGAGCAAGT AAAAAAGAGT TTACAACAGC TAAGTGAATT    4860

ACCTTTTCAA CAAGGAGAAC TGAATAAATT TAAACAAGAT GCCAATAACT TAAGCTTGGA    4920

AGGTAACGCG CAAGATCAAA CAGAATTTGA ACTGATTCAT CAATTTTTAA AGAAACATTT    4980

TCCCAATGTG AAATTAAGTC AGGTTCAACC TGAACAAGAT ACATTGTTTT TTCACTTTGA    5040

TGTGGAACAA GGGGCGGAAA AATGAAAGCT TTTTTTAACG ATCCTTTTAC TCCTTTTGGA    5100

AAATGGCTAA GTCAGCCTTT TTATGTGCAC GGTTTAACCT TTTTATTGCT ATTAAGTGCG    5160

GTGATTTTTC GCCCCGTTTT AGATTATATA GAGGGGAGTT CACGTTCCA TGAAATTGAA     5220

AATGAGTTAG CGGTGAAACG TTCAGAATTG TTGCATCAAC AGAAAATTTT AACCTCTTTA    5280
```

```
CAACAGCAGT CGGAAAGTCG AAAACTTTCT CCAGAACTGG CTGCACAAAT TATTCCTTTG      5340

AATAAACAAA TTCAACGTTT AGCTGCGCGT AACGGTTTAT CTCAGCATTT ACGTTGGGAA      5400

ATGGGGCAAA AGCCTATTTT GCATTTACAG CTTACAGGTC ATTTTGAAAA AACGAAGACA      5460

TTTTTATCCG CACTTTTGGC TAATTCGTCA CAGCTTTCTG TAAGTCGGTT GCAATTTATG      5520

AAACCCGAAG ACGGCCCATT GCAAACCGAG ATCATTTTTC AGCTAGATAA GGAAACAAAA      5580

TGAAACATTG GTTTTTCCTG ATTATATTAT TTTTTATGAA TTGCAGTTGG GGACAAGATC      5640

CTTTCGATAA AACACAGCGT AACCGTTCTC AGTTTGATAA CGCACAAACA GTAATGGAGC      5700

AAACAGAAAT AATTTCCTCA GATGTGCCTA ATAATCTATG CGGAGCGGAT GAAAATCGCC      5760

AAGCGGCTGA AATTCCTTTG AACGCTTTAA AATTGGTGGG GGTAGTGATT TCTAAAGATA      5820

AAGCCTTTGC CTTGTTGCAA GATCAAGGTT TGCAAGTTTA CAGCGTTTTA GAGGGCGTTG      5880

ATGTGGCTCA AGAGGGCTAT ATTGTAGAAA AAATCAACCA AAACAATGTT CAATTTATGC      5940

GTAAGCTAGG AGAGCAATGT GATAGTAGTG AATGGAAAAA ATTAAGTTTT TAAAGGAAGA      6000

TTATGAAGAA ATATTTTTTA AAGTGCGGTT ATTTTTTAGT ATGTTTTTGT TTGCCATTAA      6060

TCGTTTTTGC TAATCCTAAA ACAGATAACG AACGTTTTTT TATTCGTTTA TCGCAAGCAC      6120

CTTTAGCTCA AACACTGGAG CAATTAGCTT TTCAACAAGA TGTGAATTTA GTGATTGGAG      6180

ATATATTGGA AAACAAGATC TCTTTGAAAT TAAACAATAT TGATATGCCA CGTTTGCTAC      6240

AAATAATCGC AAAAAGTAAG CATCTTACTT TGAATAAAGA TGATGGGATT TATTATTTAA      6300

ACGGCAGTCA ATCTGGCAAA GGTCAGGTTG CAGGAAATCT TACGACAAAT GAACCGCACT      6360

TAGTGAGTCA CACGGTAAAA CTCCATTTTG CTAAAGCTTC TGAATTAATG AAATCCTTAA      6420

CAACAGGAAG TGGCTCTTTG CTTTCTCCCG CTGGGAGCAT TACCTTTGAT GATCGCAGTA      6480

ATTTGCTGGT TATTCAGGAT GAACCTCGTT CTGTGCAAAA TATCAAAAAA CTGATTGCTG      6540

AAATGGATAA GCCTATTGAA CAGATCGCTA TTGAAGCGCG AATTGTGACA ATTACGGATG      6600

AGAGTTTGAA AGAACTTGGC GTTCGGTGGG GGATTTTTAA TCCAACTGAA AATGCAAGAC      6660

GAGTTGCGGG CAGCCTTACA GGCAATAGCT TTGAAAATAT TGCGGATAAT CTTAATGTAA      6720

ATTTTGCGAC AACGACGACA CCTGCTGGCT CTATAGCATT ACAAGTCGCC AAAATTAATG      6780

GGCGATTGCT TGATTTAGAA TTGAGTGCGT TGGAGCGTGA AAATAATGTA GAAATTATTG      6840

CAAGCCCTCG CTTACTCACT ACCAATAAGA AAAGTGCGAG CATTAAACAG GGGACAGAAA      6900

TTCCTTACAT CGTGAGTAAT ACTCGTAACG ATACGCAATC TGTGGAATTT CGTGAGGCGG      6960

TGCTTGGTTT GGAAGTGACG CCACATATTT CTAAAGATAA CAATATCTTA CTTGATTTAT      7020

TGGTAAGTCA AAATTCCCCT GGTTCTCGTG TCGCTTATGG ACAAAATGAG GTGGTTTCTA      7080

TTGATAAACA AGAAATTAAT ACTCAGGTTT TTGCCAAAGA TGGGGAAACC ATTGTGCTTG      7140

GCGGCGTATT TCACGATACA ATCACGAAAA GCGAAGATAA AGTGCCATTG CTTGGCGATA      7200

TACCCGTTAT TAAACGATTA TTTAGCAAAG AAAGTGAACG ACATCAAAAA CGTGAGCTAG      7260

TGATTTTCGT CACGCCACAT ATTTTAAAAG CAGGAGAAAA CGTTAGAGGC GTTGAAACAA      7320

AAAAGTGAGG GTAAAAAATA ACTTTTTAAA TGATGAATTT TTTAATTTT CGCTGTATCC      7380

ACTGTCGTGG CAATCTTCAT ATCGCAAAAA ATGGGTTATG TTCAGGTTGC CAAAAACAAA      7440

TTAAATCTTT TCCTTATTGC GGTCATTGTG GTTCGGAATT GCAATATTAT GCGCAGCATT      7500

GTGGGAATTG TCTTAAACAA GAACCAAGTT GGGATAAGAT GGTCATTATT GGGCATTATA      7560

TTGAACCTCT TTCGATATTG ATTCAGCGTT TTAAATTTCA AAATCAATTT TGGATTGACC      7620

GCACTTTAGC TCGGCTTTTA TATCTTGCGG TACGTGATGC TAAACGAACG CATCAACTTA      7680
```

```
AATTGCCAGA GGCAATCATT CCAGTGCCTT TATATCATTT TCGTCAGTGG CGACGGGGTT    7740

ATAATCAGGC AGATTTATTA TCTCAGCAAT TAAGTCGTTG GCTGGATATT CCTAATTTGA    7800

ACAATATCGT AAAGCGTGTG AAACACACCT ATACTCAACG TGGTTTGAGT GCAAAAGATC    7860

GTCGTCAGAA TTTAAAAAAT GCCTTTTCTC TTGCTGTTTC GAAAAATGAA TTTCCTTATC    7920

GTCGTGTTGC GTTGGTGGAT GATGTGATTA CTACTGGTTC TACACTCAAT GAAATCTCAA    7980

AATTGTTGCG AAAATTAGGT GTGGAGGAGA TTCAAGTGTG GGGGCTGGCA CGAGCTTAAT    8040

ATAAAGCACT GGAAAAAAAA GCGCGATAAG CGTATTATTC CCGATACTTT CTCTCAAGTA    8100

TTTAGGACAT AATTATGGAA CAAGCAACCC AGCAAATCGC TATTTCTGAT GCCGCACAAG    8160

CGCATTTTCG AAAACTTTTA GACACCCAAG AAGAAGGAAC GCATATTCGT ATTTTCGCGG    8220

TTAATCCTGG TACGCCTAAT GCGGAATGTG GCGTATCTTA TTGCCCCCCG AATGCCGTGG    8280

AAGAAAGCGA TATTGAAATG AAATATAATA CTTTTTCTGC ATTTATTGAT GAAGTGAGTT    8340

TGCCTTTCTT AGAAGAAGCA GAAATTGATT ATGTTACCGA AGAGCTTGGT GCGCAACTGA    8400

CCTTAAAAGC ACCGAATGCC AAAATGCGTA AGGTGGCTGA TGATGCGCCA TTGATTGAAC    8460

GTGTTGAATA TGTAATTCAA ACTCAAATTA ACCCACAGCT TGCAAATCAC GGTGGACGTA    8520

TAACCTTAAT TGAAATTACT GAAGATGGTT ACGCAGTTTT ACAATTTGGT GGTGGCTGTA    8580

ACGGTTGTTC AATGGTGGAT GTTACGTTAA AAGATGGGGT AGAAAAACAA CTTGTTAGCT    8640

TATTCCCGAA TGAATTAAAA GGTGCAAAAG ATATAACTGA GCATCAACGT GGCGAACATT    8700

CTTATTATTA GTGAGTTATA AAAGAAGATT TATAATGACC GCACTTTTGA AAGTGCGGTT    8760

ATTTTTATGG AGAAAAAATG AAAATACTTC AACAAGATGA TTTTGGTTAT TGGTTGCTTA    8820

CACAAGGTTC TAATCTGTAT TTAGTGAATA ATGAATTGCC TTTTGGTATC GCTAAAGATA    8880

TTGATTTGGA AGGATTGCAG GCAATGCAAA TTGGGGAATG GAAAAATTAT CCGTTGTGGC    8940

TTGTGGCTGA GCAAGAAAGT GATGAACGAG AATATGTGAG TTTGAGTAAC TTGCTTTCAC    9000

TGCCAGAGGA TGAATTCCAT ATATTAAGCC GAGGTGTGGA AATTAATCAT TTTCTGAAAA    9060

CCCATAAATT CTGTGGAAAG TGCGGTCATA AAACACAACA                         9100

(2) INFORMATION FOR SEQ ID NO:28:

(i) SEQUENCE CHARACTERISTICS:
        (A) LENGTH: 525 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:28:

AAAAATCGAC TGCCGTCATT TTCAACCACC ACATAGCTCA TATTCGCAAG CCAATGTATT      60

GACCGTTGGG AATAATAACA GCCCCAAAAC AATGAAACAT ATGGTGATGA GCCAAACATA     120

CTTTCCTGCA GATTTTGGAA TCATATCGCC ATCAGCACCA GTATGGTTTG ACCAGTATTT     180

AACGCCATAG ACATGTGTAA AAAAATTAAA TAACGGTGCA AGCATGAGAC CAACGGCACC     240

TGATGTACCT TGTACGATGA CCTCACCTGC TGTGGCAACA ATACCAAGTC CATTGCCTGT     300

GATATTTTTG CGAAAAGACA AACTTACCAC ACAGACCAAG CCGATGATTG AGATGACAAA     360

ATAAAACCAA TCCAAATGCG TGTGAGCTGT TGTGGTCCAA AATCCAGTAA ATAGTGCAAT     420

AAATCCGCAA ACAAACCAAA GTAGCACCCA GCTTGTTGTC CAATCTTTTT TACCAAAGCC     480
```

TGTGATGTTA TCTAAAATAT CAATTTTCAT CAGATTTTCC CTAAT     525

(2) INFORMATION FOR SEQ ID NO:29:

(i) SEQUENCE CHARACTERISTICS:
        (A) LENGTH: 466 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:29:

TAATGATAAC CAGTCAAGCA AGCTCAAATC AGGGTCAGCC TGTTTTGAGC TTTTTATTTT     60

TTGATCATCA TGCTTAAGAT TCACTCTGCC ATTTTTTTAC AACCTGCACC ACAAGTCATC    120

ATCGCATTTG CAAAAATGGT ACAAACAAGC CGTCAGCGAC TTAAACAAAA AAAGGCTCAA    180

TCTGCGTGTG TGCGTTCACT TTTACAAATC ACCATGCACC GCTTTGACAT TGTTGGTGAA    240

TTTCATGACC ATGCACACCC TTATTATATT AACTCAAATA AAATACGCTA CTTTGTCAGC    300

TTTAGCCATT CAGATAATCA AGTCGCTCTC ATCATCAGCT TAACACCTTG TGCCATTGAC    360

ATAGAAGTTA ACGATATTAA ATACAGTGTG GTTGAACGAT ACTTTCATCC CAATGAAATT    420

TATCTACTTA CTCAATTTAG CTCTACTGAT AGGCAACAGC TTATTA                  466

(2) INFORMATION FOR SEQ ID NO:30:

(i) SEQUENCE CHARACTERISTICS:
        (A) LENGTH: 631 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:30:

GATCTTTGAT TTTCATTGAG TATTACTCTC TCTTGTCACT TCTTTCTATT TTACCATAAA     60

GTCCAGCCTT TGAAGAACTT TTACTAGAAG ACAAGGGGCT TCTGTCTCTA TTTGCCATCT    120

TAGGCATCAA AAAAGAGGGG TCATCCCTCT TTACGAATTC AATGCTACTA GGGTATCCAA    180

ATACTGGTTG TTGATGACTG CCAAAATATA GGTATCTGCT TTCAAGAGGT CATCTGGTCC    240

AAATTCAACA TCCAATGGGG AATTTTCCTG CTCTCGGAAA CCCAAAATAT TCAGATTGTA    300

TTTGCCACGG AGGTCTAATT TACTTCAGAC TTTGACCTGC CCAAGACTGA GGAATTTTCA    360

TCTCCACGAT AGACACATTT TTATCCAACT GAAAGACATC AACACTATTA TGAAAAGAAT    420

GGTCTGTGCT AGAGACTGCC CCATTTCATA CTCTGGCGAG ATAACCGAGT CAGCTCCAAT    480

CTTTTCTAGC ACTTTCTTAG CGGTCTGACT TTTGACCTTA GCAATAACAG TCGGTACCCC    540

CAAACTCTTA CAGTGCATAA CCGCAAGCAC ACTCGACTCC AGATTTTCAC CTGTCGCGAC    600

TACAACGGTA TCGCAGGTAT CAATCCCTGC T                                   631

(2) INFORMATION FOR SEQ ID NO:31:

(i) SEQUENCE CHARACTERISTICS:
        (A) LENGTH: 3754 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
    (A) ORGANISM: Streptococcus pneumoniae (xi) SEQUENCE DESCRIPTION: SEQ ID NO:31:

| | | | | | |
|---|---|---|---|---|---|
| CCAATATTTT | GGTCAGCATA | GTGTTCTTTT | TCAGTGGTAA | CAGCTTGCAA | TACTTGAGCA | 60 |
| GAAATGGCAG | ATTTATCAAG | GAAAAGTTA | ACGTAAGGTC | CTGTTGCGAC | AACTTTTTCA | 120 |
| AAGGCTTGGC | TGTTCATTTT | TTCAGCCAGT | TCAGCCGCAA | TCATTTGTGG | TGCTTTACGT | 180 |
| TCGACTTTTG | CAAGAGAAAA | AGCAGGGAAA | GCAATGTCTC | CCATTTCTGA | GTTTTTAGGG | 240 |
| GTTTCCAGTA | ACTTTAAAAT | AGCCTCTTGG | TCCAGGCTAT | CAATGATGCT | AGATAATTCG | 300 |
| CTAGCAATCA | ATTCTTTTGT | ATTCATTAAG | AGCTCCTTTT | TGGACTTTTC | TACTATTTTA | 360 |
| TCACAATTTT | AAAGAAAGAA | GAAAAAATTT | TTGAAATCTC | CTGTTTTTTT | GGTATAATAT | 420 |
| GGTTATAAAT | ATAGTTATAA | ATATAGTTAT | AAATATGCAC | GCAAGAGGAT | TTTATGAGAA | 480 |
| AAAGAGATCG | TCATCAGTTA | ATAAAAAAAA | TGATTACTGA | GGAGAAATTA | AGTACACAAA | 540 |
| AAGAAATTCA | AGATCGGTTG | GAGGCGCACA | ATGTTTGTGT | GACGCAGACA | ACCTTGTCTC | 600 |
| GTGATTTGCG | CGAAATCGGC | TTGACCAAGG | TCAAGAAAAA | TGATATGGTG | TATTATGTAC | 660 |
| TAGTAAATGA | GACAGAAAAG | ATTGATTTGG | TGGAATTTTT | GTCTCATCAT | TTAGAAGGTG | 720 |
| TTGCAAGAGC | AGAGTTTACC | TTGGTGCTTC | ATACCAAATT | GGGAGAAGCC | TCTGTTTTGG | 780 |
| CAAATATTGT | AGATGTAAAC | AAGGATGAAT | GGATTTTAGG | AACAGTTGCT | GGTGCCAATA | 840 |
| CCTTATTGGT | TATTTGTCGA | GATCAGCACG | TTGCCAAACT | CATGGAAGAT | CGTTTGCTAG | 900 |
| ATTTGATGAA | AGATAAGTAA | GGTCTTGGGA | GTTGCTCTCA | AGACTTATTT | TTGAAAAGGA | 960 |
| GAGACAGAAA | ATGGCGATAG | AAAAGCTATC | ACCCGGCATG | CAACAGTATG | TGGATATTAA | 1020 |
| AAAGCAATAT | CCAGATGCTT | TTTTGCTCTT | TCGGATGGGT | GATTTTTATG | AATTATTTTA | 1080 |
| TGAGGATGCG | GTCAATGCTG | CGCAGATTCT | GGAAATTTCC | TTAACGAGTC | GCAACAAGAA | 1140 |
| TGCCGACAAT | CCGATCCCTA | TGGCGGGTGT | TCCCTATCAT | TCTGCCCAAC | AGTATATCGA | 1200 |
| TGTCTTGATT | GAGCAGGGTT | ATAAGGTGGC | TATCGCAGAG | CAGATGGAAG | ATCCTAAACA | 1260 |
| AGCAGTTGGG | GTTGTTAAAC | GAGAGGTTGT | TCAGGTCATT | ACGCCAGGGA | CAGTGGTCGA | 1320 |
| TAGCAGTAAG | CCGGACAGTC | AGAATAATTT | TTTGGTTTCC | ATAGACCGCG | AAGGCAATCA | 1380 |
| ATTTGGCCTA | GCTATATATGG | ATTTGGTGAC | GGGTGACTTT | TATGTGACAG | GTCTTTTGGA | 1440 |
| TTTCACGCTG | GTTTGTGGGG | AAATCCGTAA | CCTCAAGGCT | CGAGAAGTGG | TGTTGGGTTA | 1500 |
| TGACTTGTCT | GAGGAAGAAG | AACAAATCCT | CAGCCGCCAG | ATGAATCTGG | TACTCTCTTA | 1560 |
| TGAAAAAGAA | AGCTTTGAAG | ACCTTCATTT | ATTGGATTTG | CGATTGGCAA | CGGTGGAGCA | 1620 |
| AACGGCATCT | AGTAAGCTGC | TCCAGTATGT | TCATCGGACT | CAGATGAGGG | AATTGAACCA | 1680 |
| CCTCAAACCT | GTTATCCGCT | ACGAAATTAA | GGATTTCTTG | CAGATGGATT | ATGCGACCAA | 1740 |
| GGCTAGTCTG | GATTTGGTTG | AGAATGCTCG | CTCAGGTAAG | AAACAAGGCA | GTCTTTTCTG | 1800 |
| GCTTTTGGAT | GAAACCAAAA | CGGCTATGGG | GATGCGTCTC | TTGCGTTCTT | GGATTCATCG | 1860 |
| CCCCTTGATT | GATAAGGAAC | GAATCGTCCA | ACGTCAAGAA | GTAGTGCAGG | TCTTTCTCGA | 1920 |
| CCATTTCTTT | GAGCGTAGTG | ACTTGACAGA | CAGTCTCAAG | GGTGTTTATG | ACATTGAGCG | 1980 |
| CTTGGCTAGT | CGTGTTTCTT | TTGGCAAAAC | CAATCCAAAG | GATCTCTTGC | AGTTGGCGAC | 2040 |
| TACCTTGTCT | AGTGTGCCAC | GGATTCGTGC | GATTTTAGAA | GGGATGGAGC | AACCTACTCT | 2100 |
| AGCCTATCTC | ATCGCACAAC | TGGATGCAAT | CCCTGAGTTG | GAGAGTTTGA | TTAGCGCAGC | 2160 |

```
GATTGCTCCT GAAGCTCCTC ATGTGATTAC AGATGGGGGA ATTATCCGGA CTGGATTTGA     2220

TGAGACTTTA GACAAGTATC GTTGCGTTCT CAGAGAAGGG ACTAGCTGGA TTGCTGAGAT     2280

TGAGGCTAAG GAGCGAGAAA ACTCTGGTAT CAGCACGCTC AAGATTGACT ACAATAAAAA     2340

GGATGGCTAC TATTTTCATG TGACCAATTC GCAACTGGGA AATGTGCCAG CCCACTTTTT     2400

CCGCAAGGCG ACGCTGAAAA ACTCAGAACG CTTTGGAACC GAAGAATTAG CCCGTATCGA     2460

GGGAGATATG CTTGAGGCGC GTGAGAAGTC AGCCAACCTC GAATACGAAA TATTTATGCG     2520

CATTCGTGAA GAGGTCGGCA AGTACATCCA GCGTTTACAA GCTCTAGCCC AAGGAATTGC     2580

GACGGTTGAT GTCTTACAGA GTCTGGCGGT TGTGGCTGAA ACCCAGCATT TGATTCGACC     2640

TGAGTTTGGT GACGATTCAC AAATTGATAT CCGGAAAGGG CGCCATGCTG TCGTTGAAAA     2700

GGTTATGGGG GCTCAGACCT ATATTCCAAA TACGATTCAG ATGGCAGAAG ATACCAGTAT     2760

TCAATTGGTT ACAGGGCCAA ACATGAGTGG GAAGTCTACC TATATGCGTC AGTTAGCCAT     2820

GACGGCGGTT ATGGCCCAGC TGGGTTCCTA TGTTCCTGCT GAAAGCGCCC ATTTACCGAT     2880

TTTTGATGCG ATTTTTACCC GTATCGGAGC AGCAGATGAC TTGGTTTCGG GTCAGTCAAC     2940

CTTTATGGTG GAGATGATGG AGGCCAATAA TGCCATTTCG CATGCGACCA AGAACTCTCT     3000

CATTCTCTTT GATGAATTGG GACGTGGAAC TGCAACTTAT GACGGGATGG CTCTTGCTCA     3060

GTCCATCATC GAATATATCC ATGAGCACAT CGGAGCTAAG ACCCTCTTTG CGACCCACTA     3120

CCATGAGTTG ACTAGTCTGG AGTCTAGTTT ACAACACTTG GTCAATGTCC ACGTGGCAAC     3180

TTTGGAGCAG GATGGGCAGG TCACCTTCCT TCACAAGATT GAACCGGGAC CAGCTGATAA     3240

ATCCTACGGT ATCCATGTTG CCAAGATTGC TGGCTTGCCA GCAGACCTTT TAGCAAGGGC     3300

GGATAAGATT TTGACTCAGC TAGAGAATCA AGGAACAGAG AGTCCTCCTC CCATGAGACA     3360

AACTAGTGCT GTCACTGAAC AGATTTCACT CTTTGATAGG GCAGAAGAGC ATCCTATCCT     3420

AGCAGAATTA GCTAAACTGG ATGTGTATAA TATGACACCT ATGCAGGTTA TGAATGTCTT     3480

AGTAGAGTTA AAACAGAAAC TATAAAACCA AGACTCACTA GTTAATCTAG CTGTATCAAG     3540

GAGACTTCTT TGACAATTCT CCACTTTTTT GCTAGAATAA CATCACACAA ACAGAATGAA     3600

AAGGGCTGAC GCATTGTCGC TCCCTTTTGT CTATTTTTTA AGGAGAAAGT ATGCTGATTC     3660

AGAAAATAAA AACCTACAAG TGGCAGGCCC TGCTTCGCTC CTGATGACAG GCTTGATGGT     3720

TGCTAGTTCA CTTCTGCAAC CGCGTTATCT GCAG                                3754
```

(2) INFORMATION FOR SEQ ID NO:32:

(i) SEQUENCE CHARACTERISTICS:
        (A) LENGTH: 1337 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:32:

```
AACAAAATAA AAGAACTTAC CTATTTTCCA TCCAAAATGT TTAGCAATCA TCATCTGCAA      60

GGCAACGTAT TGCATGGCAT TGATGTGATG AGCAACTAAT ATGTCATTAG AACGTTGCGT     120

CAAACTAGCA TCTAAATAAA GATCGAAATG CAGTTATCAA AAATGCAAGC TCCTATCGGC     180

CCTTGTTTTA ATTATTACTC ACATTGCCTT AATGTATTTA CTTGCTTATT ATTAACTTTT     240

TTGCTAAGTT AGTAGCGTCA GTTATTCATT GAAAGGACAT TATTATGAAA ATTCTTGTAA     300
```

| | |
|---|---|
| CAGGCTTTGA TCCCTTTGGC GGCGAAGCTA TTAATCCTGC CCTTGAAGCT ATCAAGAAAT | 360 |
| TGCCAGCAAC CATTCATGGA GCAGAAATCA AATGTATTGA AGTTCCAACG GTTTTTCAAA | 420 |
| AATCTGCCGA TGTGCTCCAG CAGCATATCG AAAGCTTTCA ACCTGATGCA GTCCTTTGTA | 480 |
| TTGGGCAAGC TGGTGGCCGG ACTGGACTAA CGCCAGAACG CGTTGCCATT AATCAAGACG | 540 |
| ATGCTCGCAT TCCTGATAAC GAAGGGAATC AGCCTATTGA TACACCTATT CGTGCAGATG | 600 |
| GTAAAGCAGC TTATTTTTCA ACCTTGCCAA TCAAAGCGAT GGTTGCTGCC ATTCATCAGG | 660 |
| CTGGGCTTCC TGCTTCTGTT TCTAATACAG CTGGTACCTT TGTTTGCAAT CATTTGATGT | 720 |
| ATCAAGCCCT TTACTTAGTG GATAAATATT GTCCAAATGC CAAAGCTGGG TTTATGCATA | 780 |
| TTCCCTTTAT GATGGAACAG GTTGTTGATA AACCTAATAC AGCTGCCATG AACCTCGATG | 840 |
| ATATTACAAG AGGAATTGAG GCTGCTATTT TTGCCATTGT CGATTTCAAA GATCGTTCCG | 900 |
| ATTTAAAACG TGTAGGGGGC GCTACTCACT GACTGTGACG CTACTAAACC TATTTTAAAA | 960 |
| AAACAGAGAT ATGAACTAAC TCTGTTTTTT TTGTGCTAAA AATGAAAGAC CTAGGGAAAC | 1020 |
| TTTTCATCGG TCTTTCTCAA TTGTCATCTT AATCTAATAC TACTTCTAAC ATCAGCGGGT | 1080 |
| ATAGTTTGCC AGTAATTAAG AAACGTTGTT GATCTAAATG AGCAATCCCA TTCAAAACAT | 1140 |
| TAAGGTCAGG GTAATGGGAC TTATCAAGAT TTAAGGCTTT TAACAAAGGA CTAATATCAT | 1200 |
| AGGTGGCTAC CACCTTTCCA GAATCAGGTT GGAGTTTGAC AATAGTATTG GTTTGCCAAA | 1260 |
| TATTGGCATA GAGATAACCA TCTACATACT CTAATTCGTT AAGCATTGAG ATAGGGACAC | 1320 |
| TTTCTATAGC AACTAGT | 1337 |

(2) INFORMATION FOR SEQ ID NO:33:

(i) SEQUENCE CHARACTERISTICS:
        (A) LENGTH: 1837 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:33:

| | |
|---|---|
| TCATGTTTGA CAGCTTATCA TCGATAAGCT TACTTTTCGA ATCAGGTCTA TCCTTGAAAC | 60 |
| AGGTGCAACA TAGATTAGGG CATGGAGATT TACCAGACAA CTATGAACGT ATATACTCAC | 120 |
| ATCACGCAAT CGGCAATTGA TGACATTGGA ACTAAATTCA ATCAATTTGT TACTAACAAG | 180 |
| CAACTAGATT GACAACTAAT TCTCAACAAA CGTTAATTTA ACAACATTCA AGTAACTCCC | 240 |
| ACCAGCTCCA TCAATGCTTA CCGTAAGTAA TCATAACTTA CTAAAACCTT GTTACATCAA | 300 |
| GGTTTTTTCT TTTTGTCTTG TTCATGAGTT ACCATAACTT TCTATATTAT TGACAACTAA | 360 |
| ATTGACAACT CTTCAATTAT TTTTCTGTCT ACTCAAAGTT TTCTTCATTT GATATAGTCT | 420 |
| AATTCCACCA TCACTTCTTC CACTCTCTCT ACCGTCACAA CTTCATCATC TCTCACTTTT | 480 |
| TCGTGTGGTA ACACATAATC AAATATCTTT CCGTTTTTAC GCACTATCGC TACTGTGTCA | 540 |
| CCTAAAATAT ACCCCTTATC AATCGCTTCT TTAAACTCAT CTATATATAA CATATTTCAT | 600 |
| CCTCCTACCT ATCTATTCGT AAAAAGATAA AAATAACTAT TGTTTTTTTT GTTATTTTAT | 660 |
| AATAAAAATTA TTAATATAAG TTAATGTTTT TTAAAAATAT ACAATTTTAT TCTATTTATA | 720 |
| GTTAGCTATT TTTTCATTGT TAGTAATATT GGTGAATTGT AATAACCTTT TTAAATCTAG | 780 |
| AGGAGAACCC AGATATAAAA TGGAGGAATA TTAATGGAAA ACAATAAAAA AGTATTGAAG | 840 |

```
AAAATGGTAT TTTTTGTTTT AGTGACATTT CTTGGACTAA CAATCTCGCA AGAGGTATTT    900

GCTCAACAAG ACCCCGATCC AAGCCAACTT CACAGATCTA GTTTAGTTAA AAACCTTCAA    960

AATATATATT TTCTTTATGA GGGTGACCCT GTTACTCACG AGAATGTGAA ATCTGTTGAT   1020

CAACTTTTAT CTCACGATTT AATATATAAT GTTTCAGGGC CAAATTATGA TAAATTAAAA   1080

ACTGAACTTA AGAACCAAGA GATGGCAACT TTATTTAAGG ATAAAAACGT TGATATTTAT   1140

GGTGTAGAAT ATTACCATCT CTGTTATTTA TGTGAAAATG CAGAAAGGAG TGCATGTATC   1200

TACGGAGGGG TAACAAATCA TGAAGGGAAT CATTTAGAAA TTCCTAAAAA GATAGTCGTT   1260

AAAGTATCAA TCGATGGTAT CCAAAGCCTA TCATTTGATA TTGAAACAAA TAAAAAAATG   1320

GTAACTGCTC AAGAATTAGA CTATAAAGTT AGAAAATATC TTACAGATAA TAAGCAACTA   1380

TATACTAATG GACCTTCTAA ATATGAAACT GGATATATAA AGTTCATACC TAAGAATAAA   1440

GAAAGTTTTT GGTTTGATTT TTTCCCTGAA CCAGAATTTA CTCAATCTAA ATATCTTATG   1500

ATATATAAAG ATAATGAAAC GCTTGACTCA AACACAAGCC AAATTGAAGT CTACCTAACA   1560

ACCAAGTAAC TTTTTGCTTT TGGCAACCTT ACCTACTGCT GGATTTAGAA ATTTTATTGC   1620

AATTCTTTTA TTAATGTAAA AACCGCTCAT TTGATGAGCG GTTTTGTCTT ATCTAAAGGA   1680

GCTTTACCTC CTAATGCTGC AAAATTTTAA ATGTTGGATT TTTGTATTTG TCTATTGTAT   1740

TTGATGGGTA ATCCCATTTT TCGACAGACA TCGTCGTGCC ACCTCTAACA CCAAAATCAT   1800

AGACAGGAGC TTGTAGCTTA GCAACTATTT TATCGTC                            1837

(2) INFORMATION FOR SEQ ID NO:34:

(i) SEQUENCE CHARACTERISTICS:
        (A) LENGTH: 841 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Streptococcus pneumoniae (xi) SEQUENCE DESCRIPTION: SEQ ID NO:34:

GATCAATATG TCCAAGAAAC CACATGTTCC TAAGACAAGA GCTAACAGAC TGGCCGTCAA     60

TAATAGTATT GTTCTTTTTT TCATCATTAC TCCTTAACTA GTGTTTAACT GATTAATTAG    120

CCAGTAAATA GTTTATCTTT ATTTACACTA TCTGTTAAGA TATAGTAAAA TGAAATAAGA    180

ACAGGACAGT CAAATCGATT TCTAACAATG TTTTAGAAGT AGAGGTATAC TATTCTAATT    240

TCAATCTACT ATATTTTGCA CATTTTCATA AAAAAAATGA GAACTAGAAC TCACATTCTG    300

CTCTCATTTT TCGTTTTCCC GTTCTCCTAT CCTGTTTTTA GGAGTTAGAA AATGCTGCTA    360

CCTTTACTTA CTCTCCTTTA ATAAAGCCAA TAGTTTTTCA GCTTCTGCCA TAATAGTATT    420

GTTGTCCTGG GTGCCAAATA GTAAATTATT TTTTAATCCT GTGAGAGTCT CTTTGGCATT    480

GGACTTGATA ATTGGATTCT GGATTTTTCC AAGTAAATCT TCAGCCTCTC TCAGTTTTCT    540

TAACCTTTCA GTCTCGACCT GAGGTTCTTC TGATTCCTCT GGTGATTCTT CTGGTGATTC    600

TTCTTCTGGT TCCTCTGTTG GTTTTGGAGA CTCTGGTTTC TCGCTTTGCG GTTTCTCTTC    660

TCGAGGGGTT TCTTCCTCAG GTTTTTCTGT CTGAGGTTTC TCCTCGTTTG GTTTTTCCGT    720

TTGATTGGTA TCAGCTTGAC CATTTTTGTT TCTTTGAACA TGGTCGCTAG CGTTACCAAA    780

ACCATTATCT GAATGCGACG TTCGTTTGGA TGTTCGACAT AGTACTTGAC AGTCGCCAAA    840

A                                                                   841
```

(2) INFORMATION FOR SEQ ID NO:35:

(i) SEQUENCE CHARACTERISTICS:
        (A) LENGTH: 4500 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:35:

```
GATCAGGACA GTCAAATCGA TTTCTAACAA TGTTTTAGAA GTAGATGTGT ACTATTCTAG      60

TTTCAATCTA TTATATTTAT AGAATTTTTT GTTGCTAGAT TTGTCAAATT GCTTAAAATA     120

ATTTTTTTCA GAAAGCAAAA GCCGATACCT ATCGAGTAGG GTAGTTCTTG CTATCGTCAG     180

GCTTGTCTGT AGGTGTTAAC ACTTTTCAAA AATCTCTTCA AACAACGTCA GCTTTGCCTT     240

GCCGTATATA TGTTACTGAC TTCGTCAGTT CTATCTGCCA CCTCAAAACG GTGTTTTGAG     300

CTGACTTCGT CAGTTCTATC CACAACCTCA AAACAGTGTT TGAGCTGAC TTCGTCAGTT      360

CTATCCACAA CCTCAAAACA GTGTTTTGAG CTGACTTTGT CAGTCTTATC TACAACCTCA     420

AAACAGTGTT TGAGCATCA TGCGGCTAGC TTCTTAGTTT GCTCTTTGAT TTTCATTGAG      480

TATAAAAACA GATGAGTTTC TGTTTTCTTT TTATGGACTA TAAATGTTCA GCTGAAACTA     540

CTTTCAAGGA CATTATTATA TAAAAGAATT TTTTGAAACT AAAATCTACT ATATTACACT     600

ATATTGAAAG CGTTTTAAAA ATGAGGTATA ATAAATTTAC TAACACTTAT AAAAAGTGAT     660

AGAATCTATC TTTATGTATA TTTAAAGATA GATTGCTGTA AAAATAGTAG TAGCTATGCG     720

AAATAACAGA TAGAGAGAAG GGATTGAAGC TTAGAAAAGG GGAATAATAT GATATTTAAG     780

GCATTCAAGA CAAAAAGCA GAGAAAAGA CAAGTTGAAC TACTTTTGAC AGTTTTTTTC       840

GACAGTTTTC TGATTGATTT ATTTCTTCAC TTATTTGGGA TTGTCCCCTT TAAGCTGGAT     900

AAGATTCTGA TTGTGAGCTT GATTATATTT CCCATTATTT CTACAAGTAT TTATGCTTAT     960

GAAAAGCTAT TTGAAAAAGT GTTCGATAAG GATTGAGCAG GAAGTATGGT GTAAATAGCA    1020

TAAGCTGATG TCCATCATTT GCTTATAAAG AGATATTTTA GTTTAATTGC AGCGGTGTCC    1080

TGGTAGATAA ACTAGATTGG CAGGAGTCTG ATTGGAGAAA GGAGAGGGGA AATTTGGCAC    1140

CAATTTGAGA TAGTTTGTTT AGTTCATTTT TGTCATTTAA ATGAACTGTA GTAAAAGAAA    1200

GTTAATAAAA GACAAACTAA GTGCATTTTC TGGAATAAAT GTCTTATTTC AGAAATCGGG    1260

ATATAGATAT AGAGAGGAAC AGTATGAATC GGAGTGTTCA AGAACGTAAG TGTCGTTATA    1320

GCATTAGGAA ACTATCGGTA GGAGCGGTTT CTATGATTGT AGGAGCAGTG GTATTTGGAA    1380

CGTCTCCTGT TTTAGCTCAA GAAGGGGCAA GTGAGCAACC TCTGGCAAAT GAAACTCAAC    1440

TTTCGGGGGA GAGCTCAACC CTAACTGATA CAGAAAAGAG CCAGCCTTCT TCAGAGACTG    1500

AACTTTCTGG CAATAAGCAA GAACAAGAAA GGAAAGATAA GCAAGAAGAA AAATTCCAA     1560

GAGATTACTA TGCACGAGAT TTGGAAAATG TCGAAACAGT GATAGAAAAA GAAGATGTTG    1620

AAACCAATGC TTCAAATGGT CAGAGAGTTG ATTTATCAAG TGAACTAGAT AAACTAAAGA    1680

AACTTGAAAA CGCAACAGTT CACATGGAGT TTAAGCCAGA TGCCAAGGCC CCAGCATTCT    1740

ATAATCTCTT TTCTGTGTCA AGTGCTACTA AAAAAGATGA GTACTTCACT ATGGCAGTTT    1800

ACAATAATAC TGCTACTCTA GAGGGGCGTG GTTCGGATGG GAAACAGTTT TACAATAATT    1860

ACAACGATGC ACCCTTAAAA GTTAAACCAG GTCAGTGGAA TTCTGTGACT TTCACAGTTG    1920
```

```
AAAAACCGAC AGCAGAACTA CCTAAAGGCC GAGTGCGCCT CTACGTAAAC GGGGTATTAT    1980

CTCGAACAAG TCTGAGATCT GGCAATTTCA TTAAAGATAT GCCAGATGTA ACGCATGTGC    2040

AAATCGGAGC AACCAAGCGT GCCAACAATA CGGTTTGGGG GTCAAATCTA CAGATTCGGA    2100

ATCTCACTGT GTATAATCGT GCTTTAACAC CAGAAGAGGT ACAAAAACGT AGTCAACTTT    2160

TTAAACGCTC AGATTTAGAA AAAAAACTAC CTGAAGGAGC GGCTTTAACA GAGAAAACGG    2220

ACATATTCGA AAGCGGGCGT AACGGTAAAC CAAATAAAGA TGGAATCAAG AGTTATCGTA    2280

TTCCAGCACT TCTCAAGACA GATAAAGGAA CTTTGATCGC AGGTGCAGAT GAACGCCGTC    2340

TCCATTCGAG TGACTGGGGT GATATCGGTA TGGTCATCAG ACGTAGTGAA GATAATGGTA    2400

AAACTTGGGG TGACCGAGTA ACCATTACCA ACTTACGTGA CAATCCAAAA GCTTCTGACC    2460

CATCGATCGG TTCACCAGTG AATATCGATA TGGTGTTGGT TCAAGATCCT GAAACCAAAC    2520

GAATCTTTTC TATCTATGAC ATGTTCCCAG AAGGGAAGGG AATCTTTGGA ATGTCTTCAC    2580

AAAAAGAAGA AGCCTACAAA AAAATCGATG GAAAAACCTA TCAAATCCTC TATCGTGAAG    2640

GAGAAAAGGG AGCTTATACC ATTCGAGAAA ATGGTACTGT CTATACACCA GATGGTAAGG    2700

CGACAGACTA TCGCGTTGTT GTAGATCCTG TTAAACCAGC CTATAGCGAC AAGGGGGATC    2760

TATACAAGGG TAACCAATTA CTAGGCAATA TCTACTTCAC AACAAACAAA ACTTCTCCAT    2820

TTAGAATTGC CAAGGATAGC TATCTATGGA TGTCCTACAG TGATGACGAC GGGAAGACAT    2880

GGTCAGCGCC TCAAGATATT ACTCCGATGG TCAAAGCCGA TTGGATGAAA TTCTTGGGTG    2940

TAGGTCCTGG AACAGGAATT GTACTTCGGA ATGGGCCTCA CAAGGGACGG ATTTTGATAC    3000

CGGTTTATAC GACTAATAAT GTATCTCACT TAAATGGCTC GCAATCTTCT CGTATCATCT    3060

ATTCAGATGA TCATGGAAAA ACTTGGCATG CTGGAGAAGC GGTCAACGAT AACCGTCAGG    3120

TAGACGGTCA AAAGATCCAC TCTTCTACGA TGAACAATAG ACGTGCGCAA AATACAGAAT    3180

CAACGGTGGC ACAACTAAAC AATGGAGATG TTAAACTCTT TATGCGTGGT TTGACTGGAG    3240

ATCTTCAGGT TGCTACAAGT AAAGACGGAG GAGTGACTTG GGAGAAGGAT ATCAAACGTT    3300

ATCCACAGGT TAAAGATGTC TATGTTCAAA TGTCTGCTAT CCATACGATG CACGAAGGAA    3360

AAGAATACAT CATCCTCAGT AATGCAGGTG GACCGAAACG TGAAAATGGG ATGGTCCACT    3420

TGGCACGTGT CGAAGAAAAT GGTGAGTTGA CTTGGCTCAA ACACAATCCA ATTCAAAAAG    3480

GAGAGTTTGC CTATAATTCG CTCCAAGAAT TAGGAAATGG GGAGTATGGC ATCTTGTATG    3540

AACATACTGA AAAAGGACAA AATGCCTATA CCCTATCATT TAGAAAATTT AATTGGGACT    3600

TTTTGAGCAA AGATCTGATT TCTCCTACCG AAGCGAAAGT GAAGCGAACT AGAGAGATGG    3660

GCAAAGGAGT TATTGGCTTG GAGTTCGACT CAGAAGTATT GGTCAACAAG GCTCCAACCC    3720

TTCAATTGGC AAATGGTAAA ACAGCACGCT TCATGACCCA GTATGATACA AAAACCCTCC    3780

TATTTACAGT GGATTCAGAG GATATGGGTC AAAAAGTTAC AGGTTTGGCA GAAGGTGCAA    3840

TTGAAAGTAT GCATAATTTA CCAGTCTCTG TGGCGGGCAC TAAGCTTTCG AATGGAATGA    3900

ACGGAAGTGA AGCTGCTGTT CATGAAGTGC CAGAATACAC AGGCCCATTA GGACATCCG    3960

GCGAAGAGCC AGCTCCAACA GTCGAGAAGC CAGAATACAC AGGCCCACTA GGACATCCG    4020

GCGAAGAGCC AGCCCCGACA GTCGAGAAGC CAGAATACAC AGGCCCACTA GGACAGCTG    4080

GTGAAGAAGC AGCTCCAACA GTCGAGAAGC CAGAATTTAC AGGGGGAGTT AATGGTACAG    4140

AGCCAGCTGT TCATGAAATC GCAGAGTATA AGGGATCTGA TTCGCTTGTA ACTCTTACTA    4200

CAAAAGAAGA TTATACTTAC AAAGCTCCTC TTGCTCAGCA GGCACTTCCT GAAACAGGAA    4260

ACAAGGAGAG TGACCTCCTA GCTTCACTAG GACTAACAGC TTTCTTCCTT GGTCTGTTTA    4320
```

```
CGCTAGGGAA AAAGAGAGAA CAATAAGAGA AGAATTCTAA ACATTTGATT TTGTAAAAAT      4380

AGAAGGAGAT AGCAGGTTTT CAAGCCTGCT ATCTTTTTTT GATGACATTC AGGCTGATAC      4440

GAAATCATAA GAGGTCTGAA ACTACTTTCA GAGTAGTCTG TTCTATAAAA TATAGTAGAT      4500

(2) INFORMATION FOR SEQ ID NO:36:

(i) SEQUENCE CHARACTERISTICS:
         (A) LENGTH: 705 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Staphylococcus epidermidis (xi) SEQUENCE DESCRIPTION: SEQ ID NO:36:

GATCCAAGCT TATCGATATC ATCAAAAAGT TGGCGAACCT TTTCAAATTT TGGTTCAAAT        60

TCTTGAGATG TATAGAATTC AAAATATTTA CCATTTGCAT AGTCTGATTG CTCAAAGTCT       120

TGATACTTTT CTCCACGCTC TTTTGCAATT TCCATTGAAC GTTCGATGGA ATAATAGTTC       180

ATAATCATAA AGAATATATT AGCAAAGTCT TTTGCTTCTT CAGATTCATA GCCAATTTTA       240

TTTTTAGCTA GATAACCATG TAAGTTCATT ACTCCTAGTC CAACAGAATG TAGTTCACTA       300

TTCGCTTTTT TTACACCTGG TGCATTTTGA ATATTTGCTT CATCACTTAC AACTGTAAGA       360

GCATCCATAC CTGTGAACAC AGAATCTCTG AATTTACCTG ATTCCATAAC ATTCACTATA       420

TTCAATGAGC CTAAGTTACA TGAAATATCT CTTTTAATTT CATCTTCAAT TCCATAGTCG       480

TTAATTACTG ATGTCTCTTG TAATTGGAAA ATTTCAGTAC ATAAATTACT CATTTTAATT       540

TGCCCAATAT TTGAATTCGC ATGTACTTTG TTTGCATTAT CTTTAAACAT AAGATATGGA       600

TAACCAGACT GTAATTGTGT TTGTGCAATC ATATTTAACA TTTCACGTGC GTCTTTTTTC       660

TTTTTATCGA TTTCGAACCC GGGGTACCGA ATTCCTCGAG TCTAG                      705

(2) INFORMATION FOR SEQ ID NO:37:

(i) SEQUENCE CHARACTERISTICS:
         (A) LENGTH: 442 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Staphylococcus aureus (xi) SEQUENCE DESCRIPTION: SEQ ID NO:37:

GATCAATCTT TGTCGGTACA CGATATTCTT CACGACTAAA TAAACGCTCA TTCGCGATTT        60

TATAAATGAA TGTTGATAAC AATGTTGTAT TATCTACTGA AATCTCATTA CGTTGCATCG       120

GAAACATTGT GTTCTGTATG TAAAAGCCGT CTTGATAATC TTTAGTAGTA CCGAAGCTGG       180

TCATACGAGA GTTATATTTT CCAGCCAAAA CGATATTTTT ATAATCATTA CGTGAAAAAG       240

GTTTCCCTTC ATTATCACAC AAATATTTTA GCTTTTCAGT TTCTATATCA ACTGTAGCTT       300

CTTTATCCAT ACGTTGAATA ATTGTACGAT TCTGACGCAC CATCTTTTGC ACACCTTTAA       360

TGTTATTTGT TTTAAAAGCA TGAATAAGTT TTTCAACACA ACGATGTGAA TCTTCTAAGA       420

AGTCACCGTA AAATGAAGGA TC                                               442

(2) INFORMATION FOR SEQ ID NO:38:
```

```
        (i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Enterococcus faecalis (xi) SEQUENCE DESCRIPTION: SEQ ID NO:38:

GCAATACAGG GAAAAATGTC                                                  20

(2) INFORMATION FOR SEQ ID NO:39:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Enterococcus faecalis (xi) SEQUENCE DESCRIPTION: SEQ ID NO:39:

CTTCATCAAA CAATTAACTC                                                  20

(2) INFORMATION FOR SEQ ID NO:40:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Enterococcus faecalis (xi) SEQUENCE DESCRIPTION: SEQ ID NO:40:

GAACAGAAGA AGCCAAAAAA                                                  20

(2) INFORMATION FOR SEQ ID NO:41:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Enterococcus faecalis (xi) SEQUENCE DESCRIPTION: SEQ ID NO:41:

GCAATCCCAA ATAATACGGT                                                  20

(2) INFORMATION FOR SEQ ID NO:42:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (genomic)
```

(vi) ORIGINAL SOURCE:
        (A) ORGANISM: Escherichia coli (xi) SEQUENCE DESCRIPTION: SEQ ID NO:42:

GCTTTCCAGC GTCATATTG                                                        19

(2) INFORMATION FOR SEQ ID NO:43:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:43:

GATCTCGACA AAATGGTGA                                                        19

(2) INFORMATION FOR SEQ ID NO:44:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:44:

CACCCGCTTG CGTGGCAAGC TGCCC                                                 25

(2) INFORMATION FOR SEQ ID NO:45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:45:

CGTTTGTGGA TTCCAGTTCC ATCCG                                                 25

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:46:

TCACCCGCTT GCGTGGC                                                          17

(2) INFORMATION FOR SEQ ID NO:47:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:47:

GGAACTGGAA TCCACAAAC                                              19

(2) INFORMATION FOR SEQ ID NO:48:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:48:

TGAAGCACTG GCCGAAATGC TGCGT                                     25

(2) INFORMATION FOR SEQ ID NO:49:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:49:

GATGTACAGG ATTCGTTGAA GGCTT                                     25

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:50:

TAGCGAAGGC GTAGCAGAAA CTAAC                                     25

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
             (A) ORGANISM: Escherichia coli (xi) SEQUENCE DESCRIPTION: SEQ ID NO:51:

GCAACCCGAA CTCAACGCCG GATTT                                                          25

(2) INFORMATION FOR SEQ ID NO:52:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Escherichia coli (xi) SEQUENCE DESCRIPTION: SEQ ID NO:52:

ATACACAAGG GTCGCATCTG CGGCC                                                          25

(2) INFORMATION FOR SEQ ID NO:53:

(i) SEQUENCE CHARACTERISTICS:
             (A) LENGTH: 26 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Escherichia coli (xi) SEQUENCE DESCRIPTION: SEQ ID NO:53:

TGCGTATGCA TTGCAGACCT TGTGGC                                                         26

(2) INFORMATION FOR SEQ ID NO:54:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Escherichia coli (xi) SEQUENCE DESCRIPTION: SEQ ID NO:54:

GCTTTCACTG GATATCGCGC TTGGG                                                          25

(2) INFORMATION FOR SEQ ID NO:55:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (genomic)

(vi) ORIGINAL SOURCE:
             (A) ORGANISM: Escherichia coli (xi) SEQUENCE DESCRIPTION: SEQ ID NO:55:

```
GCAACCCGAA CTCAACGCC                                                    19

(2) INFORMATION FOR SEQ ID NO:56:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Escherichia coli (xi) SEQUENCE DESCRIPTION: SEQ ID NO:56:

GCAGATGCGA CCCTTGTGT                                                    19

(2) INFORMATION FOR SEQ ID NO:57:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:57:

GTGGTGTCGT TCAGCGCTTT CAC                                               23

(2) INFORMATION FOR SEQ ID NO:58:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:58:

GCGATATTCA CACCCTACGC AGCCA                                             25

(2) INFORMATION FOR SEQ ID NO:59:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:59:

GTCGAAAATG CCGGAAGAGG TATACG                                            26

(2) INFORMATION FOR SEQ ID NO:60:

(i) SEQUENCE CHARACTERISTICS:
         (A) LENGTH: 26 base pairs
         (B) TYPE: nucleic acid
```

(C) STRANDEDNESS: single
            (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:60:

ACTGAGCTGC AGACCGGTAA AACTCA                                            26

(2) INFORMATION FOR SEQ ID NO:61:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:61:

GACAGTCAGT TCGTCAGCC                                                    19

(2) INFORMATION FOR SEQ ID NO:62:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:62:

CGTAGGGTGT GAATATCGC                                                    19

(2) INFORMATION FOR SEQ ID NO:63:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:63:

CGTGATGGAT ATTCTTAACG AAGGGC                                            26

(2) INFORMATION FOR SEQ ID NO:64:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
         (A) ORGANISM: Klebsiella pneumoniae (xi) SEQUENCE DESCRIPTION: SEQ ID NO:64:

ACCAAACTGT TGAGCCGCCT GGA                                                    23

(2) INFORMATION FOR SEQ ID NO:65:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:65:

GTGATCGCCC CTCATCTGCT ACT                                                    23

(2) INFORMATION FOR SEQ ID NO:66:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:66:

CGCCCTTCGT TAAGAATATC CATCAC                                                 26

(2) INFORMATION FOR SEQ ID NO:67:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:67:

TCGCCCCTCA TCTGCTACT                                                         19

(2) INFORMATION FOR SEQ ID NO:68:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:68:

GATCGTGATG GATATTCTT                                                         19

(2) INFORMATION FOR SEQ ID NO:69:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:69:

CAGGAAGATG CTGCACCGGT TGTTG                                             25

(2) INFORMATION FOR SEQ ID NO:70:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:70:

TGGTTCACTG ACTTTGCGAT GTTTC                                             25

(2) INFORMATION FOR SEQ ID NO:71:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:71:

TCGAGGATGG CATGCACTAG AAAAT                                             25

(2) INFORMATION FOR SEQ ID NO:72:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:72:

CGCTGATTAG GTTTCGCTAA AATCTTATTA                                        30

(2) INFORMATION FOR SEQ ID NO:73:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: Proteus mirabilis (xi) SEQUENCE DESCRIPTION: SEQ ID NO:73:

TTGATCCTCA TTTTATTAAT CACATGACCA                                                30

(2) INFORMATION FOR SEQ ID NO:74:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:74:

GAAACATCGC AAAGTCAGT                                                            19

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:75:

ATAAAATGAG GATCAAGTTC                                                           20

(2) INFORMATION FOR SEQ ID NO:76:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:76:

CCGCCTTTAG CATTAATTGG TGTTTATAGT                                                30

(2) INFORMATION FOR SEQ ID NO:77:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:77:

CCTATTGCAG ATACCTTAAA TGTCTTGGGC                                                30

(2) INFORMATION FOR SEQ ID NO:78:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:78:

AGTAAAATGA AATAAGAACA GGACAG                                          26

(2) INFORMATION FOR SEQ ID NO:79:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:79:

AAAACAGGAT AGGAGAACGG GAAAA                                           25

(2) INFORMATION FOR SEQ ID NO:80:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:80:

TTGAGTGATG ATTTCACTGA CTCCC                                           25

(2) INFORMATION FOR SEQ ID NO:81:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:81:

GTCAGACAGT GATGCTGACG ACACA                                           25

(2) INFORMATION FOR SEQ ID NO:82:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: Proteus mirabilis (xi) SEQUENCE DESCRIPTION: SEQ ID NO:82:

TGGTTGTCAT GCTGTTTGTG TGAAAAT                                                27

(2) INFORMATION FOR SEQ ID NO:83:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:83:

CGAGCGGGTG GTGTTCATC                                                         19

(2) INFORMATION FOR SEQ ID NO:84:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:84:

CAAGTCGTCG TCGGAGGGA                                                         19

(2) INFORMATION FOR SEQ ID NO:85:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:85:

TCGCTGTTCA TCAAGACCC                                                         19

(2) INFORMATION FOR SEQ ID NO:86:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:86:

CCGAGAACCA GACTTCATC                                                         19

(2) INFORMATION FOR SEQ ID NO:87:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:87:

AATGCGGCTG TACCTCGGCG CTGGT    25

(2) INFORMATION FOR SEQ ID NO:88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:88:

GGCGGAGGGC CAGTTGCACC TGCCA    25

(2) INFORMATION FOR SEQ ID NO:89:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:89:

AGCCCTGCTC CTCGGCAGCC TCTGC    25

(2) INFORMATION FOR SEQ ID NO:90:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Pseudomonas aeruginosa (xi) SEQUENCE DESCRIPTION: SEQ ID NO:90:

TGGCTTTTGC AACCGCGTTC AGGTT    25

(2) INFORMATION FOR SEQ ID NO:91:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:91:

GCGCCCGCGA GGGCATGCTT CGATG                                              25

(2) INFORMATION FOR SEQ ID NO:92:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:92:

ACCTGGGCGC CAACTACAAG TTCTA                                              25

(2) INFORMATION FOR SEQ ID NO:93:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:93:

GGCTACGCTG CCGGGCTGCA GGCCG                                              25

(2) INFORMATION FOR SEQ ID NO:94:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:94:

CCGATCTACA CCATCGAGAT GGGCG                                              25

(2) INFORMATION FOR SEQ ID NO:95:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Pseudomonas aeruginosa (xi) SEQUENCE DESCRIPTION: SEQ ID NO:95:

GAGCGCGGCT ATGTGTTCGT CGGCT                                             25

(2) INFORMATION FOR SEQ ID NO:96:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:96:

CGTTTTTACC CTTACCTTTT CGTACTACC                                         29

(2) INFORMATION FOR SEQ ID NO:97:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:97:

TCAGGCAGAG GTAGTACGAA AAGGTAAGGG                                         30

(2) INFORMATION FOR SEQ ID NO:98:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:98:

CGTTTTTACC CTTACCTTTT CGTACT                                            26

(2) INFORMATION FOR SEQ ID NO:99:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:99:

ATCGATCATC ACATTCCATT TGTTTTTA                                          28

(2) INFORMATION FOR SEQ ID NO:100:

(i) SEQUENCE CHARACTERISTICS:
        (A) LENGTH: 27 base pairs
        (B) TYPE: nucleic acid (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:100:

CACCAAGTTT GACACGTGAA GATTCAT                                         27

(2) INFORMATION FOR SEQ ID NO:101:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:101:

ATGAGTGAAG CGGAGTCAGA TTATGTGCAG                                      30

(2) INFORMATION FOR SEQ ID NO:102:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:102:

CGCTCATTAC GTACAGTGAC AATCG                                           25

(2) INFORMATION FOR SEQ ID NO:103:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:103:

CTGGTTAGCT TGACTCTTAA CAATCTTGTC                                      30

(2) INFORMATION FOR SEQ ID NO:104:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus

-continued (xi) SEQUENCE DESCRIPTION: SEQ ID NO:104:

GACGCGATTG TCACTGTACG TAATGAGCGA                             30

(2) INFORMATION FOR SEQ ID NO:105:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:105:

GCGTCAGAAA AAGTAGGCGA AATGAAAG                               28

(2) INFORMATION FOR SEQ ID NO:106:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:106:

AGCGGCTCTA TCTTGTAATG ACACA                                  25

(2) INFORMATION FOR SEQ ID NO:107:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:107:

GAAACGTGAA CTCCCCTCTA TATAA                                  25

(2) INFORMATION FOR SEQ ID NO:108:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:108:

GCCCCAAAAC AATGAAACAT ATGGT                                  25

(2) INFORMATION FOR SEQ ID NO:109:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:109:

CTGCAGATTT TGGAATCATA TCGCC                                              25

(2) INFORMATION FOR SEQ ID NO:110:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catharralis (xi) SEQUENCE DESCRIPTION: SEQ ID NO:110:

TGGTTTGACC AGTATTTAAC GCCAT                                              25

(2) INFORMATION FOR SEQ ID NO:111:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catharralis (xi) SEQUENCE DESCRIPTION: SEQ ID NO:111:

CAACGGCACC TGATGTACCT TGTAC                                              25

(2) INFORMATION FOR SEQ ID NO:112:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:112:

GGCACCTGAT GTACCTTG                                                      18

(2) INFORMATION FOR SEQ ID NO:113:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:

(A) ORGANISM: Moraxella catarrhalis (xi) SEQUENCE DESCRIPTION: SEQ ID NO:113:

AACAGCTCAC ACGCATT                                                               17

(2) INFORMATION FOR SEQ ID NO:114:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:114:

TTACAACCTG CACCACAAGT CATCA                                                      25

(2) INFORMATION FOR SEQ ID NO:115:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:115:

GTACAAACAA GCCGTCAGCG ACTTA                                                      25

(2) INFORMATION FOR SEQ ID NO:116:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:116:

CAATCTGCGT GTGTGCGTTC ACT                                                        23

(2) INFORMATION FOR SEQ ID NO:117:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Moraxella catarrhalis (xi) SEQUENCE DESCRIPTION: SEQ ID NO:117:

GCTACTTTGT CAGCTTTAGC CATTCA                                                     26

(2) INFORMATION FOR SEQ ID NO:118:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Moraxella catarrhalis (xi) SEQUENCE DESCRIPTION: SEQ ID NO:118:

TGTTTTGAGC TTTTTATTTT TTGA                                              24

(2) INFORMATION FOR SEQ ID NO:119:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Moraxella catarrhalis (xi) SEQUENCE DESCRIPTION: SEQ ID NO:119:

CGCTGACGGC TTGTTTGTAC CA                                                22

(2) INFORMATION FOR SEQ ID NO:120:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Streptococcus pneumoniae (xi) SEQUENCE DESCRIPTION: SEQ ID NO:120:

TCTGTGCTAG AGACTGCCCC ATTTC                                             25

(2) INFORMATION FOR SEQ ID NO:121:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Streptococcus pneumoniae (xi) SEQUENCE DESCRIPTION: SEQ ID NO:121:

CGATGTCTTG ATTGAGCAGG GTTAT                                             25

(2) INFORMATION FOR SEQ ID NO:122:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:122:

ATCCCACCTT AGGCGGCTGG CTCCA                                        25

(2) INFORMATION FOR SEQ ID NO:123:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:123:

ACGTCAAGTC ATCATGGCCC TTACGAGTAG G                                 31

(2) INFORMATION FOR SEQ ID NO:124:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:124:

GTGTGACGGG CGGTGTGTAC AAGGC                                        25

(2) INFORMATION FOR SEQ ID NO:125:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:125:

GAGTTGCAGA CTCCAATCCG GACTACGA                                     28

(2) INFORMATION FOR SEQ ID NO:126:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:126:

GGAGGAAGGT GGGGATGACG                                              20

(2) INFORMATION FOR SEQ ID NO:127:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:127:

ATGGTGTGAC GGGCGGTGTG                                              20

(2) INFORMATION FOR SEQ ID NO:128:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:128:

CCCTATACAT CACCTTGCGG TTTAGCAGAG AG                           32

(2) INFORMATION FOR SEQ ID NO:129:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:129:

GGGGGGACCA TCCTCCAAGG CTAAATAC                             28

(2) INFORMATION FOR SEQ ID NO:130:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:130:

CGTCCACTTT CGTGTTTGCA GAGTGCTGTG TT                           32

(2) INFORMATION FOR SEQ ID NO:131:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:131:

CAGGAGTACG GTGATTTTTA                                     20

(2) INFORMATION FOR SEQ ID NO:132:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Escherichia coli (xi) SEQUENCE DESCRIPTION: SEQ ID NO:132:

ATTTCTGGTT TGGTCATACA                                     20

(2) INFORMATION FOR SEQ ID NO:133:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:133:

CGGGAGTCAG TGAAATCATC                                      20

(2) INFORMATION FOR SEQ ID NO:134:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Proteus mirabilis (xi) SEQUENCE DESCRIPTION: SEQ ID NO:134:

CTAAAATCGC CACACCTCTT                                      20

(2) INFORMATION FOR SEQ ID NO:135:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:135:

GCAGCGTGGT GTCGTTCA                                        18

(2) INFORMATION FOR SEQ ID NO:136:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:136:

AGCTGGCAAC GGCTGGTC                                        18

(2) INFORMATION FOR SEQ ID NO:137:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:137:

ATTCACACCC TACGCAGCCA                                               20

(2) INFORMATION FOR SEQ ID NO:138:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Klebsiella pneumoniae (xi) SEQUENCE DESCRIPTION: SEQ ID NO:138:

ATCCGGCAGC ATCTCTTTGT                                               20

(2) INFORMATION FOR SEQ ID NO:139:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:139:

CTGGTTAGCT TGACTCTTAA CAATC                                         25

(2) INFORMATION FOR SEQ ID NO:140:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus saprophyticus (xi) SEQUENCE DESCRIPTION: SEQ ID NO:140:

TCTTAACGAT AGAATGGAGC AACTG                                         25

(2) INFORMATION FOR SEQ ID NO:141:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:141:

TGAAAATTCT TGTAACAGGC                                                    20

(2) INFORMATION FOR SEQ ID NO:142:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:142:

GGCCACCAGC TTGCCCAATA                                                    20

(2) INFORMATION FOR SEQ ID NO:143:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:143:

ATATTTTCTT TATGAGGGTG                                                    20

(2) INFORMATION FOR SEQ ID NO:144:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pyogenes (xi) SEQUENCE DESCRIPTION: SEQ ID NO:144:

ATCCTTAAAT AAAGTTGCCA                                                    20

(2) INFORMATION FOR SEQ ID NO:145:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus epidermidis (xi) SEQUENCE DESCRIPTION: SEQ ID NO:145:

ATCAAAAAGT TGGCGAACCT TTTCA                                              25

(2) INFORMATION FOR SEQ ID NO:146:

(i) SEQUENCE CHARACTERISTICS:
        (A) LENGTH: 25 base pairs (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus epidermidis (xi) SEQUENCE DESCRIPTION: SEQ ID NO:146:

CAAAAGAGCG TGGAGAAAAG TATCA                                         25

(2) INFORMATION FOR SEQ ID NO:147:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus epidermidis (xi) SEQUENCE DESCRIPTION: SEQ ID NO:147:

TCTCTTTTAA TTTCATCTTC AATTCCATAG                                    30

(2) INFORMATION FOR SEQ ID NO:148:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus epidermidis (xi) SEQUENCE DESCRIPTION: SEQ ID NO:148:

AAACACAATT ACAGTCTGGT TATCCATATC                                    30

(2) INFORMATION FOR SEQ ID NO:149:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus aureus (xi) SEQUENCE DESCRIPTION: SEQ ID NO:149:

CTTCATTTTA CGGTGACTTC TTAGAAGATT                                    30

(2) INFORMATION FOR SEQ ID NO:150:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Staphylococcus aureus (xi) SEQUENCE DESCRIPTION: SEQ ID NO:150:

TCAACTGTAG CTTCTTTATC CATACGTTGA                                          30

(2) INFORMATION FOR SEQ ID NO:151:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Staphylococcus aureus (xi) SEQUENCE DESCRIPTION: SEQ ID NO:151:

ATATTTTAGC TTTTCAGTTT CTATATCAAC                                          30

(2) INFORMATION FOR SEQ ID NO:152:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Staphylococcus aureus (xi) SEQUENCE DESCRIPTION: SEQ ID NO:152:

AATCTTTGTC GGTACACGAT ATTCTTCACG                                          30

(2) INFORMATION FOR SEQ ID NO:153:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Staphylococcus aureus (xi) SEQUENCE DESCRIPTION: SEQ ID NO:153:

CGTAATGAGA TTTCAGTAGA TAATACAACA                                          30

(2) INFORMATION FOR SEQ ID NO:154:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Haemophilus influenzae (xi) SEQUENCE DESCRIPTION: SEQ ID NO:154:

TTTAACGATC CTTTTACTCC TTTTG                                               25

(2) INFORMATION FOR SEQ ID NO:155:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Haemophilus influenzae (xi) SEQUENCE DESCRIPTION: SEQ ID NO:155:

ACTGCTGTTG TAAAGAGGTT AAAAT                                              25

(2) INFORMATION FOR SEQ ID NO:156:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:156:

ATTTGGTGAC GGGTGACTTT                                                    20

(2) INFORMATION FOR SEQ ID NO:157:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:157:

GCTGAGGATT TGTTCTTCTT                                                    20

(2) INFORMATION FOR SEQ ID NO:158:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Streptococcus pneumoniae (xi) SEQUENCE DESCRIPTION: SEQ ID NO:158:

GAGCGGTTTC TATGATTGTA                                                    20

(2) INFORMATION FOR SEQ ID NO:159:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
             (A) ORGANISM: Streptococcus pneumoniae (xi) SEQUENCE DESCRIPTION: SEQ ID NO:159:

ATCTTTCCTT TCTTGTTCTT                                                   20

(2) INFORMATION FOR SEQ ID NO:160:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(vi) ORIGINAL SOURCE:
            (A) ORGANISM: Moraxella catarrhalis (xi) SEQUENCE DESCRIPTION: SEQ ID NO:160:

GCTCAAATCA GGGTCAGC                                                     18

(2) INFORMATION FOR SEQ ID NO:161:

(i) SEQUENCE CHARACTERISTICS:
            (A) LENGTH: 861 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:161:

ATGAGTATTC AACATTTCCG TGTCGCCCTT ATTCCCTTTT TTGCGGCATT TTGCCTTCCT        60

GTTTTTGCTC ACCCAGAAAC GCTGGTGAAA GTAAAAGATG CTGAAGATCA GTTGGGTGCA       120

CGAGTGGGTT ACATCGAACT GGATCTCAAC AGCGGTAAGA TCCTTGAGAG TTTTCGCCCC       180

GAAGAACGTT TTCCAATGAT GAGCACTTTT AAAGTTCTGC TATGTGGCGC GGTATTATCC       240

CGTGTTGACG CCGGGCAAGA GCAACTCGGT CGCCGCATAC ACTATTCTCA GAATGACTTG       300

GTTGAGTACT CACCAGTCAC AGAAAAGCAT CTTACGGATG GCATGACAGT AAGAGAATTA       360

TGCAGTGCTG CCATAACCAT GAGTGATAAC ACTGCGGCCA ACTTACTTCT GACAACGATC       420

GGAGGACCGA AGGAGCTAAC CGCTTTTTTG CACAACATGG GGGATCATGT AACTCGCCTT       480

GATCGTTGGG AACCGGAGCT GAATGAAGCC ATACCAAACG ACGAGCGTGA CACCACGATG       540

CCTGCAGCAA TGGCAACAAC GTTGCGCAAA CTATTAACTG GCGAACTACT TACTCTAGCT       600

TCCCGGCAAC AATTAATAGA CTGGATGGAG GCGGATAAAG TTGCAGGACC ACTTCTGCGC       660

TCGGCCCTTC CGGCTGGCTG GTTTATTGCT GATAAATCTG GAGCCGGTGA GCGTGGGTCT       720

CGCGGTATCA TTGCAGCACT GGGGCCAGAT GGTAAGCCCT CCCGTATCGT AGTTATCTAC       780

ACGACGGGGA GTCAGGCAAC TATGGATGAA CGAAATAGAC AGATCGCTGA GATAGGTGCC       840

TCACTGATTA AGCATTGGTA A                                                861

(2) INFORMATION FOR SEQ ID NO:162:

(i) SEQUENCE CHARACTERISTICS:
            (A) LENGTH: 918 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:162:

-continued

```
ATGTTAAATA AGTTAAAAAT CGGCACATTA TTATTGCTGA CATTAACGGC TTGTTCGCCC      60

AATTCTGTTC ATTCGGTAAC GTCTAATCCG CAGCCTGCTA GTGCGCCTGT GCAACAATCA     120

GCCACACAAG CCACCTTTCA ACAGACTTTG GCGAATTTGG AACAGCAGTA TCAAGCCCGA     180

ATTGGCGTTT ATGTATGGGA TACAGAAACG GGACATTCTT TGTCTTATCG TGCAGATGAA     240

CGCTTTGCTT ATGCGTCCAC TTTCAAGGCG TTGTTGGCTG GGGCGGTGTT GCAATCGCTG     300

CCTGAAAAAG ATTTAAATCG TACCATTTCA TATAGCCAAA AAGATTTGGT TAGTTATTCT     360

CCCGAAACCC AAAAATACGT TGGCAAAGGC ATGACGATTG CCCAATTATG TGAAGCAGCC     420

GTGCGGTTTA GCGACAACAG CGCGACCAAT TTGCTGCTCA AGAATTGGG TGGCGTGGAA      480

CAATATCAAC GTATTTTGCG ACAATTAGGC GATAACGTAA CCCATACCAA TCGGCTAGAA     540

CCCGATTTAA ATCAAGCCAA ACCCAACGAT ATTCGTGATA CGAGTACACC CAAACAAATG     600

GCGATGAATT TAAATGCGTA TTTATTGGGC AACACATTAA CCGAATCGCA AAAAACGATT     660

TTGTGGAATT GGTTGGACAA TAACGCAACA GGCAATCCAT TGATTCGCGC TGCTACGCCA     720

ACATCGTGGA AAGTGTACGA TAAAAGCGGG GCGGGTAAAT ATGGTGTACG CAATGATATT     780

GCGGTGGTTC GCATACCAAA TCGCAAACCG ATTGTGATGG CAATCATGAG TACGCAATTT     840

ACCGAAGAAG CCAAATTCAA CAATAAATTA GTAGAAGATG CAGCAAAGCA AGTATTTCAT     900

ACTTTACAGC TCAACTAA                                                   918
```

(2) INFORMATION FOR SEQ ID NO:163:

(i) SEQUENCE CHARACTERISTICS:
        (A) LENGTH: 864 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:163:

```
ATGCGTTATA TTCGCCTGTG TATTATCTCC CTGTTAGCCA CCCTGCCGCT GGCGGTACAC      60

GCCAGCCCGC AGCCGCTTGA GCAAATTAAA CTAAGCGAAA GCCAGCTGTC GGGCCGCGTA     120

GGCATGATAG AAATGGATCT GGCCAGCGGC CGCACGCTGA CCGCCTGGCG CGCCGATGAA     180

CGCTTTCCCA TGATGAGCAC CTTTAAAGTA GTGCTCTGCG GCGCAGTGCT GGCGCGGGTG     240

GATGCCGGTG ACGAACAGCT GGAGCGAAAG ATCCACTATC GCCAGCAGGA TCTGGTGGAC     300

TACTCGCCGG TCAGCGAAAA ACACCTTGCC GACGCAATGA CGGTCGGCGA ACTCTGCGCC     360

GCCGCCATTA CCATGAGCGA TAACAGCGCC GCCAATCTGC TACTGGCCAC CGTCGGCGGC     420

CCCGCAGGAT TGACTGCCTT TTTGCGCCAG ATCGGCGACA ACGTCACCCG CCTTGACCGC     480

TGGGAAACGG AACTGAATGA GGCGCTTCCC GGCGACGCCC GCGACACCAC TACCCCGGCC     540

AGCATGGCCG CGACCCTGCG CAACGTTGGC CTGACCAGCC AGCGTCTGAG CGCCCGTTCG     600

CAACGGCAGC TGCTGCAGTG GATGGTGGAC GATCGGGTCG CCGGACCGTT GATCCGCTCC     660

GTGCTGCCGG CGGGCTGGTT TATCGCCGAT AAGACCGGAG CTGGCGAGCG GGGTGCGCGC     720

GGGATTGTCG CCCTGCTTGG CCCGAATAAC AAAGCAGAGC GCATTGTGGT GATTTATCTG     780

CGGGATACCC CGGCGAGCAT GGCCGAGCGA AATCAGCAAA TCGCCGGGAT CGGCAAGGCG     840

CTGTACGAGC ACTGGCAACG CTAA                                            864
```

(2) INFORMATION FOR SEQ ID NO:164:

(i) SEQUENCE CHARACTERISTICS:

-continued

```
        (A) LENGTH: 534 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:164:

ATGGACACAA CGCAGGTCAC ATTGATACAC AAAATTCTAG CTGCGGCAGA TGAGCGAAAT      60

CTGCCGCTCT GGATCGGTGG GGGCTGGGCG ATCGATGCAC GGCTAGGGCG TGTAACACGC     120

AAGCACGATG ATATTGATCT GACGTTTCCC GGCGAGAGGC GCGGCGAGCT CGAGGCAATA     180

GTTGAAATGC TCGGCGGGCG CGTCATGGAG GAGTTGGACT ATGGATTCTT AGCGGAGATC     240

GGGGATGAGT TACTTGACTG CGAACCTGCT TGGTGGGCAG ACGAAGCGTA TGAAATCGCG     300

GAGGCTCCGC AGGGCTCGTG CCCAGAGGCG GCTGAGGGCG TCATCGCCGG GCGGCCAGTC     360

CGTTGTAACA GCTGGGAGGC GATCATCTGG GATTACTTTT ACTATGCCGA TGAAGTACCA     420

CCAGTGGACT GGCCTACAAA GCACATAGAG TCCTACAGGC TCGCATGCAC CTCACTCGGG     480

GCGGAAAAGG TTGAGGTCTT GCGTGCCGCT TTCAGGTCGC GATATGCGGC CTAA           534

(2) INFORMATION FOR SEQ ID NO:165:

(i) SEQUENCE CHARACTERISTICS:
        (A) LENGTH: 465 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:165:

ATGGGCATCA TTCGCACATG TAGGCTCGGC CCTGACCAAG TCAAATCCAT GCGGGCTGCT      60

CTTGATCTTT TCGGTCGTGA GTTCGGAGAC GTAGCCACCT ACTCCCAACA TCAGCCGGAC     120

TCCGATTACC TCGGGAACTT GCTCCGTAGT AAGACATTCA TCGCGCTTGC TGCCTTCGAC     180

CAAGAAGCGG TTGTTGGCGC TCTCGCGGCT TACGTTCTGC CCAGGTTTGA GCAGCCGCGT     240

AGTGAGATCT ATATCTATGA TCTCGCAGTC TCCGGCGAGC ACCGGAGGCA GGGCATTGCC     300

ACCGCGCTCA TCAATCTCCT CAAGCATGAG GCCAACGCGC TTGGTGCTTA TGTGATCTAC     360

GTGCAAGCAG ATTACGGTGA CGATCCCGCA GTGGCTCTCT ATACAAAGTT GGGCATACGG     420

GAAGAAGTGA TGCACTTTGA TATCGACCCA AGTACCGCCA CCTAA                    465

(2) INFORMATION FOR SEQ ID NO:166:

(i) SEQUENCE CHARACTERISTICS:
        (A) LENGTH: 861 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:166:

ATGCATACGC GGAAGGCAAT AACGGAGGCG CTTCAAAAAC TCGGAGTCCA AACCGGTGAC      60

CTATTGATGG TGCATGCCTC ACTTAAAGCG ATTGGTCCGG TCGAAGGAGG AGCGGAGACG     120

GTCGTTGCCG CGTTACGCTC CGCGGTTGGG CCGACTGGCA CTGTGATGGG ATACGCATCG     180

TGGGACCGAT CACCCTACGA GGAGACTCGT AATGGCGCTC GGTTGGATGA CAAAACCCGC     240

CGTACCTGGC CGCCGTTCGA TCCCGCAACG GCCGGGACTT ACCGTGGGTT CGGCCTGCTG     300

AATCAGTTTC TGGTTCAAGC CCCCGGCGCG CGGCGCAGCG CGCACCCCGA TGCATCGATG     360
```

```
GTCGCGGTTG GTCCACTGGC TGAAACGCTG ACGGAGCCTC ACAAGCTCGG TCACGCCTTG    420

GGGGAAGGGT CGCCCGTCGA GCGGTTCGTT CGCCTTGGCG GGAAGGCCCT GCTGTTGGGT    480

GCGCCGCTAA ACTCCGTTAC CGCATTGCAC TACGCCGAGG CGGTTGCCGA TATCCCCAAC    540

AAACGGCGGG TGACGTATGA GATGCCGATG CTTGGAAGCA ACGGCGAAGT CGCCTGGAAA    600

ACGGCATCGG ATTACGATTC AAACGGCATT CTCGATTGCT TTGCTATCGA AGGAAAGCCG    660

GATGCGGTCG AAACTATAGC AAATGCTTAC GTGAAGCTCG GTCGCCATCG AGAAGGTGTC    720

GTGGGCTTTG CTCAGTGCTA CCTGTTCGAC GCGCAGGACA TCGTGACGTT CGGCGTCACC    780

TATCTTGAGA AGCATTTCGG AACCACTCCG ATCGTGCCAG CACACGAAGT CGCCGAGTGC    840

TCTTGCGAGC CTTCAGGTTA G                                              861
```

(2) INFORMATION FOR SEQ ID NO:167:

(i) SEQUENCE CHARACTERISTICS:
        (A) LENGTH: 816 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:167:

```
ATGACCGATT TGAATATCCC GCATACACAC GCGCACCTTG TAGACGCATT TCAGGCGCTC    60

GGCATCCGCG CGGGGCAGGC GCTCATGCTG CACGCATCCG TTAAAGCAGT GGGCGCGGTG    120

ATGGGCGGCC CCAATGTGAT CTTGCAGGCG CTCATGGATG CGCTCACGCC CGACGGCACG    180

CTGATGATGT ATGCGGGATG GCAAGACATC CCCGACTTTA TCGACTCGCT GCCGGACGCG    240

CTCAAGGCCG TGTATCTTGA GCAGCACCCA CCCTTTGACC CCGCCACCGC CCGCGCCGTG    300

CGCGAAAACA GCGTGCTAGC GGAATTTTTG CGCACATGGC CGTGCGTGCA TCGCAGCGCA    360

AACCCCGAAG CCTCTATGGT GGCGGTAGGC AGGCAGGCCG CTTTGCTGAC CGCTAATCAC    420

GCGCTGGATT ATGGCTACGG AGTCGAGTCG CCGCTGGCTA AACTGGTGGC AATAGAAGGA    480

TACGTGCTGA TGCTTGGCGC GCCGCTGGAT ACCATCACAC TGCTGCACCA CGCGGAATAT    540

CTGGCCAAGA TGCGCCACAA GAACGTGGTC CGCTACCCGT GCCCGATTCT GCGGGACGGG    600

CGCAAAGTGT GGGTGACCGT TGAGGACTAT GACACCGGTG ATCCGCACGA CGATTATAGT    660

TTTGAGCAAA TCGCGCGCGA TTATGTGGCG CAGGGCGGCG GCACACGCGG CAAAGTCGGT    720

GATGCGGATG CTTACCTGTT CGCCGCGCAG GACCTCACAC GGTTTGCGGT GCAGTGGCTT    780

GAATCACGGT TCGGTGACTC AGCGTCATAC GGATAG                              816
```

(2) INFORMATION FOR SEQ ID NO:168:

(i) SEQUENCE CHARACTERISTICS:
        (A) LENGTH: 498 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:168:

```
ATGCTCTATG AGTGGCTAAA TCGATCTCAT ATCGTCGAGT GGTGGGCGG AGAAGAAGCA     60

CGCCCGACAC TTGCTGACGT ACAGGAACAG TACTTGCCAA GCGTTTTAGC GCAAGAGTCC    120

GTCACTCCAT ACATTGCAAT GCTGAATGGA GAGCCGATTG GGTATGCCCA GTCGTACGTT    180

GCTCTTGGAA GCGGGGACGG ATGGTGGGAA GAAGAAACCG ATCCAGGAGT ACGCGGAATA    240
```

```
GACCAGTTAC TGGCGAATGC ATCACAACTG GGCAAAGGCT TGGGAACCAA GCTGGTTCGA      300

GCTCTGGTTG AGTTGCTGTT CAATGATCCC GAGGTCACCA AGATCCAAAC GGACCCGTCG      360

CCGAGCAACT TGCGAGCGAT CCGATGCTAC GAGAAAGCGG GGTTTGAGAG GCAAGGTACC      420

GTAACCACCC CAGATGGTCC AGCCGTGTAC ATGGTTCAAA CACGCCAGGC ATTCGAGCGA      480

ACACGCAGTG ATGCCTAA                                                   498

(2) INFORMATION FOR SEQ ID NO:169:

(i) SEQUENCE CHARACTERISTICS:
        (A) LENGTH: 2007 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:169:

ATGAAAAAGA TAAAAATTGT TCCACTTATT TTAATAGTTG TAGTTGTCGG GTTTGGTATA       60

TATTTTTATG CTTCAAAAGA TAAAGAAATT AATAATACTA TTGATGCAAT TGAAGATAAA      120

AATTTCAAAC AAGTTTATAA AGATAGCAGT TATATTTCTA AAAGCGATAA TGGTGAAGTA      180

GAAATGACTG AACGTCCGAT AAAAATATAT AATAGTTTAG GCGTTAAAGA TATAAACATT      240

CAGGATCGTA AAATAAAAAA AGTATCTAAA AATAAAAAAC GAGTAGATGC TCAATATAAA      300

ATTAAAACAA ACTACGGTAA CATTGATCGC AACGTTCAAT TTAATTTTGT TAAAGAAGAT      360

GGTATGTGGA AGTTAGATTG GGATCATAGC GTCATTATTC CAGGAATGCA GAAAGACCAA      420

AGCATACATA TTGAAAATTT AAAATCAGAA CGTGGTAAAA TTTTAGACCG AAACAATGTG      480

GAATTGGCCA ATACAGGAAC ACATATGAGA TTAGGCATCG TTCCAAAGAA TGTATCTAAA      540

AAAGATTATA AAGCAATCGC TAAAGAACTA AGTATTTCTG AAGACTATAT CAACAACAAA      600

TGGATCAAAA TTGGGTACAA GATGATACCT TCGTTCCACT TTAAAACCGT TAAAAAAATG      660

GATGAATATT TAAGTGATTT CGCAAAAAAA TTTCATCTTA CAACTAATGA AACAGAAAGT      720

CGTAACTATC CTCTAGAAAA AGCGACTTCA CATCTATTAG GTTATGTTGG TCCCATTAAC      780

TCTGAAGAAT TAAAACAAAA AGAATATAAA GGCTATAAAG ATGATGCAGT TATTGGTAAA      840

AAGGGACTCG AAAAACTTTA CGATAAAAAG CTCCAACATG AAGATGGCTA TCGTGTCACA      900

ATCGTTGACG ATAATAGCAA TACAATCGCA CATACATTAA TAGAGAAAAA GAAAAAAGAT      960

GGCAAAGATA TTCAACTAAC TATTGATGCT AAAGTTCAAA AGAGTATTTA TAACAACATG     1020

AAAAATGATT ATGGCTCAGG TACTGCTATC CACCCTCAAA CAGGTGAATT ATTAGCACTT     1080

GTAAGCACAC CTTCATATGA CGTCTATCCA TTTATGTATG GCATGAGTAA CGAAGAATAT     1140

AATAAATTAA CCGAAGATAA AAAAGAACCT CTGCTCAACA AGTTCCAGAT TACAACTTCA     1200

CCAGGTTCAA CTCAAAAAAT ATTAACAGCA ATGATTGGGT TAAATAACAA ACATTAGAC     1260

GATAAAACAA GTTATAAAAT CGATGGTAAA GGTTGGCAAA AAGATAAATC TTGGGGTGGT     1320

TACAACGTTA CAAGATATGA AGTGGTAAAT GGTAATATCG ACTTAAAACA AGCAATGAAA     1380

TCATCAGATA ACATTTTCTT TGCTAGAGTA GCACTCGAAT TAGGCAGTAA GAAATTTGAA     1440

AAAGGCATGA AAAAACTAGG TGTTGGTGAA GATATACCAA GTGATTATCC ATTTTATAAT     1500

GCTCAAATTT CAAACAAAAA TTTAGATAAT GAAATATTAT TAGCTGATTC AGGTTACGGA     1560

CAAGGTGAAA TACTGATTAA CCCAGTACAG ATCCTTTCAA TCTATAGCGC ATTAGAAAAT     1620

AATGGCAATA TTAACGCACC TCACTTATTA AAAGACACGA AAAACAAAGT TTGGAAGAAA     1680
```

-continued

| AATATTATTT CCAAAGAAAA TATCAATCTA TTAAATGATG GTATGCAACA AGTCGTAAAT | 1740 |
| AAAACACATA AAGAAGATAT TTATAGATCT TATGCAAACT TAATTGGCAA ATCCGGTACT | 1800 |
| GCAGAACTCA AAATGAAACA AGGAGAAAGT GGCAGACAAA TTGGGTGGTT TATATCATAT | 1860 |
| GATAAAGATA ATCCAAACAT GATGATGGCT ATTAATGTTA AAGATGTACA AGATAAAGGA | 1920 |
| ATGGCTAGCT ACAATGCCAA AATCTCAGGT AAAGTGTATG ATGAGCTATA TGAGAACGGT | 1980 |
| AATAAAAAAT ACGATATAGA TGAATAA | 2007 |

(2) INFORMATION FOR SEQ ID NO:170:

(i) SEQUENCE CHARACTERISTICS:
        (A) LENGTH: 2607 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:170:

| ATGAATAACA TCGGCATTAC TGTTTATGGA TGTGAGCAGG ATGAGGCAGA TGCATTCCAT | 60 |
| GCTCTTTCGC CTCGCTTTGG CGTTATGGCA ACGATAATTA ACGCCAACGT GTCGGAATCC | 120 |
| AACGCCAAAT CCGCGCCTTT CAATCAATGT ATCAGTGTGG ACATAAATC AGAGATTTCC | 180 |
| GCCTCTATTC TTCTTGCGCT GAAGAGAGCC GGTGTGAAAT ATATTTCTAC CCGAAGCATC | 240 |
| GGCTGCAATC ATATAGATAC AACTGCTGCT AAGAGAATGG GCATCACTGT CGACAATGTG | 300 |
| GCGTACTCGC CGGATAGCGT TGCCGATTAT ACTATGATGC TAATTCTTAT GGCAGTACGC | 360 |
| AACGTAAAAT CGATTGTGCG CTCTGTGGAA AAACATGATT TCAGGTTGGA CAGCGACCGT | 420 |
| GGCAAGGTAC TCAGCGACAT GACAGTTGGT GTGGTGGGAA CGGGCCAGAT AGGCAAAGCG | 480 |
| GTTATTGAGC GGCTGCGAGG ATTTGGATGT AAAGTGTTGG CTTATAGTCG CAGCCGAAGT | 540 |
| ATAGAGGTAA ACTATGTACC GTTTGATGAG TTGCTGCAAA ATAGCGATAT CGTTACGCTT | 600 |
| CATGTGCCGC TCAATACGGA TACGCACTAT ATTATCAGCC ACGAACAAAT ACAGAGAATG | 660 |
| AAGCAAGGAG CATTTCTTAT CAATACTGGG CGCGGTCCAC TTGTAGATAC CTATGAGTTG | 720 |
| GTTAAAGCAT TAGAAAACGG GAAACTGGGC GGTGCCGCAT GGATGTATT GGAAGGAGAG | 780 |
| GAAGAGTTTT TCTACTCTGA TTGCACCCAA AAACCAATTG ATAATCAATT TTTACTTAAA | 840 |
| CTTCAAAGAA TGCCTAACGT GATAATCACA CCGCATACGG CCTATTATAC CGAGCAAGCG | 900 |
| TTGCGTGATA CCGTTGAAAA AACCATTAAA AACTGTTTGG ATTTTGAAAG GAGACAGGAG | 960 |
| CATGAATAGA ATAAAAGTTG CAATACTGTT TGGGGGTTGC TCAGAGGAGC ATGACGTATC | 1020 |
| GGTAAAATCT GCAATAGAGA TAGCCGCTAA CATTAATAAA GAAAAATACG AGCCGTTATA | 1080 |
| CATTGGAATT ACGAAATCTG GTGTATGGAA AATGTGCGAA AAACCTTGCG CGGAATGGGA | 1140 |
| AAACGACAAT TGCTATTCAG CTGTACTCTC GCCGGATAAA AAAATGCACG GATTACTTGT | 1200 |
| TAAAAAGAAC CATGAATATG AAATCAACCA TGTTGATGTA GCATTTTCAG CTTTGCATGG | 1260 |
| CAAGTCAGGT GAAGATGGAT CCATACAAGG TCTGTTTGAA TTGTCCGGTA TCCCTTTTGT | 1320 |
| AGGCTGCGAT ATTCAAAGCT CAGCAATTTG TATGGACAAA TCGTTGACAT ACATCGTTGC | 1380 |
| GAAAAATGCT GGGATAGCTA CTCCCGCCTT TGGGTTATT AATAAAGATG ATAGGCCGGT | 1440 |
| GGCAGCTACG TTTACCTATC CTGTTTTTGT TAAGCCGGCG CGTTCAGGCT CATCCTTCGG | 1500 |
| TGTGAAAAAA GTCAATAGCG CGGACGAATT GGACTACGCA ATTGAATCGG CAAGACAATA | 1560 |
| TGACAGCAAA ATCTTAATTG AGCAGGCTGT TTCGGGCTGT GAGGTCGGTT GTGCGGTATT | 1620 |
| GGGAAACAGT GCCGCGTTAG TTGTTGGCGA GGTGGACCAA ATCAGGCTGC AGTACGGAAT | 1680 |

-continued

| | |
|---|---|
| CTTTCGTATT CATCAGGAAG TCGAGCCGGA AAAAGGCTCT GAAAACGCAG TTATAACCGT | 1740 |
| TCCCGCAGAC CTTTCAGCAG AGGAGCGAGG ACGGATACAG GAAACGGCAA AAAAAATATA | 1800 |
| TAAAGCGCTC GGCTGTAGAG GTCTAGCCCG TGTGGATATG TTTTTACAAG ATAACGGCCG | 1860 |
| CATTGTACTG AACGAAGTCA ATACTCTGCC CGGTTTCACG TCATACAGTC GTTATCCCCG | 1920 |
| TATGATGGCC GCTGCAGGTA TTGCACTTCC CGAACTGATT GACCGCTTGA TCGTATTAGC | 1980 |
| GTTAAAGGGG TGATAAGCAT GGAAATAGGA TTTACTTTTT TAGATGAAAT AGTACACGGT | 2040 |
| GTTCGTTGGG ACGCTAAATA TGCCACTTGG GATAATTTCA CCGGAAAACC GGTTGACGGT | 2100 |
| TATGAAGTAA ATCGCATTGT AGGGACATAC GAGTTGGCTG AATCGCTTTT GAAGGCAAAA | 2160 |
| GAACTGGCTG CTACCCAAGG GTACGGATTG CTTCTATGGG ACGGTTACCG TCCTAAGCGT | 2220 |
| GCTGTAAACT GTTTTATGCA ATGGGCTGCA CAGCCGGAAA ATAACCTGAC AAAGGAAAGT | 2280 |
| TATTATCCCA ATATTGACCG AACTGAGATG ATTTCAAAAG GATACGTGGC TTCAAAATCA | 2340 |
| AGCCATAGCC GCGGCAGTGC CATTGATCTT ACGCTTTATC GATTAGACAC GGGTGAGCTT | 2400 |
| GTACCAATGG GGAGCCGATT TGATTTTATG GATGAACGCT CTCATCATGC GGCAAATGGA | 2460 |
| ATATCATGCA ATGAAGCGCA AAATCGCAGA CGTTTGCGCT CCATCATGGA AAACAGTGGG | 2520 |
| TTTGAAGCAT ATAGCCTCGA ATGGTGGCAC TATGTATTAA GAGACGAACC ATACCCCAAT | 2580 |
| AGCTATTTTG ATTTCCCCGT TAAATAA | 2607 |

(2) INFORMATION FOR SEQ ID NO:171:

(i) SEQUENCE CHARACTERISTICS:
        (A) LENGTH: 1288 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:171:

| | |
|---|---|
| GGATCCATCA GGCAACGACG GGCTGCTGCC GGCCATCAGC GGACGCAGGG AGGACTTTCC | 60 |
| GCAACCGGCC GTTCGATGCG GCACCGATGG CCTTCGCGCA GGGGTAGTGA ATCCGCCAGG | 120 |
| ATTGACTTGC GCTGCCCTAC CTCTCACTAG TGAGGGGCGG CAGCGCATCA AGCGGTGAGC | 180 |
| GCACTCCGGC ACCGCCAACT TTCAGCACAT GCGTGTAAAT CATCGTCGTA GAGACGTCGG | 240 |
| AATGGCCGAG CAGATCCTGC ACGGTTCGAA TGTCGTAACC GCTGCGGAGC AAGGCCGTCG | 300 |
| CGAACGAGTG GCGGAGGGTG TGCGGTGTGG CGGGCTTCGT GATGCCTGCT TGTTCTACGG | 360 |
| CACGTTTGAA GGCGCGCTGA AAGGTCTGGT CATACATGTG ATGGCGACGC ACGACACCGC | 420 |
| TCCGTGGATC GGTCGAATGC GTGTGCTGCG CAAAAACCCA GAACCACGGC CAGGAATGCC | 480 |
| CGGCGCGCGG ATACTTCCGC TCAAGGGCGT CGGGAAGCGC AACGCCGCTG CGGCCCTCGG | 540 |
| CCTGGTCCTT CAGCCACCAT GCCCGTGCAC GCGACAGCTG CTCGCGCAGG CTGGGTGCCA | 600 |
| AGCTCTCGGG TAACATCAAG GCCCGATCCT TGGAGCCCTT GCCCTCCCGC ACGATGATCG | 660 |
| TGCCGTGATC GAAATCCAGA TCCTTGACCC GCAGTTGCAA ACCCTCACTG ATCCGCATGC | 720 |
| CCGTTCCATA CAGAAGCTGG GCGAACAAAC GATGCTCGCC TTCCAGAAAA CCGAGGATGC | 780 |
| GAACCACTTC ATCCGGGGTC AGCACCACCG GCAAGCGCCG CGACGGCCGA GGTCTTCCGA | 840 |
| TCTCCTGAAG CCAGGGCAGA TCCGTGCACA GCACCTTGCC GTAGAAGAAC AGCAAGGCCG | 900 |
| CCAATGCCTG ACGATGCGTG GAGACCGAAA CCTTGCGCTC GTTCGCCAGC CAGGACAGAA | 960 |
| ATGCCTCGAC TTCGCTGCTG CCCAAGGTTG CCGGGTGACG CACACCGTGG AAACGGATGA | 1020 |

```
AGGCACGAAC CCAGTGGACA TAAGCCTGTT CGGTTCGTAA GCTGTAATGC AAGTAGCGTA      1080

TGCGCTCACG CAACTGGTCC AGAACCTTGA CCGAACGCAG CGGTGGTAAC GGCGCAGTGG      1140

CGGTTTTCAT GGCTTGTTAT GACTGTTTTT TTGTACAGTC TATGCCTCGG GCATCCAAGC      1200

AGCAAGCGCG TTACGCCGTG GGTCGATGTT TGATGTTATG GAGCAGCAAC GATGTTACGC      1260

AGCAGGGCAG TCGCCCTAAA ACAAAGTT                                         1288
```

(2) INFORMATION FOR SEQ ID NO:172:

(i) SEQUENCE CHARACTERISTICS:
        (A) LENGTH: 1650 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:172:

```
GTTAGATGCA CTAAGCACAT AATTGCTCAC AGCCAAACTA TCAGGTCAAG TCTGCTTTTA        60

TTATTTTTAA GCGTGCATAA TAAGCCCTAC ACAAATTGGG AGATATATCA TGAAAGGCTG       120

GCTTTTTCTT GTTATCGCAA TAGTTGGCGA AGTAATCGCA ACATCCGCAT TAAAATCTAG       180

CGAGGGCTTT ACTAAGCTTG CCCCTTCCGC CGTTGTCATA ATCGGTTATG GCATCGCATT       240

TTATTTTCTT TCTCTGGTTC TGAAATCCAT CCCTGTCGGT GTTGCTTATG CAGTCTGGTC       300

GGGACTCGGC GTCGTCATAA TTACAGCCAT TGCCTGGTTG CTTCATGGGC AAAAGCTTGA       360

TGCGTGGGGC TTTGTAGGTA TGGGGCTCAT AATTGCTGCC TTTTTGCTCG CCCGATCCCC       420

ATCGTGGAAG TCGCTGCGGA GGCCGACGCC ATGGTGACGG TGTTCGGCAT TCTGAATCTC       480

ACCGAGGACT CCTTCTTCGA TGAGAGCCGG CGGCTAGACC CCGCCGGCGC TGTCACCGCG       540

GCGATCGAAA TGCTGCGAGT CGGATCAGAC GTCGTGGATG TCGGACCGGC CGCCAGCCAT       600

CCGGACGCGA GGCCTGTATC GCCGGCCGAT GAGATCAGAC GTATTGCGCC GCTCTTAGAC       660

GCCCTGTCCG ATCAGATGCA CCGTGTTTCA ATCGACAGCT TCCAACCGGA AACCCAGCGC       720

TATGCGCTCA AGCGCGGCGT GGGCTACCTG AACGATATCC AAGGATTTCC TGACCCTGCG       780

CTCTATCCCG ATATTGCTGA GGCGGACTGC AGGCTGGTGG TTATGCACTC AGCGCAGCGG       840

GATGGCATCG CCACCCGCAC CGGTCACCTT CGACCCGAAG ACGCGCTCGA CGAGATTGTG       900

CGGTTCTTCG AGGCGCGGGT TTCCGCCTTG CGACGGAGCG GGGTCGCTGC CGACCGGCTC       960

ATCCTCGATC CGGGGATGGG ATTTTTCTTG AGCCCCGCAC CGGAAACATC GCTGCACGTG      1020

CTGTCGAACC TTCAAAAGCT GAAGTCGGCG TTGGGGCTTC CGCTATTGGT CTCGGTGTCG      1080

CGGAAATCCT TCTTGGGCGC CACCGTTGGC CTTCCTGTAA AGGATCTGGG TCCAGCGAGC      1140

CTTGCGGCGG AACTTCACGC GATCGGCAAT GGCGCTGACT ACGTCCGCAC CCACGCGCCT      1200

GGAGATCTGC GAAGCGCAAT CACCTTCTCG GAAACCCTCG CGAAATTTCG CAGTCGCGAC      1260

GCCAGAGACC GAGGGTTAGA TCATGCCTAG CATTCACCTT CCGGCCGCCC GCTAGCGGAC      1320

CCTGGTCAGG TTCCGCGAAG GTGGGCGCAG ACATGCTGGG CTCGTCAGGA TCAAACTGCA      1380

CTATGAGGCG GCGGTTCATA CCGCGCCAGG GGAGCGAATG GACAGCGAGG AGCCTCCGAA      1440

CGTTCGGGTC GCCTGCTCGG GTGATATCGA CGAGGTTGTG CGGCTGATGC ACGACGCTGC      1500

GGCGTGGATG TCCGCCAAGG GAACGCCCGC CTGGGACGTC GCGCGGATCG ACCGGACATT      1560

CGCGGAGACC TTCGTCCTGA GATCCGAGCT CCTAGTCGCG AGTTGCAGCG ACGGCATCGT      1620

CGGCTGTTGC ACCTTGTCGG CCGAGGATCC                                      1650
```

(2) INFORMATION FOR SEQ ID NO:173:

(i) SEQUENCE CHARACTERISTICS:
        (A) LENGTH: 630 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:173:

| | | | | | |
|---|---|---|---|---|---|
| ATGGGTCCGA | ATCCTATGAA | AATGTATCCT | ATAGAAGGAA | ACAAATCAGT | ACAATTTATC | 60 |
| AAACCTATTT | TAGAAAAATT | AGAAAATGTT | GAGGTTGGAG | AATACTCATA | TTATGATTCT | 120 |
| AAGAATGGAG | AAACTTTTGA | TAAGCAAATT | TTATATCATT | ATCCAATCTT | AAACGATAAG | 180 |
| TTAAAAATAG | GTAAATTTTG | CTCAATAGGA | CCAGGTGTAA | CTATTATTAT | GAATGGAGCA | 240 |
| AATCATAGAA | TGGATGGCTC | AACATATCCA | TTTAATTTAT | TTGGTAATGG | ATGGGAGAAA | 300 |
| CATATGCCAA | AATTAGATCA | ACTACCTATT | AAGGGGATA  | CAATAATAGG | TAATGATGTA | 360 |
| TGGATAGGAA | AAGATGTTGT | AATTATGCCA | GGAGTAAAAA | TCGGGGATGG | TGCAATAGTA | 420 |
| GCTGCTAATT | CTGTTGTTGT | AAAAGATATA | GCGCCATACA | TGTTAGCTGG | AGGAAATCCT | 480 |
| GCTAACGAAA | TAAAACAAAG | ATTTGATCAA | GATACAATAA | ATCAGCTGCT | TGATATAAAA | 540 |
| TGGTGGAATT | GGCCAATAGA | CATTATTAAT | GAGAATATAG | ATAAAATTCT | TGATAATAGC | 600 |
| ATCATTAGAG | AAGTCATATG | GAAAAAATGA | | | | 630 |

(2) INFORMATION FOR SEQ ID NO:174:

(i) SEQUENCE CHARACTERISTICS:
        (A) LENGTH: 1440 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:174:

| | | | | | |
|---|---|---|---|---|---|
| ATGAATATAG | TTGAAAATGA | AATATGTATA | AGAACTTTAA | TAGATGATGA | TTTTCCTTTG | 60 |
| ATGTTAAAAT | GGTTAACTGA | TGAAAGAGTA | TTAGAATTTT | ATGGTGGTAG | AGATAAAAAA | 120 |
| TATACATTAG | AATCATTAAA | AAAACATTAT | ACAGAGCCTT | GGGAAGATGA | AGTTTTTAGA | 180 |
| GTAATTATTG | AATATAACAA | TGTTCCTATT | GGATATGGAC | AAATATATAA | AATGTATGAT | 240 |
| GAGTTATATA | CTGATTATCA | TTATCCAAAA | ACTGATGAGA | TAGTCTATGG | TATGGATCAA | 300 |
| TTTATAGGAG | AGCCAAATTA | TTGGAGTAAA | GGAATTGGTA | CAAGATATAT | TAAATTGATT | 360 |
| TTTGAATTTT | TGAAAAAAGA | AAGAAATGCT | AATGCAGTTA | TTTTAGACCC | TCATAAAAAT | 420 |
| AATCCAAGAG | CAATAAGGGC | ATACCAAAAA | TCTGGTTTTA | GAATTATTGA | AGATTTGCCA | 480 |
| GAACATGAAT | TACACGAGGG | CAAAAAAGAA | GATTGTTATT | TAATGGAATA | TAGATATGAT | 540 |
| GATAATGCCA | CAAATGTTAA | GGCAATGAAA | TATTTAATTG | AGCATTACTT | TGATAATTTC | 600 |
| AAAGTAGATA | GTATTGAAAT | AATCGGTAGT | GGTTATGATA | GTGTGGCATA | TTTAGTTAAT | 660 |
| AATGAATACA | TTTTTAAAAC | AAAATTTAGT | ACTAATAAGA | AAAAAGGTTA | TGCAAAAGAA | 720 |
| AAAGCAATAT | ATAATTTTTT | AAATACAAAT | TTAGAAACTA | ATGTAAAAAT | TCCTAATATT | 780 |
| GAATATTCGT | ATATTAGTGA | TGAATTATCT | ATACTAGGTT | ATAAAGAAAT | TAAAGGAACT | 840 |
| TTTTTAACAC | CAGAAATTTA | TTCTACTATG | TCAGAAGAAG | AACAAAATTT | GTTAAAACGA | 900 |
| GATATTGCCA | GTTTTTTAAG | ACAAATGCAC | GGTTTAGATT | ATACAGATAT | TAGTGAATGT | 960 |
| ACTATTGATA | ATAAACAAAA | TGTATTAGAA | GAGTATATAT | TGTTGCGTGA | AACTATTTAT | 1020 |

```
AATGATTTAA CTGATATAGA AAAAGATTAT ATAGAAAGTT TTATGGAAAG ACTAAATGCA    1080

ACAACAGTTT TTGAGGGTAA AAAGTGTTTA TGCCATAATG ATTTTAGTTG TAATCATCTA    1140

TTGTTAGATG GCAATAATAG ATTAACTGGA ATAATTGATT TTGGAGATTC TGGAATTATA    1200

GATGAATATT GTGATTTTAT ATACTTACTT GAAGATAGTG AAGAAGAAAT AGGAACAAAT    1260

TTTGGAGAAG ATATATTAAG AATGTATGGA AATATAGATA TTGAGAAAGC AAAAGAATAT    1320

CAAGATATAG TTGAAGAATA TTATCCTATT GAAACTATTG TTTATGGAAT TAAAAATATT    1380

AAACAGGAAT TTATCGAAAA TGGTAGAAAA GAAATTTATA AAAGGACTTA TAAAGATTGA    1440

(2) INFORMATION FOR SEQ ID NO:175:

(i) SEQUENCE CHARACTERISTICS:
        (A) LENGTH: 660 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:175:

TTGAATTTAA ACAATGACCA TGGACCTGAT CCCGAAAATA TTTTACCGAT AAAAGGGAAT      60

CGGAATCTTC AATTTATAAA ACCTACTATA ACGAACGAAA ACATTTTGGT GGGGAATAT     120

TCTTATTATG ATAGTAAGCG AGGAGAATCC TTTGAAGATC AAGTCTTATA TCATTATGAA    180

GTGATTGGAG ATAAGTTGAT TATAGGAAGA TTTTGTTCAA TTGGTCCCGG AACAACATTT    240

ATTATGAATG GTGCAAACCA TCGGATGGAT GGATCAACAT ATCCTTTTCA TCTATTCAGG    300

ATGGGTTGGG AGAAGTATAT GCCTTCCTTA AAAGATCTTC CCTTGAAAGG GGACATTGAA    360

ATTGGAAATG ATGTATGGAT AGGTAGAGAT GTAACCATTA TGCCTGGGGT GAAAATTGGG    420

GACGGGGCAA TCATTGCTGC AGAAGCTGTT GTCACAAAGA ATGTTGCTCC CTATTCTATT    480

GTCGGTGGAA ATCCCTTAAA ATTTATAAGA AAAAGGTTTT CTGATGGAGT TATCGAAGAA    540

TGGTTAGCTT TACAATGGTG GAATTTAGAT ATGAAAATTA TTAATGAAAA TCTTCCCTTC    600

ATAATAAATG GAGATATCGA AATGCTGAAG AGAAAAAGAA AACTTCTAGA TGACACTTGA    660

(2) INFORMATION FOR SEQ ID NO:176:

(i) SEQUENCE CHARACTERISTICS:
        (A) LENGTH: 1569 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:176:

ATGAAAATAA TGTTAGAGGG ACTTAATATA AAACATTATG TTCAAGATCG TTTATTGTTG     60

AACATAAATC GCCTAAAGAT TTATCAGAAT GATCGTATTG GTTTAATTGG TAAAAATGGA    120

AGTGGAAAAA CAACGTTACT TCACATATTA TATAAAAAAA TTGTGCCTGA AGAAGGTATT    180

GTAAAACAAT TTTCACATTG TGAACTTATT CCTCAATTGA AGCTCATAGA ATCAACTAAA    240

AGTGGTGGTG AAGTAACACG AAACTATATT CGGCAAGCGC TTGATAAAAA TCCAGAACTG    300

CTATTAGCAG ATGAACCAAC AACTAACTTA GATAATAACT ATATAGAAAA ATTAGAACAG    360

GATTTAAAAA ATTGGCATGG AGCATTTATT ATAGTTTCAC ATGATCGCGC TTTTTTAGAT    420

AACTTGTGTA CTACTATATG GGAAATTGAC GAGGGAAGAA TAACTGAATA TAAGGGGAAT    480

TATAGTAACT ATGTTGAACA AAAAGAATTA GAAAGACATC GAGAAGAATT AGAATATGAA    540
```

```
AAATATGAAA AAGAAAAGAA ACGATTGGAA AAAGCTATAA ATATAAAAGA ACAGAAAGCT      600

CAACGAGCAA CTAAAAAACC GAAAAACTTA AGTTTATCTG AAGGCAAAAT AAAAGGAGCA      660

AAGCCATACT TTGCAGGTAA GCAAAAGAAG TTACGAAAAA CTGTAAAATC TCTAGAAACC      720

AGACTAGAAA AACTTGAAAG CGTCGAAAAG AGAAACGAAC TTCCTCCACT TAAAATGGAT      780

TTAGTGAACT TAGAAAGTGT AAAAAATAGA ACTATAAATAC GTGGTGAAGA TGTCTCGGGT    840

ACAATTGAAG GACGGGTATT GTGGAAAGCA AAAAGTTTTA GTATTCGCGG AGGAGACAAG     900

ATGGCAATTA TCGGATCTAA TGGTACAGGA AGACAACGT TTATTAAAAA AATTGTGCAT      960

GGGAATCCTG GTATTTCATT ATCGCCATCT GTCAAAATCG GTTATTTTAG CCAAAAAATA    1020

GATACATTAG AATTAGATAA GAGCATTTTA GAAAATGTTC AATCTTCTTC ACAACAAAAT    1080

GAAACTCTTA TTCGAACTAT TCTAGCTAGA ATGCATTTTT TTAGAGATGA TGTTTATAAA    1140

CCAATAAGTG TCTTAAGTGG TGGAGAGCGA GTTAAAGTAG CACTAACTAA AGTATTCTTA    1200

AGTGAAGTTA ATACGTTGGT ACTAGATGAA CCAACAAACT TTCTTGATAT GGAAGCTATA    1260

GAGGCGTTTG AATCTTTGTT AAAGGAATAT AATGGCAGTA TAATCTTTGT ATCTCACGAT    1320

CGTAAATTTA TCGAAAAAGT AGCCACTCGA ATAATGACAA TTGATAATAA AGAAATAAAA    1380

ATATTTGATG GCACATATGA ACAATTTAAA CAAGCTGAAA AGCCAACAAG GAATATTAAA    1440

GAAGATAAAA AACTTTTACT TGAGACAAAA ATTACAGAAG TACTCAGTCG ATTGAGTATT    1500

GAACCTTCGG AAGAATTAGA ACAAGAGTTT CAAAACTTAA TAAATGAAAA AAGAAATTTG    1560

GATAAATAA                                                            1569

(2) INFORMATION FOR SEQ ID NO:177:

(i) SEQUENCE CHARACTERISTICS:
            (A) LENGTH: 1467 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:177:

ATGGAACAAT ATACAATTAA ATTTAACCAA ATCAATCATA AATTGACAGA TTTACGATCA       60

CTTAACATCG ATCATCTTTA TGCTTACCAA TTTGAAAAAA TAGCACTTAT TGGGGGTAAT      120

GGTACTGGTA AAACCACATT ACTAAATATG ATTGCTCAAA AACAAAACC AGAATCTGGA      180

ACAGTTGAAA CGAATGGCGA AATTCAATAT TTTGAACAGC TTAACATGGA TGTGGAAAAT     240

GATTTTAACA CGTTAGACGG TAGTTTAATG AGTGAACTCC ATATACCTAT GCATACAACC     300

GACAGTATGA GTGGTGGTGA AAAAGCAAAA TATAAATTAC GTAATGTCAT ATCAAATTAT     360

AGTCCGATAT TACTTTTAGA TGAACCTACA AATCACTTGG ATAAAATTGG TAAAGATTAT    420

CTGAATAATA TTTTAAAATA TTACTATGGT ACTTTAATTA TAGTAAGTCA CGATAGAGCA     480

CTTATAGACC AAATTGCTGA CACAATTTGG GATATACAAG AAGATGGCAC AATAAGAGTG    540

TTTAAAGGTA ATTACACACA GTATCAAAAT CAATATGAAC AAGAACAGTT AGAACAACAA    600

CGTAAATATG AACAGTATAT AAGTGAAAAA CAAAGATTGT CCCAAGCCAG TAAAGCTAAA    660

CGAAATCAAG CGCAACAAAT GGCACAAGCA TCATCAAAAC AAAAAAATAA AAGTATAGCA    720

CCAGATCGTT TAAGTGCATC AAAAGAAAAA GGCACGGTTG AGAAGGCTGC TCAAAAACAA    780

GCTAAGCATA TTGAAAAAAG AATGGAACAT TTGGAAGAAG TTGAAAAACC ACAAAGTTAT    840

CATGAATTCA ATTTTCCACA AAATAAAATT TATGATATCC ATAATAATTA TCCAATCATT    900
```

-continued

| | | | | | | |
|---|---|---|---|---|---|---|
|GCACAAAATC|TAACATTGGT|TAAAGGAAGT|CAAAAACTGC|TAACACAAGT|ACGATTCCAA|960|
|ATACCATATG|GCAAAAATAT|AGCGCTCGTA|GGTGCAAATG|GTGTAGGTAA|GACAACTTTA|1020|
|CTTGAAGCTA|TTTACCACCA|AATAGAGGGA|ATTGATTGTT|CTCCTAAAGT|GCAAATGGCA|1080|
|TACTATCGTC|AACTTGCTTA|TGAAGACATG|CGTGACGTTT|CATTATTGCA|ATATTTAATG|1140|
|GATGAAACGG|ATTCATCAGA|ATCATTCAGT|AGAGCTATTT|TAAATAACTT|GGGTTTAAAT|1200|
|GAAGCACTTG|AGCGTTCTTG|TAATGTTTTG|AGTGGTGGGG|AAAGAACGAA|ATTATCGTTA|1260|
|GCAGTATTAT|TTTCAACGAA|AGCGAATATG|TTAATTTTGG|ATGAACCAAC|TAATTTTTA|1320|
|GATATTAAAA|CATTAGAAGC|ATTAGAAATG|TTTATGAATA|AATATCCTGG|AATCATTTTG|1380|
|TTTACATCAC|ATGATACAAG|GTTTGTTAAA|CATGTATCAG|ATAAAAAATG|GGAATTAACA|1440|
|GGACAATCTA|TTCATGATAT|AACTTAA| | | |1467|

SPECIES SPECIFIC AND UNIVERSAL DNA PROBES AND AMPLIFICATION PRIMERS TO RAPIDLY DETECT AND IDENTIFY COMMON BACTERIAL PATHOGENS AND ASSOCIATED ANTIBIOTIC RESISTANCE GENES FROM CLINICAL SPECIMENS FOR ROUTINE DIAGNOSIS IN MICROBIOLOGY LABORATORIES

This application is a continuation-in-part of U.S. Ser. No. 08/304,732, filed Sep. 12, 1994.

BACKGROUND OF THE INVENTION

Classical identification of bacteria

Bacteria are classically identified by their ability to utilize different substrates as a source of carbon and nitrogen through the use of biochemical tests such as the API20E™ system. Susceptibility testing of Gram negative bacilli has progressed to microdilution tests. Although the API and the microdilution systems are cost-effective, at least two days are required to obtain preliminary results due to the necessity of two successive overnight incubations to isolate and identify the bacteria from the specimen. Some faster detection methods with sophisticated and expensive apparatus have been developed. For example, the fastest identification system, the autoSCAN-Walk-Away™ system identifies both Gram negative and Gram positive from isolated bacterial colonies in 2 hours and susceptibility patterns to antibiotics in only 7 hours. However, this system has an unacceptable margin of error, especially with bacterial species other than Enterobacteriaceae (York et al., 1992. J. Clin. Microbiol. 30:2903–2910). Nevertheless, even this fastest method requires primary isolation of the bacteria as a pure culture, a process which takes at least 18 hours if there is a pure culture or 2 to 3 days if there is a mixed culture.

Urine specimens

A large proportion (40–50%) of specimens received in routine diagnostic microbiology laboratories for bacterial identification are urine specimens (Pezzlo, 1988, Clin. Microbiol. Rev. 1:268–280). Urinary tract infections (UTI) are extremely common and affect up to 20% of women and account for extensive morbidity and increased mortality among hospitalized patients (Johnson and Stamm, 1989; Ann. Intern. Med. 111:906–917). UTI are usually of bacterial etiology and require antimicrobial therapy. The Gram negative bacillus *Escherichia coli* is by far the most prevalent urinary pathogen and accounts for 50 to 60% of UTI (Pezzlo, 1988, op. cit.). The prevalence for bacterial pathogens isolated from urine specimens observed recently at the "Centre Hospitalier de l'Université Laval (CHUL)" is given in Tables 1 and 2.

Conventional pathogen identification in urine specimens. The search for pathogens in urine specimens is so preponderant in the routine microbiology laboratory that a myriad of tests have been developed. The gold standard is still the classical semi-quantitative plate culture method in which a calibrated loop of urine is streaked on plates and incubated for 18–24 hours. Colonies are then counted to determine the total number of colony forming units (CFU) per liter of urine. A bacterial UTI is normally associated with a bacterial count of $\geq 10^7$ CFU/L in urine. However, infections with less than $10^7$ CFU/L in urine are possible, particularly in patients with a high incidence of diseases or those catheterized (Stark and Maki, 1984, N. Engl. J. Med. 311:560–564). Importantly, close to 80% of urine specimens tested are considered negative (<$10^7$ CFU/L; Table 3).

Accurate and rapid urine screening methods for bacterial pathogens would allow a faster identification of negative results and a more efficient clinical investigation of the patient. Several rapid identification methods (Uriscreen™, UTIscreen™, Flash Track™ DNA probes and others) were recently compared to slower standard biochemical methods which are based on culture of the bacterial pathogens. Although much faster, these rapid tests showed low sensitivities and specificities as well as a high number of false negative and false positive results (Koening et al., 1992. J. Clin. Microbiol. 30:342–345; Pezzlo et al., 1992. J. Clin. Microbiol. 30:640–684).

Urine specimens found positive by culture are further characterized using standard biochemical tests to identify the bacterial pathogen and are also tested for susceptibility to antibiotics.

Any clinical specimens

As with urine specimen which was used here as an example, our probes and amplification primers are also applicable to any other clinical specimens. The DNA-based tests proposed in this invention are superior to standard methods currently used for routine diagnosis in terms of rapidity and accuracy. While a high percentage of urine specimens are negative, in many other clinical specimens more than 95% of cultures are negative (Table 4). These data further support the use of universal probes to screen out the negative clinical specimens. Clinical specimens from organisms other than humans (e.g. other primates, mammals, farm animals or live stocks) may also be used.

Towards the development of rapid DNA-based diagnostic tests

A rapid diagnostic test should have a significant impact on the management of infections. For the identification of pathogens and antibiotic resistance genes in clinical samples, DNA probe and DNA amplification technologies offer several advantages over conventional methods. There is no need for subculturing, hence the organism can be detected directly in clinical samples thereby reducing the costs and time associated with isolation of pathogens. DNA-based technologies have proven to be extremely useful for specific applications in the clinical microbiology laboratory. For example, kits for the detection of fastidious organisms based on the use of hybridization probes or DNA amplification for the direct detection of pathogens in clinical specimens are commercially available (Persing et al, 1993. Diagnostic Molecular Microbiology: Principles and Applications, American Society for Microbiology, Washington, D.C.).

The present invention is an advantageous alternative to the conventional culture identification methods used in hospital clinical microbiology laboratories and in private clinics for routine diagnosis. Besides being much faster, DNA-based diagnostic tests are more accurate than standard biochemical tests presently used for diagnosis because the bacterial genotype (e.g. DNA level) is more stable than the bacterial phenotype (e.g. biochemical properties). The originality of this invention is that genomic DNA fragments (size of at least 100 base pairs) specific for 12 species of commonly encountered bacterial pathogens were selected from genomic libraries or from data banks. Amplification primers or oligonucleotide probes (both at least twelve but less than 100 nucleotides in length) which are both derived from the sequence of species-specific DNA fragments identified by hybridization from genomic libraries or from selected data bank sequences are used as a basis to develop diagnostic tests. Oligonucleotide primers and probes for the detection of commonly encountered and clinically important bacterial resistance genes are also included. For example, Annexes I and II present a list of suitable oligonucleotide probes and PCR primers which were all derived from the species-specific DNA fragments selected from genomic libraries or from data bank sequences. It is clear to the individual skilled in the art that oligonucleotide sequences appropriate for the specific detection of the above bacterial species other than those listed in Annexes 1 and 2 may be derived from the species-specific fragments or from the selected data bank sequences. For example, the oligonucleotides may be shorter or longer than the ones we have chosen and may be selected anywhere else in the identified species-specific sequences or selected data bank sequences. Alternatively, the oligonucleotides may be designed for use in amplification methods other than PCR. Consequently, the core of this invention is the identification of species-specific genomic DNA fragments from bacterial genomic DNA libraries and the selection of genomic DNA fragments from data bank sequences which are used as a source of species-specific and ubiquitous oligonucleotides. Although the selection of oligonucleotides suitable for diagnostic purposes from the sequence of the species-specific fragments or from the selected data bank sequences requires much effort it is quite possible for the individual skilled in the art to derive from our fragments or selected data bank sequences suitable oligonucleotides which are different from the ones we have selected and tested as examples (Annexes I and II).

Others have developed DNA-based tests for the detection and identification of some of the bacterial pathogens for which we have identified species-specific sequences (PCT patent application Serial No. WO 93/03186). However, their strategy was based on the amplification of the highly conserved 16S rRNA gene followed by hybridization with internal species-specific oligonucleotides. The strategy from this invention is much simpler and more rapid because it allows the direct amplification of species-specific targets using oligonucleotides derived from the species-specific bacterial genomic DNA fragments.

Since a high percentage of clinical specimens are negative, oligonucleotide primers and probes were selected from the highly conserved 16S or 23S rRNA genes to detect all bacterial pathogens possibly encountered in clinical specimens in order to determine whether a clinical specimen is infected or not. This strategy allows rapid screening out of the numerous negative clinical specimens submitted for bacteriological testing.

We are also developing other DNA-based tests, to be performed simultaneously with bacterial identification, to determine rapidly the putative bacterial susceptibility to antibiotics by targeting commonly encountered and clinically relevant bacterial resistance genes. Although the sequences from the selected antibiotic resistance genes are available and have been used to develop DNA-based tests for their detection (Ehrlich and Greenberg, 1994. PCR-based Diagnostics in Infectious Diseases, Blackwell Scientific Publications, Boston, Mass.; Persing et al, 1993. Diagnostic Molecular Microbiology: Principles and Applications, American Society for Microbiology, Washington, D.C.), our approch is innovative as it represents major improvements over current "gold standard" diagnostic methods based on culture of the bacteria because it allows the rapid identification of the presence of a specific bacterial pathogen and evaluation of its susceptibility to antibiotics directly from the clinical specimens within one hour.

We believe that the rapid and simple diagnostic tests not based on cultivation of the bacteria that we are developing will gradually replace the slow conventional bacterial identification methods presently used in hospital clinical microbiology laboratories and in private clinics. In our opinion, these rapid DNA-based diagnostic tests for severe and common bacterial pathogens and antibiotic resistance will (i) save lives by optimizing treatment, (ii) diminish antibiotic resistance by reducing the use of broad spectrum antibiotics and (iii) decrease overall health costs by preventing or shortening hospitalizations.

SUMMARY OF THE INVENTION

In accordance with the present invention, there is provided sequence from genomic DNA fragments (size of at least 100 base pairs and all described in the sequence listing) selected either by hybridization from genomic libraries or from data banks and which are specific for the detection of commonly encountered bacterial pathogens (i.e. *Escherichia coli, Klebsiella pneumoniae, Pseudomonas aeruginosa, Proteus mirabilis, Streptococcus pneumoniae, Staphylococcus aureus, Staphylococcus epidermidis, Enterococcus faecalis, Staphylococcus saprophyticus, Streptococcus pyogenes, Haemophilus influenzae* and *Moraxella catarrhalis*) in clinical specimens. These bacterial species are associated with approximately 90% of urinary tract infections and with a high percentage of other severe infections including septicemia, meningitis, pneumonia, intraabdominal infections, skin infections and many other severe respiratory tract infections. Overall, the above bacterial species may account for up to 80% of bacterial pathogens isolated in routine microbiology laboratories.

Synthetic oligonucleotides for hybridization (probes) or DNA amplification (primers) were derived from the above species-specific DNA fragments (ranging in sizes from 0.25 to 5.0 kilobase pairs (kbp)) or from selected data bank sequences (GenBank and EMBL). Bacterial species for which some of the oligonucleotide probes and amplification primers were derived from selected data bank sequences are *Escherichia coli, Enterococcus faecalis, Streptococcus pyogenes* and *Pseudomonas aeruginosa*. The person skilled in the art understands that the important innovation in this invention is the identification of the species-specific DNA fragments selected either from bacterial genomic libraries by hybridization or from data bank sequences. The selection of oligonucleotides from these fragments suitable for diagnostic purposes is also innovative. Specific and ubiquitous oligonucleotides different from the ones tested in the practice are considered as embodiments of the present invention.

The development of hybridization (with either fragment or oligonucleotide probes) or of DNA amplification protocols for the detection of pathogens from clinical specimens renders possible a very rapid bacterial identification. This will greatly reduce the time currently required for the identification of pathogens in the clinical laboratory since these technologies can be applied for bacterial detection and identification directly from clinical specimens with minimum pretreatment of any biological specimens to release bacterial DNA. In addition to being 100% specific, probes and amplification primers allow identification of the bacterial species directly from clinical specimens or, alternatively, from an isolated colony. DNA amplification assays have the added advantages of being faster and more sensitive than hybridization assays, since they allow rapid and exponential in vitro replication of the target segment of DNA from the bacterial genome. Universal probes and amplification primers selected from the 16S or 23S rRNA genes highly conserved among bacteria, which permit the detection of any bacterial pathogens, will serve as a procedure to screen out the numerous negative clinical specimens received in diagnostic laboratories. The use of oligonucleotide probes or primers complementary to characterized bacterial genes encoding resistance to antibiotics to identify commonly encountered and clinically important resistance genes is also under the scope of this invention.

DETAILED DESCRIPTION OF THE INVENTION

Development of species-specific DNA probes

DNA fragment probes were developed for the following bacterial species: *Escherichia coli, Klebsiella pneumoniae, Pseudomonas aeruginosa, Proteus mirabilis, Streptococcus pneumoniae, Staphylococcus aureus, Staphylococcus epidermidis, Staphylococcus saprophyticus, Haemophilus influenzae* and *Moraxella catarrhalis*. (For *Enterococcus faecalis* and *Streptococcus pyogenes*, oligonucleotide sequences were exclusively derived from selected data bank sequences). These species-specific fragments were selected from bacterial genomic libraries by hybridization to DNA from a variety of Gram positive and Gram negative bacterial species (Table 5).

The chromosomal DNA from each bacterial species for which probes were sought was isolated using standard methods. DNA was digested with a frequently cutting restriction enzyme such as Sau3AI and then ligated into the bacterial plasmid vector pGEM3Zf (Promega) linearized by appropriate restriction endonuclease digestion. Recombinant plasmids were then used to transform competent *E. coli* strain DH5α thereby yielding a genomic library. The plasmid content of the transformed bacterial cells was analyzed using standard methods. DNA fragments of target bacteria ranging in size from 0.25 to 5.0 kilobase pairs (kbp) were cut out from the vector by digestion of the recombinant plasmid with various restriction endonucleases. The insert was separated from the vector by agarose gel electrophoresis and purified in low melting point agarose gels. Each of the purified fragments of bacterial genomic DNA was then used as a probe for specificity tests.

For each given species, the gel-purified restriction fragments of unknown coding potential were labeled with the radioactive nucleotide $\alpha$-$^{32}$P(dATP) which was incorporated into the DNA fragment by the random priming labeling reaction. Non-radioactive modified nucleotides could also be incorporated into the DNA by this method to serve as a label.

Each DNA fragment probe (i.e. a segment of bacterial genomic DNA of at least 100 bp in length cut out from clones randomly selected from the genomic library) was then tested for its specificity by hybridization to DNAs from a variety of bacterial species (Table 5). The double-stranded labeled DNA probe was heat-denatured to yield labeled single-stranded DNA which could then hybridize to any single-stranded target DNA fixed onto a solid support or in solution. The target DNAs consisted of total cellular DNA from an array of bacterial species found in clinical samples (Table 5). Each target DNA was released from the bacterial cells and denatured by conventional methods and then irreversibly fixed onto a solid support (e.g. nylon or nitrocellulose membranes) or free in solution. The fixed single-stranded target DNAs were then hybridized with the single-stranded probe. Pre-hybridization, hybridization and post-hybridization conditions were as follows: (i) Pre-hybridization; in 1 M NaCl+10% dextran sulfate+1% SDS (sodium dodecyl sulfate)+1 μg/ml salmon sperm DNA at 65° C. for 15 min. (ii) Hybridization; in fresh pre-hybridization solution containing the labeled probe at 65° C. overnight. (iii) Post-hybridization; washes twice in 3× SSC containing 1% SDS (1× SSC is 0.15M NaCl, 0.015M NaCitrate) and twice in 0.1× SSC containing 0.1% SDS; all washes were at 65° C. for 15 min. Autoradiography of washed filters allowed the detection of selectively hybridized probes. Hybridization of the probe to a specific target DNA indicated a high degree of similarity between the nucleotide sequence of these two DNAs.

Species-specific DNA fragments selected from various bacterial genomic libraries ranging in size from 0.25 to 5.0 kbp were isolated for 10 common bacterial pathogens (Table 6) based on hybridization to chromosomal DNAs from a variety of bacteria performed as described above. All of the bacterial species tested (66 species listed in Table 5) were likely to be pathogens associated with common infections or potential contaminants which can be isolated from clinical specimens. A DNA fragment probe was considered specific only when it hybridized solely to the pathogen from which it was isolated. DNA fragment probes found to be specific were subsequently tested for their ubiquity (i.e. ubiquitous probes recognized most isolates of the target species) by hybridization to bacterial DNAs from approximately 10 to 80 clinical isolates of the species of interest (Table 6). The DNAs were denatured, fixed onto nylon membranes and hybridized as described above.

Sequencing of the species-specific fragment probes

The nucleotide sequence of the totality or of a portion of the species-specific DNA fragments isolated (Table 6) was determined using the dideoxynucleotide termination sequencing method which was performed using Sequenase (USB Biochemicals) or T7 DNA polymerase (Pharmacia). These nucleotide sequences are shown in the sequence listing. Alternatively, sequences selected from data banks (GenBank and EMBL) were used as sources of oligonucleotides for diagnostic purposes for *Escherichia coli, Enterococcus faecalis, Streptococcus pyogenes* and *Pseudomonas aeruginosa*. For this strategy, an array of suitable oligonucleotide primers or probes derived from a variety of genomic DNA fragments (size of more than 100 bp) selected from data banks was tested for their specificity and ubiquity in PCR and hybridization assays as described later. It is important to note that the data bank sequences were selected based on their potential of being species-specific according to available sequence information. Only data bank sequences from which species-specific oligonucleotides could be derived are included in this invention.

Oligonucleotide probes and amplification primers derived from species-specific fragments selected from the genomic libraries or from data bank sequences were synthesized using an automated DNA synthesizer (Millipore). Prior to synthesis, all oligonucleotides (probes for hybridization and primers for DNA amplification) were evaluated for their suitability for hybridization or DNA amplification by polymerase chain reaction (PCR) by computer analysis using standard programs (e.g. Genetics Computer Group (GCG) and Oligo™ 4.0 (National Biosciences)). The potential suitability of the PCR primer pairs was also evaluated prior to the synthesis by verifying the absence of unwanted features such as long stretches of one nucleotide, a high proportion of G or C residues at the 3' end and a 3'-terminal T residue (Persing et al, 1993. Diagnostic Molecular Microbiology: Principles and Applications, American Society for Microbiology, Washington, D.C.).

Hybridization with oligonucleotide probes

In hybridization experiments, oligonucleotides (size of at least twelve but not less than 100 nucleotides) have some advantages over DNA fragment probes for the detection of bacteria such as ease of preparation in large quantities, consistency in results from batch to batch and chemical stability. Briefly, for the hybridizations, oligonucleotides were 5' end-labeled with the radionucleotide γ³²P(ATP) using T4 polynucleotide kinase (Pharmacia). The unincorporated radionucleotide was removed by passing the labeled single-stranded oligonucleotide through a Sephadex G50 column. Alternatively, oligonucleotides were labeled with biotin, either enzymatically at their 3' ends or incorporated directly during synthesis at their 5' ends, or with digoxigenin. It will be appreciated by the person skilled in the art that labeling means other than the three above labels may be used.

The target DNA was denatured, fixed onto a solid support and hybridized as previously described for the DNA fragment probes. Conditions for pre-hybridization and hybridization were as described earlier. Post-hybridization washing conditions were as follows: twice in 3× SSC containing 1% SDS, twice in 2× SSC containing 1% SDS and twice in 1× SSC containing 1% SDS (all of these washes were at 65° C. for 15 min), and a final wash in 0.1× SSC containing 1% SDS at 25° C. for 15 min. For probes labeled with radioactive labels the detection of hybrids was by autoradiography as described earlier. For non-radioactive labels detection may be colorimetric or by chemiluminescence.

The oligonucleotide probes may be derived from either strand of the duplex DNA. The probes may consist of the bases A, G, C, or T or analogs. The probes may be of any suitable length and may be selected anywhere within the species-specific genomic DNA fragments selected from the genomic libraries or from data bank sequences.

DNA amplification

For DNA amplification by the widely used PCR (polymerase chain reaction) method, primer pairs were derived either from the sequenced species-specific DNA fragments or from data bank sequences or, alternatively, were shortened versions of oligonucleotide probes. Prior to synthesis, the potential primer pairs were analyzed by using the program Oligo™ 4.0 (National Biosciences) to verify that they are likely candidates for PCR amplifications.

During DNA amplification by PCR, two oligonucleotide primers binding respectively to each strand of the denatured double-stranded target DNA from the bacterial genome are used to amplify exponentially in vitro the target DNA by successive thermal cycles allowing denaturation of the DNA, annealing of the primers and synthesis of new targets at each cycle (Persing et al, 1993. Diagnostic Molecular Microbiology: Principles and Applications, American Society for Microbiology, Washington, D.C.). Briefly, the PCR protocols were as follows. Clinical specimens or bacterial colonies were added directly to the 50 μL PCR reaction mixtures containing 50 mM KCl, 10 mM Tris-HCl pH 8.3, 2.5 mM MgCl$_2$, 0.4 μM of each of the two primers, 200 μM of each of the four dNTPs and 1.25 Units of Taq DNA polymerase (Perkin Elmer). PCR reactions were then subjected to thermal cycling (3 min at 95° C. followed by 30 cycles of 1 second at 95° C. and 1 second at 55° C.) using a Perkin Elmer 480™ thermal cycler and subsequently analyzed by standard ethidium bromide-stained agarose gel electrophoresis. It is clear that other methods for the detection of specific amplification products, which may be faster and more practical for routine diagnosis, may be used. Such methods may be based on the detection of fluorescence after amplification (e.g. TaqMan™ system from Perkin Elmer or Amplisensor™ from Biotronics) or liquid hybridization with an oligonucleotide probe binding to internal sequences of the specific amplification product. These novel probes can be generated from our species-specific fragment probes. Methods based on the detection of fluorescence are particularly promising for utilization in routine diagnosis as they are, very rapid and quantitative and can be automated.

To assure PCR efficiency, glycerol or dimethyl sulfoxide (DMSO) or other related solvents, can be used to increase the sensitivity of the PCR and to overcome problems associated with the amplification of target with a high GC content or with strong secondary structures. The concentration ranges for glycerol and DMSO are 5–15% (v/v) and 3–10% (v/v), respectively. For the PCR reaction mixture, the concentration ranges for the amplification primers and the MgCl$_2$ are 0.1–1.0 μM and 1.5–3.5 mM, respectively. Modifications of the standard PCR protocol using external and nested primers (i.e. nested PCR) or using more than one primer pair (i.e. multiplex PCR) may also be used (Persing et al, 1993. Diagnostic Molecular Microbiology: Principles and Applications, American Society for Microbiology, Washington, D.C.). For more details about the PCR protocols and amplicon detection methods see examples 7 and 8.

The person skilled in the art of DNA amplification knows the existence of other rapid amplification procedures such as ligase chain reaction (LCR), transcription-based amplification systems (TAS), self-sustained sequence replication (3SR), nucleic acid sequence-based amplification (NASBA), strand displacement amplification (SDA) and branched DNA (bDNA) (Persing et al, 1993. Diagnostic Molecular Microbiology: Principles and Applications, American Society for Microbiology, Washington, D.C.). The scope of this invention is not limited to the use of amplification by PCR, but rather includes the use of any rapid nucleic acid amplification methods or any other procedures which may be used to increase rapidity and sensitivity of the tests. Any oligonucleotides suitable for the amplification of nucleic acid by approaches other than PCR and derived from the species-specific fragments and from selected antibiotic resistance gene sequences included in this document are also under the scope of this invention.

Specificity and ubiquity tests for oligonucleotide probes and primers

The specificity of oligonucleotide probes, derived either from the sequenced species-specific fragments or from data bank sequences, was tested by hybridization to DNAs from the array of bacterial species listed in Table 5 as previously described. Oligonucleotides found to be specific were subsequently tested for their ubiquity by hybridization to bacterial DNAs from approximately 80 isolates of the target species as described for fragment probes. P robes were considered ubiquitous when they hybridized specifically with the DNA from at least 80% of the isolates. Results for specificity and ubiquity tests with the oligonucleotide probes are summarized in Table 6. The specificity and ubiquity of the amplification primer pairs were tested directly from cultures (see example 7) of the same bacterial strains. For specificity and ubiquity tests, PCR assays were performed directly from bacterial colonies of approximately 80 isolates of the target species. Results are summarized in Table 7. All specific and ubiquitous oligonucleotide probes and amplification primers for each of the 12 bacterial species investigated are listed in Annexes I and II, respectively. Divergence in the sequenced DNA fragments can occur and, insofar as the divergence of these sequences or a part thereof does not affect the specificity of the probes or amplification primers, variant bacterial DNA is under the scope of this invention.

Universal bacterial detection

In the routine microbiology laboratory a high percentage of clinical specimens sent for bacterial identification is negative (Table 4). For example, over a 2 year period, around 80% of urine specimens received by the laboratory at the "Centre Hospitalier de l'Université Laval (CHUL)" were negative (i.e. <10$^7$ CFU/L) (Table 3). Testing clinical samples with universal probes or universal amplification primers to detect the presence of bacteria prior to specific identification and screen out the numerous negative specimens is thus useful as it saves costs and may rapidly orient the clinical management of the patients. Several oligonucleotides and amplification primers were therefore synthesized from highly conserved portions of bacterial 16S or 23S ribosomal RNA gene sequences available in data banks (Annexes III and IV). In hybridization tests, a pool of seven oligonucleotides (Annex I; Table 6) hybridized strongly to DNA from all bacterial species listed in Table 5. This pool of universal probes labeled with radionucleotides or with any other modified nucleotides is consequently very useful for detection of bacteria in urine samples with a sensitivity range of $\geq 10^7$ CFU/L. These probes can also be applied for bacterial detection in other clinical samples.

Amplification primers also derived from the sequence of highly conserved ribosomal RNA genes were used as an alternative strategy for universal bacterial detection directly from clinical specimens (Annex IV; Table 7). The DNA amplification strategy was developed to increase the sensitivity and the rapidity of the test. This amplification test was ubiquitous since it specifically amplified DNA from 23 different bacterial species encountered in clinical specimens.

Well-conserved bacterial genes other than ribosomal RNA genes could also be good candidates for universal bacterial detection directly from clinical specimens. Such genes may be associated with processes essential for bacterial survival (e.g. protein synthesis, DNA synthesis, cell division or DNA repair) and could therefore be highly conserved during evolution. We are working on these candidate genes to develop new rapid tests for the universal detection of bacteria directly from clinical specimens.

Antibiotic resistance genes

Antimicrobial resistance complicates treatment and often leads to therapeutic failures. Furthermore, overuse of antibiotics inevitably leads to the emergence of bacterial resistance. Our goal is to provide the clinicians, within one hour, the needed information to prescribe optimal treatments. Besides the rapid identification of negative clinical specimens with DNA-based tests for universal bacterial detection and the identification of the presence of a specific pathogen in the positive specimens with DNA-based tests for specific bacterial detection, the clinicians also need timely information about the ability of the bacterial pathogen to resist antibiotic treatments. We feel that the most efficient strategy to evaluate rapidly bacterial resistance to antimicrobials is to detect directly from the clinical specimens the most common and important antibiotic resistance genes (i.e. DNA-based tests for the detection of antibiotic resitance genes). Since the sequence from the most important and common bacterial antibiotic resistance genes are available from data banks, our strategy is to use the sequence from a portion or from the entire gene to design specific oligonucleotides which will be used as a basis for the development of rapid DNA-based tests. The sequence from the bacterial antibiotic resistance genes selected on the basis of their clinical relevance (i.e. high incidence and importance) is given in the sequence listing. Table 8 summarizes some characteristics of the selected antibiotic resistance genes.

EXAMPLES

The following examples are intended to be illustrative of the various methods and compounds of the invention.

Example 1

Isolation and cloning of fragments. Genomic DNAs from *Escherichia coli* strain ATCC 25922, *Klebsiella pneumoniae* strain CK2, *Pseudomonas aeruginosa* strain ATCC 27853, *Proteus mirabilis* strain ATCC 35657, *Streptococcus pneumoniae* strain ATCC 27336, *Staphylococcus aureus* strain ATCC 25923, *Staphylococcus epidermidis* strain ATCC 12228, *Staphylococcus saprophyticus* strain ATCC 15305, *Haemophilus influenzae* reference strain Rd and *Moraxella catarrhalis* strain ATCC 53879 were prepared using standard procedures. It is understood that the bacterial genomic DNA may have been isolated from strains other than the ones mentioned above. (For *Enterococcus faecalis* and *Streptococcus pyogenes* oligonucleotide sequences were derived exclusively from data banks). Each DNA was digested with a restriction enzyme which frequently cuts DNA such as Sau3AI. The resulting DNA fragments were ligated into a plasmid vector (pGEM3Zf) to create recombinant plasmids and transformed into competent *E. coli* cells (DH5α). It is understood that the vectors and corresponding competent cells should not be limited to the ones herein above specifically exemplified. The objective of obtaining recombinant plasmids and transformed cells is to provide an easily reproducible source of DNA fragments useful as probes. Therefore, insofar as the inserted fragments are specific and selective for the target bacterial DNA, any recombinant plasmids and corresponding transformed host cells are under the scope of this invention. The plasmid content of the transformed bacterial cells was analyzed using standard methods. DNA fragments from target bacteria ranging in size from 0.25 to 5.0 kbp were cut out from the vector by digestion of the recombinant plasmid with various restriction endonucleases. The insert was separated from the vector by agarose gel electrophoresis and purified in a low melting point agarose gel. Each of the purified fragments was then used for specificity tests.

Labeling of DNA fragment probes. The label used was $\alpha^{32}$P(dATP), a radioactive nucleotide which can be incorporated enzymatically into a double-stranded DNA molecule. The fragment of interest is first denatured by heating at 95° C. for 5 min, then a mixture of random primers is allowed to anneal to the strands of the fragments. These primers, once annealed, provide a starting point for synthesis of DNA. DNA polymerase, usually the Klenow fragment, is provided along with the four nucleotides, one of which is radioactive. When the reaction is terminated, the mixture of new DNA molecules is once again denatured to provide radioactive single-stranded DNA molecules (i.e. the probe). As mentioned earlier, other modified nucleotides may be used to label the probes.

Specificity and ubiquity tests for the DNA fragment probes. Species-specific DNA fragments ranging in size from 0.25 to 5.0 kbp were isolated for 10 common bacterial pathogens (Table 6) based on hybridization to chromosomal DNAs from a variety of bacteria. Samples of whole cell DNA for each bacterial strain listed in Table 5 were transferred onto a nylon membrane using a dot blot apparatus, washed and denatured before being irreversibly fixed. Hybridization conditions were as described earlier. A DNA fragment probe was considered specific only when it hybridized solely to the pathogen from which it was isolated. Labeled DNA fragments hybridizing specifically only to target bacterial species (i.e. specific) were then tested for their ubiquity by hybridization to DNAs from approximately 10 to 80 isolates of the species of interest as described earlier. The conditions for pre-hybridization, hybridization and post-hybridization washes were as described earlier. After autoradiography (or other detection means appropriate for the non-radioactive label used), the specificity of each individual probe can be determined. Each probe found to be specific (i.e. hybridizing only to the DNA from the bacterial species from which it was isolated) and ubiquitous (i.e. hybridizing to most isolates of the target species) was kept for further experimentations.

Example 2

Same as example 1 except that testing of the strains is by colony hybridization. The bacterial strains were inoculated onto a nylon membrane placed on nutrient agar. The membranes were incubated at 37° C. for two hours and then bacterial lysis and DNA denaturation were carried out according to standard procedures. DNA hybridization was performed as described earlier.

Example 3

Same as example 1 except that bacteria were detected directly from clinical samples. Any biological samples were loaded directly onto a dot blot apparatus and cells were lysed in situ for bacterial detection. Blood samples should be heparizined in order to avoid coagulation interfering with their convenient loading on a dot blot apparatus.

Example 4

Nucleotide sequencing of DNA fragments. The nucleotide sequence of the totality or a portion of each fragment found to be specific and ubiquitous (Example 1) was determined using the dideoxynucleotide termination sequencing method (Sanger et al., 1977, Proc. Natl. Acad. Sci. USA. 74:5463–5467). These DNA sequences are shown in the sequence listing. Oligonucleotide probes and amplification primers were selected from these nucleotide sequences, or alternatively, from selected data banks sequences and were then synthesized on an automated Biosearch synthesizer (Millipore™) using phosphoramidite chemistry.

Labeling of oligonucleotides. Each oligonucleotide was 5' end-labeled with $\gamma^{32}$P-ATP by the T4 polynucleotide kinase (Pharmacia) as described earlier. The label could also be non-radioactive.

Specificity test for oligonucleotide probes. All labeled oligonucleotide probes were tested for their specificity by hybridization to DNAs from a variety of Gram positive and Gram negative bacterial species as described earlier. Species-specific probes were those hybridizing only to DNA from the bacterial species from which it was isolated. Oligonucleotide probes found to be specific were submitted to ubiquity tests as follows.

Ubiquity test for oligonucleotide probes. Specific oligonucleotide probes were then used in ubiquity tests with approximately 80 strains of the target species. Chromosomal DNAs from the isolates were transferred onto nylon membranes and hybridized with labeled oligonucleotide probes as described for specificity tests. The batteries of approximately 80 isolates constructed for each target species contain reference ATCC strains as well as a variety of clinical isolates obtained from various sources. Ubiquitous probes were those hybridizing to at least 80% of DNAs from the battery of clinical isolates of the target species. Examples of specific and ubiquitous oligonucleotide probes are listed in Annex 1.

Example 5

Same as example 4 except that a pool of specific oligonucleotide probes is used for bacterial identification (i) to increase sensitivity and assure 100% ubiquity or (ii) to identify simultaneously more than one bacterial species. Bacterial identification could be done from isolated colonies or directly from clinical specimens.

Example 6

PCR amplification. The technique of PCR was used to increase sensitivity and rapidity of the tests. The PCR primers used were often shorter derivatives of the extensive sets of oligonucleotides previously developed for hybridization assays (Table 6). The sets of primers were tested in PCR assays performed directly from a bacterial colony or from a bacterial suspension (see Example 7) to determine their specificity and ubiquity (Table 7). Examples of specific and ubiquitous PCR primer pairs are listed in annex II.

Specificity and ubiquity tests for amplification primers. The specificity of all selected PCR primer pairs was tested against the battery of Gram negative and Gram positive bacteria used to test the oligonucleotide probes (Table 5). Primer pairs found specific for each species were then tested for their ubiquity to ensure that each set of primers could amplify at least 80% of DNAs from a battery of approximately 80 isolates of the target species. The batteries of isolates constructed for each species contain reference ATCC strains and various clinical isolates representative of the clinical diversity for each species.

Standard precautions to avoid false positive PCR results should be taken. Methods to inactivate PCR amplification products such as the inactivation by uracil-N-glycosylase may be used to control PCR carryover.

Example 7

Amplification directly from a bacterial colony or suspension. PCR assays were performed either directly from a bacterial colony or from a bacterial suspension, the latter being adjusted to a standard McFarland 0.5 (corresponds to $1.5 \times 10^8$ bacteria/mL). In the case of direct amplification from a colony, a portion of the colony was transferred directly to a 50 µL PCR reaction mixture (containing 50 mM KCl, 10 mM Tris pH 8.3, 2.5 mM MgCl$_2$, 0.4 µM of each of the two primers, 200 µM of each of the four dNTPs and 1.25 Unit of Taq DNA polymerase (Perkin Elmer)) using a plastic rod. For the bacterial suspension, 4 µL of the cell suspension was added to 46 µL of the same PCR reaction mixture. For both strategies, the reaction mixture was overlaid with 50 µL of mineral oil and PCR amplifications were carried out using an initial denaturation step of 3 min. at 95° C. followed by 30 cycles consisting of a 1 second denaturation step at 95° C. and of a 1 second annealing step at 55° C. in a Perkin Elmer 480™ thermal cycler. PCR amplification products were then analyzed by standard agarose gel (2%) electrophoresis. Amplification products were visualized in agarose gels containing 2.5 µg/mL of ethidium bromide under UV at 254 nm. The entire PCR assay can be completed in approximately one hour.

Alternatively, amplification from bacterial cultures was performed as described above but using a "hot start" protocol. In that case, an initial reaction mixture containing the target DNA, primers and dNTPs was heated at 85° C. prior to the addition of the other components of the PCR reaction mixture. The final concentration of all reagents was as described above. Subsequently, the PCR reactions were submitted to thermal cycling and analysis as described above.

Example 8

Amplification directly from clinical specimens. For amplification from urine specimens, 4 µL of undiluted or diluted (1:10) urine was added directly to 46 μL of the above PCR reaction mixture and amplified as described earlier.

To improve bacterial cell lysis and eliminate the PCR inhibitory effects of clinical specimens, samples were routinely diluted in lysis buffer containing detergent(s). Subsequently, the lysate was added directly to the PCR reaction mixture. Heat treatments of the lysates, prior to DNA amplification, using the thermocycler or a microwave oven could also be performed to increase the efficiency of cell lysis.

Our strategy is to develop rapid and simple protocols to eliminate PCR inhibitory effects of clinical specimens and lyse bacterial cells to perform DNA amplification directly from a variety of biological samples. PCR has the advantage of being compatible with crude DNA preparations. For example, blood, cerebrospinal fluid and sera may be used directly in PCR assays after a brief heat treatment. We intend to use such rapid and simple strategies to develop fast protocols for DNA amplification from a variety of clinical specimens.

Example 9

Detection of antibiotic resistance genes. The presence of specific antibiotic resistance genes which are frequently encountered and clinically relevant is identified using the PCR amplification or hybridization protocols described in previous sections. Specific oligonucleotides used as a basis for the DNA-based tests are selected from the antibiotic resistance gene sequences. These tests can be performed either directly from clinical specimens or from a bacterial colony and should complement diagnostic tests for specific bacterial identification.

Example 10

Same as examples 7 and 8 except that assays were performed by multiplex PCR (i.e. using several pairs of primers in a single PCR reaction) to (i) reach an ubiquity of 100% for the specific target pathogen or (ii) to detect simultaneously several species of bacterial pathogens.

For example, the detection of *Escherichia coli* requires three pairs of PCR primers to assure a ubiquity of 100%. Therefore, a multiplex PCR assay (using the "hot-start" protocol (Example 7)) with those three primer pairs was developed. This strategy was also used for the other bacterial pathogens for which more than one primer pair was required to reach an ubiquity of 100%.

Multiplex PCR assays could also be used to (i) detect simultaneously several bacterial species or, alternatively, (ii) to simultaneously identify the bacterial pathogen and detect specific antibiotic resistance genes either directly from a clinical specimen or from a bacterial colony.

For these applications, amplicon detection methods should be adapted to differentiate the various amplicons produced. Standard agarose gel electrophoresis could be used because it discriminates the amplicons based on their sizes. Another useful strategy for this purpose would be detection using a variety of fluorochromes emitting at different wavelengths which are each coupled with a specific oligonucleotide linked to a fluorescence quencher which is degraded during amplification to release the fluorochrome (e.g. TaqMan™, Perkin Elmer).

Example 11

Detection of amplification products. The person skilled in the art will appreciate that alternatives other than standard agarose gel electrophoresis (Example 7) may be used for the revelation of amplification products. Such methods may be based on the detection of fluorescence after amplification (e.g. Amplisensor™, Biotronics; TaqMan™) or other labels such as biotin (SHARP Signal™ system, Digene Diagnostics). These methods are quantitative and easily automated. One of the amplification primers or an internal oligonucleotide probe specific to the amplicon(s) derived from the species-specific fragment probes is coupled with the fluorochrome or with any other label. Methods based on the detection of fluorescence are particularly suitable for diagnostic tests since they are rapid and flexible as fluorochromes emitting different wavelengths are available (Perkin Elmer).

Example 12

Species-specific, universal and antibiotic resistance gene amplification primers can be used in other rapid amplification procedures such as the ligase chain reaction (LCR), transcription-based amplification systems (TAS), self-sustained sequence replication (3SR), nucleic acid sequence-based amplification (NASBA), strand displacement amplification (SDA) and branched DNA (bDNA) or any other methods to increase the sensitivity of the test. Amplifications can be performed from an isolated bacterial colony or directly from clinical specimens. The scope of this invention is therefore not limited to the use of PCR but rather includes the use of any procedures to specifically identify bacterial DNA and which may be used to increase rapidity and sensitivity of the tests.

Example 13

A test kit would contain sets of probes specific for each bacterium as well as a set of universal probes. The kit is provided in the form of test components, consisting of the set of universal probes labeled with non-radioactive labels as well as labeled specific probes for the detection of each bacterium of interest in specific clinical samples. The kit will also include test reagents necessary to perform the prehybridization, hybridization, washing steps and hybrid detection. Finally, test components for the detection of known antibiotic resistance genes (or derivatives therefrom) will be included. Of course, the kit will include standard samples to be used as negative and positive controls for each hybridization test.

Components to be included in the kits will be adapted to each specimen type and to detect pathogens commonly encountered in that type of specimen. Reagents for the universal detection of bacteria will also be included. Based on the sites of infection, the following kits for the specific detection of pathogens may be developed:

A kit for the universal detection of bacterial pathogens from most clinical specimens which contains sets of probes specific for highly conserved regions of the bacterial genomes.

A kit for the detection of bacterial pathogens retrieved from urine samples, which contains eight specific test components (sets of probes for the detection of *Escherichia coli, Enterococcus faecalis, Klebsiella pneumoniae, Proteus mirabilis, Pseudomonas aeruginosa, Staphylococcus saprophyticus, Staphylococcus aureus* and *Staphylococcus epidermidis*).

A kit for the detection of respiratory pathogens which contains seven specific test components (sets of probes for detecting *Streptococcus pneumoniae, Moraxella catarrhalis, Haemophilus influenzae, Klebsiella* pneumoniae, Pseudomonas aeruginosa, Streptococcus pyogenes and Staphylococcus aureus).

A kit for the detection of pathogens retrieved from blood samples, which contains eleven specific test components (sets of probes for the detection of Streptococcus pneumoniae, Moraxella catarrhalis, Haemophilus influenzae, Proteus mirabilis, Klebsiella pneumoniae, Pseudomonas aeruginosa, Escherichia coli, Enterococcus faecalis, Staphylococcus aureus, Streptococcus pyogenes and Staphylococcus epidermidis).

A kit for the detection of pathogens causing meningitis, which contains four specific test components (sets of probes for the detection of Haemophilus influenzae, Streptococcus pneumoniae, Escherichia coli and Pseudomonas aeruginosa).

A kit for the detection of clinically important antibiotic resistance genes which contains sets of probes for the specific detection of at least one of the 19 following genes associated with bacterial resistance: $bla_{tem}$, $bla_{rob}$, $bla_{shv}$, aadB, aacC1, aacC2, aacC3, aacA4, mecA, vanA, vanH, vanX, satA, aacA-aphD, vat, vga, msrA, sul and int.

Other kits adapted for the detection of pathogens from skin, abdominal wound or any other clinically relevant kits will be developed.

Example 14

Same as example 13 except that the test kits contain all reagents and controls to perform DNA amplification assays. Diagnostic kits will be adapted for amplification by PCR (or other amplification methods) performed directly either from clinical specimens or from a bacterial colony. Components required for universal bacterial detection, bacterial identification and antibiotic resistance genes detection will be included.

Amplification assays could be performed either in tubes or in microtitration plates having multiple wells. For assays in plates, the wells will be coated with the specific amplification primers and control DNAs and the detection of amplification products will be automated. Reagents and amplification primers for universal bacterial detection will be included in kits for tests performed directly from clinical specimens. Components required for bacterial identification and antibiotic resistance gene detection will be included in kits for testing directly from colonies as well as in kits for testing directly from clinical specimens.

The kits will be adapted for use with each type of specimen as described in example 13 for hybridization-based diagnostic kits.

Example 15

It is understood that the use of the probes and amplification primers described in this invention for bacterial detection and identification is not limited to clinical microbiology applications. In fact, we feel that other sectors could also benefit from these new technologies. For example, these tests could be used by industries for quality control of food, water, pharmaceutical products or other products requiring microbiological control. These tests could also be applied to detect and identify bacteria in biological samples from organisms other than humans (e.g. other primates, mammals, farm animals and live stocks). These diagnostic tools could also be very useful for research purposes including clinical trials and epidemiological studies.

TABLE 1

Distribution of urinary isolates from positive urine samples ($\geq 10^7$ CFU/L) at the Centre Hospitalier de l'Université Laval (CHUL) for the 1992–1994 period.

| | % of isolates | | | |
|---|---|---|---|---|
| Organisms | Nov 92 n = 267[a] | April 93 n = 265 | July 93 n = 238 | Jan 94 n = 281 |
| Escherichia coli | 53.2 | 51.7 | 53.8 | 54.1 |
| Enterococcus faecalis | 13.8 | 12.4 | 11.7 | 11.4 |
| Klebsiella pneumoniae | 6.4 | 6.4 | 5.5 | 5.3 |
| Staphylococcus epidermidis | 7.1 | 7.9 | 3.0 | 6.4 |
| Proteus mirabilis | 2.6 | 3.4 | 3.8 | 2.5 |
| Pseudomonas aeruginosa | 3.7 | 3.0 | 5.0 | 2.9 |
| Staphylococcus saprophyticus | 3.0 | 1.9 | 5.4 | 1.4 |
| Others[b] | 10.2 | 13.3 | 11.8 | 16.0 |

[a]n = total number of isolates for the indicated month.
[b]See table 2.

TABLE 2

Distribution of uncommon[a] urinary isolates from positive urine samples ($\geq 10^7$ CFU/L) at the Centre Hospitalier de l'Université Laval (CHUL) for the 1992–1994 period.

| | % of isolates | | | |
|---|---|---|---|---|
| Organisms | Nov 92 | April 93 | July 93 | Jan 94 |
| Staphylococcus aureus | 0.4 | 1.1 | 1.3 | 1.4 |
| Staphylococcus spp. | 2.2 | 4.9 | 1.7 | 6.0 |
| Micrococcus spp. | 0.0 | 0.0 | 0.4 | 0.7 |
| Enterococcus faecium | 0.4 | 0.4 | 1.3 | 1.4 |
| Citrobacter spp. | 1.4 | 0.8 | 0.4 | 0.7 |
| Enterobacter spp. | 1.5 | 1.1 | 1.3 | 1.4 |
| Klebsiella oxytoca | 1.1 | 1.5 | 2.5 | 1.8 |
| Serratia spp. | 0.8 | 0.0 | 0.5 | 0.0 |
| Proteus spp. | 0.4 | 0.4 | 0.0 | 1.1 |
| Morganella and Providencia | 0.4 | 0.8 | 0.4 | 0.0 |
| Hafnia alvei | 0.8 | 0.0 | 0.0 | 0.0 |
| NFB[b] (Stenotrophomonas, Acinetobacter) | 0.0 | 0.4 | 1.32 | 1.1 |
| Candida spp. | 0.8 | 1.9 | 0.7 | 0.4 |

[a]Uncommon urinary isolates are those identified as "Others" in Table 1.
[b]NFB: non fermentative bacilli.

TABLE 3

Distribution of positive[a] (bacterial count $\geq 10^7$ CFU/L) and negative (bacterial count ($\geq 10^7$ CFU/L) urine specimens tested at the Centre Hospitalier de l'Université Laval (CHUL) for the 1992–1994 period.

| | Number of isolates (%) | | | |
|---|---|---|---|---|
| Specimens | Nov 92 | April 93 | July 93 | Jan 94 |
| received: | 1383(100) | 1338(100) | 1139(100) | 1345(100) |
| positive: | 267(19.3) | 265(19.8) | 238(20.9) | 281(20.9) |
| negative: | 1116(80.7) | 1073(80.2) | 901(79.1) | 1064(79.1) |

[a]Based on standard diagnostic methods, the minimal number of bacterial pathogens in urine samples to indicate an urinary tract infection is normally $10^7$ CFU/L.

TABLE 4

Distribution of positive and negative clinical specimens tested in the Microbiology Laboratory of the CHUL.

| Clinical specimens[a] | No. of samples tested | % of positive specimens | % of negative specimens |
|---|---|---|---|
| Urine | 17,981 | 19.4 | 8.6 |
| Haemoculture/marrow | 10.010 | 6.9 | 93.1 |
| Sputum | 1,266 | 68.4 | 31.6 |
| Superficial pus | 1,136 | 72.3 | 27.7 |
| Cerebrospinal fluid | 553 | 1.0 | 99.0 |
| Synovial fluid-articular | 523 | 2.7 | 97.3 |
| Bronch./Trac./Amyg./Throat | 502 | 56.6 | 43.4 |
| Deep pus | 473 | 56.8 | 43.2 |
| Ears | 289 | 47.1 | 52.9 |
| Pleural and pericardial fluid | 132 | 1.0 | 99.0 |
| Peritonial fluid | 101 | 28.6 | 71.4 |

[a]Specimens tested from February 1994 to January 1995.

TABLE 5

Bacterial species (66) used for testing the specificity of DNA fragment probes, oligonucleotide probes and PCR primers.

| Bacterial species | Number of strains tested | Bacterial species | Number of strains tested |
|---|---|---|---|
| Gram negative: | | Gram positive: | |
| *Proteus mirabilis* | 5 | *Streptococcus pneumoniae* | 7 |
| *Klebsiella pneumoniae* | 5 | *Streptococcus salivarius* | 2 |
| *Pseudomonas aeruginosa* | 5 | *Streptococcus viridans* | 2 |
| *Escherichia coli* | 5 | *Streptococcus pyogenes* | 2 |
| *Moraxella catarrhalis* | 5 | *Staphylococcus aureus* | 2 |
| *Proteus vulgaris* | 2 | *Staphylococcus epidermidis* | 2 |
| *Morganella morganii* | 2 | *Staphylococcus saprophyticus* | 5 |
| *Enterobacter cloacae* | 2 | Micrococcus species | 2 |
| *Providencia stuartii* | 1 | Corynebacterium species | 2 |
| *Providencia species* | 1 | Streptococcus groupe B | 2 |
| *Enterobacter agglomerans* | 2 | *Staphylococcus simulans* | 2 |
| *Providencia rettgeri* | 2 | *Staphylococcus ludgunensis* | 1 |
| *Neisseria mucosa* | 1 | *Staphylococcus capitis* | 2 |
| *Providencia alcalifaciens* | 1 | *Staphylococcus haemolyticus* | 2 |
| *Providencia rustigianii* | 1 | *Staphylococcus hominis* | 2 |
| *Burkholderia cepacia* | 2 | *Enterococcus faecalis* | 2 |
| *Enterobacter aerogenes* | 2 | *Enterococcus faecium* | 1 |
| *Stenotrophomonas maltophilia* | 2 | *Staphylococcus warneri* | 1 |
| *Pseudomonas fluorescens* | 1 | *Enterococcus durans* | 1 |
| *Comamonas acidovorans* | 2 | *Streptococcus bovis* | 1 |
| *Pseudomonas putida* | 2 | Diphteroids | 2 |
| *Haemophilus influenzae* | 5 | *Lactobacillus acidophilus* | 1 |
| *Haemophilus parainfluenzae* | 2 | | |
| *Bordetella pertussis* | 2 | | |
| *Haemophilus parahaemolyticus* | 2 | | |
| *Haemophilus haemolyticus* | 2 | | |
| *Haemophilus aegyptius* | 1 | | |
| *Kingella indologenes* | 1 | | |
| *Moraxella atlantae* | 1 | | |
| *Neisseria caviae* | 1 | | |
| *Neisseria subflava* | 1 | | |
| *Moraxella urethralis* | 1 | | |
| *Shigella sonnei* | 1 | | |
| *Shigella flexneri* | 1 | | |
| *Klebsiella oxytoca* | 2 | | |
| *Serratia marcescens* | 2 | | |
| *Salmonella typhimurium* | 1 | | |
| *Yersinia enterocolitica* | 1 | | |
| *Acinetobacter calcoaceticus* | 1 | | |
| *Acinetobacter lwoffi* | 1 | | |
| *Hafnia alvei* | 2 | | |
| *Citrobacter diversus* | 1 | | |
| *Citrobacter freundii* | 1 | | |
| Salmonella species | 1 | | |

TABLE 6

Species-specific DNA fragment and oligonucleotide probes for hybridization.

| Organisms[a] | Number of fragment probes[b] | | | Number of oligonucleotide probes | | |
|---|---|---|---|---|---|---|
| | Tested | Specific | Ubiquitous[c] | Synthesized | Specific | Ubiquitous[c] |
| E. coli[d] | — | — | — | 20 | 12 | 9[f] |
| E. coli | 14 | 2 | 2[e] | — | — | — |
| K. pneumoniae[d] | — | — | — | 15 | 1 | 1 |
| K. pneumoniae | 33 | 3 | 3 | 18 | 12 | 8 |
| P. mirabilis[d] | — | — | — | 3 | 3 | 2 |
| P. mirabilis | 14 | 3 | 3[e] | 15 | 8 | 7 |
| P. aeruginosa[d] | — | — | — | 26 | 13 | 9 |
| P. aeruginosa | 6 | 2 | 2[e] | 6 | 0 | 0 |
| S. saprophyticus | 7 | 4 | 4 | 20 | 9 | 7 |
| H. influenzae[d] | — | — | — | 16 | 2 | 2 |
| H. influenzae | 1 | 1 | 1 | 20 | 1 | 1 |
| S. pneumoniae[d] | — | — | — | 6 | 1 | 1 |
| S. pneumoniae | 19 | 2 | 2 | 4 | 1 | 1 |
| M. catarrhalis | 2 | 2 | 2 | 9 | 8 | 8 |
| S. epidermidis | 62 | 1 | 1 | — | — | |
| S. aureus | 30 | 1 | 1 | — | — | |
| Universal probes[d] | — | — | — | 7 | — | 7[g] |

[a]No DNA fragment or oligonucleotide probes were tested for E. faecalis and S. pyogenes.
[b]Sizes of DNA fragments range from 0.25 to 5.0 kbp.
[c]A specific probe was considered ubiquitous when at least 80% of isolates of the target species (approximately 80 isolates) were recognized by each specific probe. When 2 or more probes are combined, 100% of the isolates are recognized.
[d]These sequences were selected from data banks.
[e]Ubiquity tested with approximately 10 isolates of the target species.
[f]A majority of probes (8/9) do not discriminate E. coli and Shigella spp.
[g]Ubiquity tests with a pool of the 7 probes detected all 66 bacterial species listed in Table 5.

TABLE 7

PCR amplification for bacterial pathogens commonly encountered in urine, sputum, blood, cerebrospinal fluid and other specimens.

| Organism | Primer pair[a] # (SEQ ID NO) | Amplicon size (bp) | Ubiquity[b] | DNA amplification from colonies[c] | from specimens[d] |
|---|---|---|---|---|---|
| E. coli | 1[e] (55–56) | 107 | 75/80 | + | + |
| | 2[e] (46–47) | 297 | 77/80 | + | + |
| | 3 (42–43) | 102 | 78/80 | + | + |
| | 4 (131–132) | 134 | 73/80 | + | + |
| | 1 + 3 + 4 | — | 80/80 | + | + |
| E. faecalis | 1[e] (38–39) | 200 | 71/80 | + | + |
| | 2[e] (40–41) | 121 | 79/80 | + | + |
| | 1 + 2 | — | 80/80 | + | + |
| K. pneumoniae | 1 (67–68) | 198 | 76/80 | + | + |
| | 2 (61–62) | 143 | 67/80 | + | + |
| | 3[h] (135–136) | 148 | 78/80 | + | N. T.[i] |
| | 4 (137–138) | 116 | 69/80 | + | N. T. |
| | 1 + 2 + 3 | — | 80/80 | + | N. T. |
| P. mirabilis | 1 (74–75) | 167 | 73/80 | + | N. T. |
| | 2 (133–134) | 123 | 80/80 | + | N. T. |
| P. aeruginosa | 1[e] (83–84) | 139 | 79/80 | + | N. T. |
| | 2[e] (85–86) | 223 | 80/80 | + | N. T. |
| S. saprophyticus | 1 (98–99) | 126 | 79/80 | + | + |
| | 2 (139–140) | 190 | 80/80 | + | N. T. |
| M. catarrhalis | 1 (112–113) | 157 | 79/80 | + | N. T. |
| | 2 (118–119) | 118 | 80/80 | + | N. T. |
| | 3 (160–119) | 137 | 80/80 | + | N. T. |
| H. influenzae | 1[e] (154–155) | 217 | 80/80 | + | N. T. |
| S. pneumoniae | 1[e] (156–157) | 134 | 80/80 | + | N. T. |
| | 2[e] (158–159) | 197 | 74/80 | + | N. T. |
| | 3 (78–79) | 175 | 67/80 | + | N. T. |
| S. epidermidis | 1 (147–148) | 175 | 80/80 | + | N. T. |
| | 2 (145–146) | 125 | 80/80 | + | N. T. |
| S. aureus | 1 (152–153) | 108 | 80/80 | + | N. T. |
| | 2 (149–150) | 151 | 80/80 | + | N. T. |
| | 3 (149–151) | 176 | 80/80 | + | N. T. |
| S. pyogenes[f] | 1[e] (141–142) | 213 | 80/80 | + | N. T. |
| | 2[e] (143–144) | 157 | 24/24 | + | N. T. |

TABLE 7-continued

PCR amplification for bacterial pathogens commonly encountered in urine, sputum, blood, cerebrospinal fluid and other specimens.

| Organism | Primer pair[a] # (SEQ ID NO) | Amplicon size (bp) | Ubiquity[b] | DNA amplification from colonies[c] | from specimens[d] |
|---|---|---|---|---|---|
| Universal | 1[e] (126–127) | 241 | 194/195[g] | + | + |

[a]All primer pairs are specific in PCR assays since no amplification was observed with DNA from 66 different species of both Gram positive and Gram negative bacteria other than the species of interest (Table 5).
[b]The ubiquity was normally tested on 80 strains of the species of interest. All retained primer pairs amplified at least 90% of the isolates. When combinations of primers were used, an ubiquity of 100% was reached.
[c]For all primer pairs and multiplex combinations, PCR amplifications directly performed from a bacterial colony were 100% species-specific.
[d]PCR assays performed directly from urine specimens.
[e]Primer pairs derived from data bank sequences. Primer pairs with no "e" are derived from our species-specific fragments.
[f]For *S. pyogenes*, primer pair #1 is specific for Group A Streptococci (GAS). Primer pair #2 is specific for the GAS-producing exotoxin A gene (SpeA).
[g]Ubiquity tested on 195 isolates from 23 species representative of bacterial pathogens commonly encountered in clinical specimens.
[h]Optimizations are in progress to eliminate non-specific amplification observed with some bacterial species other than the target species.
[i]N. T.: not tested.

TABLE 8

Selected antibiotic resistance genes for diagnostic purposes.

| Genes | Antibiotics | Bacteria[a] | SEQ ID NO |
|---|---|---|---|
| (bla$_{tem}$) TEM-1 | β-lactams | Enterobacteriaceae, Pseudomonaaaceae, Haemophilus, Neisseria | 161 |
| (bla$_{rob}$) ROB-1 | β-lactams | Haemophilus, Pasteurella | 162 |
| (bla$_{shv}$) SHV-1 | β-lactams | Klebsiella and other Enterobacteriaceae | 163 |
| aadB, aaC1, aaC2, aacC3, aacA4 | Aminoglycosides | Enterobacteriaceae, Pseudomonadaceae | 164, 165, 166 167, 168 |
| mecA | β-lactams | Staphylococci | 169 |
| vanH, vanA, vanX | Vancomycin | Enterococci | 170 |
| satA | Macrolides | Enterococci | 173 |
| aacA-aphD | Aminoglycosides | Enterococci, Staphylococci | 174 |
| vat | Macrolides | Staphylococci | 175 |
| vga | Macrolides | Staphylococci | 176 |
| msrA | Erythromycin | Staphylococci | 177 |
| Int and Sul conserved sequences | β-lactams, trimethoprim, aminoglycosides, antiseptic, chloramphenicol | Enterobacteriaceae, Pseudomonaaaceae | 171, 172 |

[a]Bacteria having high incidence for the specified antibiotic resistance genes. The presence in other bacteria is not excluded.

ANNEX I

Specific and ubiquitous oligonucleotides probes for hybridization

| SEQ ID NO | Nucleotide sequence | Originating DNA fragment SEQ ID NO | Nucleotide position |
|---|---|---|---|
| Bacterial species: | *Escherichia coli* | | |
| 44 | 5'-CAC CCG CTT GCG TGG CAA GCT GCC C | 5[a] | 213–237 |
| 45 | 5'-CGT TTG TGG ATT CCA GTT CCA TCC G | 5[a] | 489–513 |
| 48 | 5'-TGA AGC ACT GGC CGA AAT GCT GCG T | 6[a] | 759–783 |
| 49 | 5'-GAT GTA CAG GAT TCG TTG AAG GCT T | 6[a] | 898–922 |

ANNEX I-continued

Specific and ubiquitous oligonucleotides probes for hybridization

| SEQ ID NO | Nucleotide sequence | Originating DNA fragment SEQ ID NO | Nucleotide position |
|---|---|---|---|
| 50 | 5'-TAG CGA AGG CGT AGC AGA AAC TAA C | 7[a] | 1264–1288 |
| 51 | 5'-GCA ACC CGA ACT CAA CGC CGG ATT T | 7[a] | 1227–1251 |
| 52 | 5'-ATA CAC AAG GGT CGC ATC TGC GGC C | 7[a] | 1313–1337 |
| 53 | 5'-TGC GTA TGC ATT GCA GAC CTT GTG GC | 7[a] | 111–136 |
| 54 | 5'-GCT TTC ACT GGA TAT CGC GCT TGG G | 7[a] | 373–397 |
| Bacterial species: | *Proteus mirabilis* | | |
| 70[b] | 5'-TGG TTC ACT GAC TTT GCG ATG TTT C | 12 | 23–47 |
| 71 | 5'-TCG AGG ATG GCA TGC ACT AGA AAA T | 12 | 53–77 |
| 72[b] | 5'-CGC TGA TTA GGT TTC GCT AAA ATC TTA TTA | 12 | 80–109 |
| 73 | 5'-TTG ATC CTC ATT TTA TTA ATC ACA TGA CCA | 12 | 174–203 |
| 76 | 5'-CCG CCT TTA GCA TTA ATT GGT GTT TAT AGT | 13 | 246–275 |
| 77 | 5'-CCT ATT GCA GAT ACC TTA AAT GTC TTG GGC | 13 | 291–320 |
| 80[b] | 5'-TTG AGT GAT GAT TTC ACT GAC TCC C | 14 | 18–42 |
| 81 | 5'-GTC AGA CAG TGA TGC TGA CGA CAC A | 15[a] | 1185–1209 |
| 82 | 5'-TGG TTG TCA TGC TGT TTG TGT GAA AAT | 15[a] | 1224–1250 |
| Bacterial species: | *Klebsiella pneumoniae* | | |
| 57 | 5'-GTG GTG TCG TTC AGC GCT TTC AC | 8 | 45–67 |
| 58 | 5'-GCG ATA TTC ACA CCC TAC GCA GCC A | 9 | 161–185 |
| 59[b] | 5'-GTC GAA AAT GCC GGA AGA GGT ATA CG | 9 | 203–228 |
| 60[b] | 5'-ACT GAG CTG CAG ACC GGT AAA ACT CA | 9 | 233–258 |
| 63[b] | 5'-CGT GAT GGA TAT TCT TAA CGA AGG GC | 10 | 250–275 |
| 64[b] | 5'-ACC AAA CTG TTG AGC CGC CTG GA | 10 | 201–223 |
| 65 | 5'-GTG ATC GCC CCT CAT CTG CTA CT | 10 | 77–99 |
| 66 | 5'-CGC CCT TCG TTA AGA ATA TCC ATC AC | 10 | 249–274 |
| 69 | 5'-CAG GAA GAT GCT GCA CCG GTT GTT G | 11[a] | 296–320 |
| Bacterial species: | *Pseudomonas aeruginosa* | | |
| 87 | 5'-AAT GCG GCT GTA CCT CGG CGC TGG T | 18[a] | 2985–3009 |
| 88 | 5'-GGC GGA GGG CCA GTT GCA CCT GCC A | 18[a] | 2929–2953 |
| 89 | 5'-AGC CCT GCT CCT CGG CAG CCT CTG C | 18[a] | 2821–2845 |
| 90 | 5'-TGG CTT TTG CAA CCG CGT TCA GGT T | 18[a] | 1079–1103 |
| 91 | 5'-GCG CCC GCG AGG GCA TGC TTC GAT G | 19[a] | 705–729 |
| 92 | 5'-ACC TGG GCG CCA ACT ACA AGT TCT A | 19[a] | 668–692 |
| 93 | 5'-GGC TAC GCT GCC GGG CTG CAG GCC G | 19[a] | 505–529 |
| 94 | 5'-CCG ATC TAC ACC ATC GAG ATG GGC G | 20[a] | 1211–1235 |
| 95 | 5'-GAG CGC GGC TAT GTG TTC GTC GGC T | 20[a] | 2111–2135 |

ANNEX I-continued

Specific and ubiquitous oligonucleotides probes for hybridization

| SEQ ID NO | Nucleotide sequence | Originating DNA fragment SEQ ID NO | Nucleotide position |
|---|---|---|---|
| Bacterial species: | *Streptococcus pneumoniae* | | |
| 120 | 5'-TCT GTG CTA GAG ACT GCC CCA TTT C | 30 | 423–447 |
| 121 | 5'-CGA TGT CTT GAT TGA GCA GGG TTA T | 31[a] | 1198–1222 |
| Bacterial species: | *Staphylococcus saprophyticus* | | |
| 96 | 5'-CGT TTT TAC CCT TAC CTT TTC GTA CTA CC | 21 | 45–73 |
| 97[b] | 5'-TCA GGC AGA GGT AGT ACG AAA GGT AA GGG | 21 | 53–82 |
| 100 | 5'-CAC CAA GTT TGA CAC GTG AAG ATT CAT | 22 | 89–115 |
| 101[b] | 5'-ATG AGT GAA GCG GAG TCA GAT TAT GTG CAG | 23 | 105–134 |
| 102 | 5'-CGC TCA TTA CGT ACA GTG ACA ATC G | 24 | 20–44 |
| 103 | 5'-CTG GTT AGC TTG ACT CTT AAC AAT CTT GTC | 24 | 61–90 |
| 104[b] | 5'-GAC GCG ATT GTC ACT GTA CGT AAT GAG CGA | 24 | 19–48 |
| Bacterial species: | *Moraxella catarrhalis* | | |
| 108 | 5'-GCC CCA AAA CAA TGA AAC ATA TGG T-3' | 28 | 81–105 |
| 109 | 5'-CTG CAG ATT TTG GAA TCA TAT CGC C-3' | 28 | 126–150 |
| 110 | 5'-TGG TTT GAC CAG TAT TTA ACG CCA T-3' | 28 | 165–189 |
| 111 | 5'-CAA CGG CAC CTG ATG TAC CTT GTA C-3' | 28 | 232–256 |
| 114 | 5'-TTA CAA CCT GCA CCA CAA GTC ATC A-3' | 29 | 97–121 |
| 115 | 5'-GTA CAA ACA AGC CGT CAG CGA CTT A-3' | 29 | 139–163 |
| 116 | 5'-CAA TCT GCG TGT GTG CGT TCA CT-3' | 29 | 178–200 |
| 117 | 5'-GCT ACT TTG TCA GCT TTA GCC ATT CA-3' | 29 | 287–312 |
| Bacterial species: | *Haemophilus influenzae* | | |
| 105[b] | 5'-GCG TCA GAA AAA GTA GGC GAA ATG AAA G | 25 | 138–165 |
| 106[b] | 5'-AGC GGC TCT ATC TTG TAA TGA CAC A | 26[a] | 770–794 |
| 107[b] | 5'-GAA ACG TGA ACT CCC CTC TAT ATA A | 27[a] | 5184–5208 |
| | Universal probes[c] | | |
| 122[b] | 5'-ATC CCA CCT TAG GCG GCT GGC TCC A | – | – |
| 123 | 5'-ACG TCA AGT CAT CAT GGC CCT TAC GAG TAG G | – | – |
| 124[b] | 5'-GTG TGA CGG GCG GTG TGT ACA AGG C | – | – |
| 125[b] | 5'-GAG TTG CAG ACT CCA ATC CGG ACT ACG A | – | – |
| 128[b] | 5'-CCC TAT ACA TCA CCT TGC GGT TTA GCA GAG AG | – | – |
| 129 | 5'-GGG GGG ACC ATC CTC CAA GGC TAA ATA C | – | – |
| 130[b] | 5'-CGT CCA CTT TCG TGT TTG CAG AGT GCT GTG TT | – | – |

[a] Sequences from data banks
[b] These sequences are from the opposite DNA strand of the sequences given in the Sequence listing
[c] Universal probes were derived from 16S or 23S ribosomal RNA gene sequences not included in the Sequence listing

ANNEX I

Specific and ubiquitous oligonucleotides probes for hybridization

| SEQ ID NO | Nucleotide sequence | Originating DNA fragment SEQ ID NO | Nucleotide position |
|---|---|---|---|
| Bacterial species: *Haemophilus influenzae* | | | |
| 105[b] | 5'-GCG TCA GAA AAA GTA GGC GAA ATG AAA G | 25 | 138–165 |
| 106[b] | 5'-AGC GGC TCT ATC TTG TAA TGA CAC A | 26[a] | 770–794 |
| 107[b] | 5'-GAA ACG TGA ACT CCC CTC TAT ATA A | 27[a] | 5184–5208 |
| Universal probes[c] | | | |
| 122[b] | 5'-ATC CCA CCT TAG GCG GCT GGC TCC A | — | — |
| 123 | 5'-ACG TCA AGT CAT CAT GGC CCT TAC GAG TAG G | — | — |
| 124[b] | 5'-GTG TGA CGG GCG GTG TGT ACA AGG C | — | — |
| 125[b] | 5'-GAG TTG CAG ACT CCA ATC CGG ACT ACG A | — | — |
| 128[b] | 5'-CCC TAT ACA TCA CCT TGC GGT TTA GCA GAG AG | — | — |
| 129 | 5'-GGG GGG ACC ATC CTC CAA GGC TAA ATA C | — | — |
| 130[b] | 5'-CGT CCA CTT TCG#TGT TTG CAG AGT GCT GTG TT | — | — |

[a]Sequences from data banks
[b]These sequences are from the opposite DNA strand of the sequences given in the Sequence listing
[c]Universal probes were derived from 16S or 23S ribosomal RNA gene sequences not included in the Sequence listing

ANNEX II

Specific and ubiquitous primers for DNA amplification

| SEQ ID NO | Nucleotide sequence | Originating DNA fragment SEQ ID NO | Nucleotide position |
|---|---|---|---|
| Bacterial species: *Escherichia coli* | | | |
| 42 | 5'-GCT TTC CAG CGT CAT ATT G | 4 | 177–195 |
| 43[b] | 5'-GAT CTC GAC AAA ATG GTG A | 4 | 260–278 |
| 46 | 5'-TCA CCC GCT TGC GTG GC | 5[a] | 212–228 |
| 47[b] | 5'-GGA ACT GGA ATC CAC AAA C | 5[a] | 490–508 |
| 55 | 5'-GCA ACC CGA ACT CAA CGC C | 7[a] | 1227–1245 |
| 56[b] | 5'-GCA GAT GCG ACC CTT GTG T | 7[a] | 1315–1333 |
| 131 | 5'-CAG GAG TAC GGT GAT TTT TA | 3 | 60–79 |
| 132[b] | 5'-ATT TCT GGT TTG GTC ATA CA | 3 | 174–193 |
| Bacterial species: *Enterococcus faecalis* | | | |
| 38 | 5'-GCA ATA CAG GGA AAA ATG TC | 1[a] | 69–88 |
| 39[b] | 5'-CTT CAT CAA ACA ATT AAC TC | 1[a] | 249–268 |
| 40 | 5'-GAA CAG AAG AAG CCA AAA AA | 2[a] | 569–588 |
| 41[b] | 5'-GCA ATC CCA AAT AAT ACG GT | 2[a] | 670–689 |
| Bacterial species: *Klebsiella pneumoniae* | | | |
| 61 | 5'-GAC AGT CAG TTC GTC AGC C | 9 | 37–55 |
| 62[b] | 5'-CGT AGG GTG TGA ATA TCG C | 9 | 161–179 |
| 67 | 5'-TCG CCC CTC ATC TGC TAC T | 10 | 81–99 |
| 68[b] | 5'-GAT CGT GAT GGA TAT TCT T | 10 | 260–278 |
| 135 | 5'-GCA GCG TGG TGT CGT TCA | 8 | 40–57 |

ANNEX II-continued

Specific and ubiquitous primers for DNA amplification

| SEQ ID NO | Nucleotide sequence | Originating DNA fragment SEQ ID NO | Nucleotide position |
|---|---|---|---|
| 136[b] | 5'-AGC TGG CAA CGG CTG GTC | 8 | 170—187 |
| 137 | 5'-ATT CAC ACC CTA CGC AGC CA | 9 | 166—185 |
| 138[b] | 5'-ATC CGG CAG CAT CTC TTT GT | 9 | 262—281 |
| Bacterial species: | *Proteus mirabilis* | | |
| 74 | 5'-GAA ACA TCG CAA AGT CAG T | 12 | 23—41 |
| 75[b] | 5'-ATA AAA TGA GGA TCA AGT TC | 12 | 170—189 |
| 133 | 5'-CGG GAG TCA GTG AAA TCA TC | 14 | 17—36 |
| 134[b] | 5'-CTA AAA TCG CCA CAC CTC TT | 14 | 120—139 |
| Bacterial species: | *Staphylococcus saprophyticus* | | |
| 98 | 5'-CGT TTT TAC CCT TAC CTT TTC GTA CT | 21 | 45—70 |
| 99[b] | 5'-ATC GAT CAT CAC ATT CCA TTT GTT TTT A | 21 | 143—170 |
| 139 | 5'-CTG GTT AGC TTG ACT CTT AAC AAT C | 24 | 61—85 |
| 140[b] | 5'-TCT TAA CGA TAG AAT GGA GCA ACT G | 24 | 226—250 |
| Bacterial species: | *Pseudomonas aeruginosa* | | |
| 83 | 5'-CGA GCG GGT GGT GTT CAT C | 16[a] | 554—572 |
| 84[b] | 5'-CAA GTC GTC GTC GGA GGG A | 16[a] | 674—692 |
| 85 | 5'-TCG CTG TTC ATC AAG ACC C | 17[a] | 1423—1441 |
| 86[b] | 5'-CCG AGA ACC AGA CTT CAT C | 17[a] | 1627—1645 |
| Bacterial species: | *Moraxella catarrhalis* | | |
| 112 | 5'-GGC ACC TGA TGT ACC TTG | 28 | 235—252 |
| 113[b] | 5'-AAC AGC TCA CAC GCA TT | 28 | 375—391 |
| 118 | 5'-TGT TTT GAG CTT TTT ATT TTT TGA | 29 | 41—64 |
| 119[b] | 5'-CGC TGA CGG CTT GTT TGT ACC A | 29 | 137—158 |
| 160 | 5'-GCT CAA ATC AGG GTC AGC | 29 | 22—39 |
| 119[b] | 5'-CGC TGA CGG CTT GTT TGT ACC A | 29 | 137—158 |
| Bacterial species: | *Staphylococcus epidermidis* | | |
| 145 | 5'-ATC AAA AAG TTG GCG AAC CTT TTC A | 36 | 21—45 |
| 146[b] | 5'-CAA AAG AGC GTG GAG AAA AGT ATC A | 36 | 121—145 |
| 147 | 5'-TCT CTT TTA ATT TCA TCT TCA ATT CCA TAG | 36 | 448—477 |
| 148[b] | 5'-AAA CAC AAT TAC AGT CTG GTT ATC CAT ATC | 36 | 593—622 |
| Bacterial species: | *Staphylococcus aureus* | | |
| 149[b] | 5'-CTT CAT TTT ACG GTG ACT TCT TAG AAG ATT | 37 | 409—438 |
| 150 | 5'-TCA ACT GTA GCT TCT TTA TCC ATA CGT TGA | 37 | 288—317 |
| 149[b] | 5'-CTT CAT TTT ACG GTG ACT TCT TAG AAG ATT | 37 | 409—438 |
| 151 | 5'-ATA TTT TAG CTT TTC AGT TTC TAT ATC AAC | 37 | 263—292 |

ANNEX II-continued

Specific and ubiquitous primers for DNA amplification

| SEQ ID NO | Nucleotide sequence | Originating DNA fragment SEQ ID NO | Nucleotide position |
|---|---|---|---|
| 152 | 5'-AAT CTT TGT CGG TAC ACG ATA TTC TTC ACG | 37 | 5—34 |
| 153[b] | 5'-CGT AAT GAG ATT TCA GTA GAT AAT ACA ACA | 37 | 83—112 |
| Bacterial species: | Haemophilus influenzae | | |
| 154 | 5'-TTT AAC GAT CCT TTT ACT CCT TTT G | 27[a] | 5074—5098 |
| 155[b] | 5'-ACT GCT GTT GTA AAG AGG TTA AAA T | 27[a] | 5266—5290 |
| Bacterial species: | Streptococcus pneumoniae | | |
| 78 | 5'-AGT AAA ATG AAA TAA GAA CAG GAC GAC AG | 34 | 164—189 |
| 79[b] | 5'-AAA ACA GGA TAG GAG AAC GGG AAA A | 34 | 314—338 |
| 156 | 5'-ATT TGG TGA CGG GTG ACT TT | 31[a] | 1401—1420 |
| 157[b] | 5'-GCT GAG GAT TTG TTC TTC TT | 31[a] | 1515—1534 |
| 158 | 5'-GAG CGG TTT CTA TGA TTG TA | 35[a] | 1342—1361 |
| 159[b] | 5'-ATC TTT CCT TTC TTG TTC TT | 35[a] | 1519—1538 |
| Bacterial species: | Streptococcus pyogenes | | |
| 141 | 5'-TGA AAA TTC TTG TAA CAG GC | 32[a] | 286—305 |
| 142[b] | 5'-GGC CAC CAG CTT GCC CAA TA | 32[a] | 479—498 |
| 143 | 5'-ATA TTT TCT TTA TGA GGG TG | 33[a] | 966—985 |
| 144[b] | 5'-ATC CTT AAA TAA AGT TGC CA | 33[a] | 1103—1122 |
| | Universal primers[c] | | |
| 126 | 5'-GGA GGA AGG TGG GGA TGA CG | — | — |
| 127[b] | 5'-ATG GTG TGA CGG GCG GTG TG | — | — |

[a]Sequences from data banks
[b]These sequences are from the opposite DNA strand of the sequences given in the Sequence listing
[c]Universal primers were derived from the 16S ribosomal RNA gene sequence not included in the Sequence listing

ANNEX III

Selection of universal probes by alignment of the sequences of bacterial 16S and 23S ribosomal RNA genes.

| | |
|---|---|
| Reverse strand of SEQ ID NO: 122 | TGGAGCC AGCCGCCTAA GGTGGGAT |
| | 1461                                              1510 |
| Streptococcus salivarius | TGAGGTAACC TTTTGGAGCC AGCCGCCTAA GGTGGGATAG ATGANNGGGG |
| Proteus vulgaris | TAGCTTAACC TTCGGGAGGG CGCTTACCAC TTTGTGATTC ATGACTGGGG |
| Pseudomonas aeruginosa | TAGTCTAACC GCAAGGGGGA CGGTTACCAC GGAGTGATTC ATGACTGGGG |
| Neisseria gonorrhoeae | TAGGGTAACC GCAAGGAGTC CGCTTACCAC GGTATGCTTC ATGACTGGGG |
| Streptococcus lactis | TTGCCTAACC GCAAGGAGGG CGCTTCCTAA GGTAAGACCG ATGACNGGGG |
| SEQ ID NO: 123 | ACGTCAAGTC   ATCATGGC CCTTACGAGT AGG |
| | 1251                                              1300 |
| Haemophilus influenzae | GGTNGGGATG ACGTCAAGTC ..ATCATGGC CCTTACGAGT AGGGCTACAC |

ANNEX III-continued
Selection of universal probes by alignment of the sequences of bacterial 16S and 23S ribosomal RNA genes.

```
Neisseria gonorrhoeae          GGTGGGGATG  ACGTCAAGTC  ..CTCATGGC  CCTTATGACC  AGGGCTTCAC
Pseudomonas cepacia            GGTNGGGATG  ACGTCAAGTC  ..CTCATGGC  CCTTATGGGT  AGGGCTTCAC
Serratia marcescens            GGTGGGGATG  ACGTCAAGTC  ..ATCATGGC  CCTTACGAGT  AGGGCTACAC
Escherichia coli               GGTGGGGATG  ACGTCAAGTC  ..ATCATGGC  CCTTACGACC  AGGGCTACAC
Proteus vulgaris               GGTGGGGATG  ACGTTAAGTC  GTATCATGGC  CCTTACGAGT  AGGGCTACAC
Pseudomonas aeruginosa         GGTGGGGATG  ACGTCAAGTC  ..ATCATGGC  CCTTACGGCN  AGGGCTACAC
Clostridium perfringens        GGTGGGGATG  ACGTNNAATC  ..ATCATGCC  CNTTATGTGT  AGGGCTACAC
Mycoplasma hominis             GGTGGGGATG  ACGTCAAATC  ..ATCATGCC  TCTTACGAGT  GGGGCCACAC
Helicobacter pylori            GGTGGGGACG  ACGTCAAGTC  ..ATCATGGC  CCTTACGCCT  AGGGCTACAC
Mycoplasma pneumoniae          GGAAGGGATG  ACGTCAAATC  ..ATCATGCC  CCTTATGTCT  AGGGCTGCAA
Reverse of the probe SEQ ID NO: 124      GCCTTGTACA  CACCGCCCGT  CACAC 1451                                 1490
Escherichia coli               ACGTTCCCGG  GCCTTGTACA  CACCGCCCGT  CACACCATGG
Neisseria gonorrhoeae          ACGTTCCCNG  NNCTTGTACA  CACCGCCCGT  CACACCATGG
Pseudomonas cepacia            ACGTTCCCGG  GTCTTGTACA  CACNGCCCGT  CACACCATGG
Serratia marcescens            ACGTTCCCGG  GCCTTGTACA  CACCGCCCGT  CACACCATGG
Proteus vulgaris               ACGTTCCCGG  GCCTTGTACA  CACCGCCCGT  CACACCATGG
Haemophilus influenzae         ACGTTCCCGG  GCNTTGTACA  CACCGCCCGT  CACACCATGG
Pseudomonas aeruginosa         ACGTTCCCGG  GCCTTGTACA  CACCGCCCGT  CACACCATGG
Clostridium perfringens        ACGTTCCCNG  GTCTTGTACA  CACCGCNCGT  CACACCATGA
Mycoplasma hominis             ACGTTCTCGG  GTCTTGTACA  CACCGCCCGT  CACACCATGG
Helicobacter pylori            ACGTTCCCGG  GTCTTGTACT  CACCGCCCGT  CACACCATGG
Mycoplasma pneumoniae          ACGTTCTCGG  GTCTTGTACA  CACCGCCCGT  CAAACTATGA
Reverse strand of SEQ ID NO 125:    TCG  TAGTCCGGAT  TGGAGTCTGC  AACTC 1361                                 1400
Escherichia coli               AAGTGCGTCG  TAGTCCGGAT  TGGAGTCTGC  AACTCGACTC
Neisseria gonorrhoeae          AAACCGATCG  TAGTCCGGAT  TGCACTCTGC  AACTCGAGTG
Pseudomonas cepacia            AAACCGATCG  TAGTCCGGAT  TGCACTCTGC  AACTCGAGTG
Serratia marcescens            AAGTATGTCG  TAGTCCGGAT  TGGAGTCTGC  AACTCGACTC
Proteus vulgaris               AAGTCTGTCG  TAGTCCGGAT  TGGAGTCTGC  AACTCGACTC
Haemophilus influenzae         AAGTACGTCT  AAGTCCGGAT  TGGAGTCTGC  AACTCGACTC
Pseudomonas aeruginosa         AAACCGATCG  TAGTCCGGAT  CGCAGTCTGC  AACTCGACTG
Clostridium perfringens        AAACCAGTCT  CAGTTCGGAT  TGTAGGCTGA  AACTCGCCTA
Mycoplasma hominis             AAGCCGATCT  CAGTTCGGAT  TGGAGTCTGC  AATTCGACTC
Helicobacter pylori            ACACC..TCT  CAGTTCGGAT  TGTAGGCTGC  AACTCGCCTG
Mycoplasma pneumoniae          AAGTTGGTCT  CAGTTCGGAT  TGAGGGCTGC  AATTCGTCCT
Reverse strand of SEQ ID NO: 128    CT  CTCTGCTAAA  CCGCAAGGTG  ATGTATAGGG
```

ANNEX III-continued

Selection of universal probes by alignment of the
sequences of bacterial 16S and 23S ribosomal RNA genes.

| | |
|---|---|
| *Lactobacillus lactis* | AAACACAGCT CTCTGCTAAA CCGCAAGGTG ATGTATAGGG GGTGACGCCT |
| *Escherichia coli* | AAACACAGCA CTGTGCAAAC ACGAAAGTGG ACGTATACGG TGTGACGCCT |
| *Pseudomonas aeruginosa* | AAACACAGCA CTCTGCAAAC ACGAAAGTGG ACGTATAGGG TGTGACGCCT |
| *Pseudomonas cepacia* | AAACACAGCA CTCTGCAAAC ACGAAAGTGG ACGTATAGGG TGTGACGCCT |
| *Bacillus stearothermophilus* | AAACACAGGT CTCTGCGAAG TCGTAAGGCG ACGTATAGGG GCTGACACCT |
| *Micrococcus luteus* | AAACACAGGT CCATGCGAAG TCGTAAGACG ATGTATATGG ACTGACTCCT |
| SEQ ID NO: 129 | GGGGGGACC ATCCTCCAAG GCTAAATAC |
| | 481                                                          530 |
| *Escherichia coli* | TGTCTGAATA TGGGGGGACC ATCCTCCAAG GCTAAATACT CCTGACTGAC |
| *Pseudomonas aeruginosa* | TGTCTGAACA TGGGGGGACC ATCCTCCAAG GCTAAATACT ACTGACTGAC |
| *Pseudomonas cepacia* | TGTCTGAAGA TGGGGGGACC ATCCTCCAAG GCTAAATACT CGTGATCGAC |
| *Lactobacillus lactis* | AGTTTGAATC CGGGAGGACC ATCTCCCAAC CCTAAATACT CCTTAGTGAC |
| *Micrococcus luteus* | CGTGTGAATC TGCCAGGACC ACCTGGTAAG CCTGAATACT ACCTGTTGAC |
| Reverse strand of SEQ ID NO: 130 | AACACAGCA CTCTGCAAAC ACGAAAGTGG ACG |
| | 1981                                                         2030 |
| *Pseudomonas aeruginosa* | TGTTTATTAA AAACACAGCA CTCTGCAAAC ACGAAAGTGG ACGTATAGGG |
| *Escherichia coli* | TGTTTATTAA AAACACAGCA CTGTGCAAAC ACGAAAGTGG ACGTATACGG |
| *Pseudomonas cepacia* | TGTTTAATAA AAACACAGCA CTCTGCAAAC ACGAAAGTGG ACGTATAGGG |
| *Bacillus stearothermophilus* | TGTTTATCAA AAACACAGGT CTCTGCGAAG TCGTAAGGCG ACGTATAGGG |
| *Lactobacillus lactis* | TGTTTATCAA AAACACAGCT CTCTGCTAAA CCGCAAGGTG ATGTATAGGG |
| *Micrococcus luteus* | TGTTTATCAA AAACACAGGT CCATGCGAAG TCGTAAGACG ATGTATATGG |

ANNEX IV

Selection of the universal PCR primers by alignment of the bacterial
16S ribosomal RNA gene

| | |
|---|---|
| SEQ ID NO: 126 | GGAGGAA GGTGGGGATG ACG |
| Reverse strand of SEQ ID NO: 127 | CA CACCGCCCGT CACACCAT |
| | 1241                            1270......1461                       1490 |
| *Escherichia coli* | ACTGGAGGAA GGTGGGGATG ACGTCAAGTC......GCCTTGTACA CACCGCCCGT CACACCATGG |
| *Neisseria gonorrhoeae* | GCCGGAGGAA GGTGGGGATG ACGTCAAGTC......NNCTTGTACA CACCGCCCGT CACACCATGG |
| *Pseudomonas cepacia* | ACCGGAGGAA GGTNGGGATG ACGTCAAGTC......GTCTTGTACA CACNGCCCGT CACACCATGG |
| *Serratia marcescens* | ACTGGAGGAA GGTGGGGATG ACGTCAAGTC......GCCTTGTACA CACCGCCCGT CACACCATGG |
| *Proteus vulgaris* | ACCGGAGGAA GGTGGGGATG ACGTTAAGTC......GCCTTGTACA CACCGCCCGT CACACCATGG |
| *Haemophilus influenzae* | ACTGGAGGAA GGTNGGGATG ACGTCAAGTC......GCNTTGTACA CACCGCCCGT CACACCATGG |
| *Legionella pneumophila* | ACCGGAGGAA GGCGGGGATG ACGTCAAGTC......GCCTTGTACA CACCGCCCGT CACACCATGG |
| *Pseudomonas aeruginosa* | ACCGGAGGAA GGTGGGGATG ACGTCAAGTC......GCCTTGTACA CACCGCCCGT CACACCATGG |
| *Clostridium perfringens* | CCAGGAGGAA GGTGGGGATG ACGTNNAATC......GTCTTGTACA CACCGCNCGT CACACCATGA |
| *Mycoplasma hominis* | CTGGGAGGAA GGTGGGGATG ACGTCAAATC......GTCTTGTACA CACCGCCCGT CACACCATGG |

ANNEX IV-continued

Selection of the universal PCR primers by alignment of the bacterial
16S ribosomal RNA gene

| | |
|---|---|
| *Helicobacter pylori* | GGAGGAGGAA GGTGGGGACG ACGTCAAGTC......GTCTTGTACT CACCGCCCGT CACACCATGG |
| *Mycoplasma pneumoniae* | ATTGGAGGAA GGAAGGGATG ACGTCAAATC......GTCTTGTACA CACCGCCCGT CAAACTATGA |

What is claimed is:

1. A method using probes or amplification primers or both which are specific, ubiquitous and sensitive for determining the presence or amount of nucleic acids:
   from a bacterial antibiotic resistance gene selected from the group consisting of $bla_{tem}$, $bla_{rob}$, $bla_{shv}$, aadB, aacC1, aacC2, aacC3, aacA4, mecA, vanA, vanH, vanX, satA, aacA-aphH, vat, vga, msrA sul, and int, and
   from specific bacterial species selected from the group consisting of *Escherichia coli, Klebsiella pneumoniae, Pseudomonas aeruginosa, Proteus mirabilis, Streptococcus pneumoniae, Staphylococcus aureus, Staplylococcus epidermidis, Enterococcus faecalis, Staphylococcus epidermidis, Enterococcus faecalis, Staphylococcus saprophyticus, Streptococcus pyogenes, Haemophilus influenzae,* and *Moraxella catarrhalis,* in any sample suspected of containing said nucleic acids,
   wherein each of said nucleic acids comprises a selected target region hybridizable with said probes or primers;
   said method comprising the steps of contacting said sample with said probes or primers and detecting the presence or amount of hybridized probes or amplified products as an indication of the presence or amount of said specific bacterial species simultaneously with said bacterial antibiotic resistance gene;
   said probes or primers comprising at least one single stranded nucleic acid which nucleotidic sequence has at least twelve nucleotides in length capable of hybridizing with said bacterial species and with any one of:
   SEQ ID NO. 3, SEQ ID NO. 4, SEQ ID NO. 5, SEQ ID NO. 6, SEQ ID NO. 7 and a complementary sequence thereof, for determining the presence or amount of *Escherichia coli;*
   SEQ ID NO. 8, SEQ ID NO. 9, SEQ ID NO. 10, SEQ ID NO. 11, and a complementary sequence thereof, for determining the presence or amount of *Klebsiella pneumoniae;*
   SEQ ID NO. 16, SEQ ID NO. 17, SEQ ID NO. 18, SEQ ID NO. 19, SEQ ID NO. 20 and a complementary sequence thereof, for determining the presence or amount of *Pseudomonas aeruginosa;*
   SEQ ID NO. 12, SEQ ID NO. 13, SEQ ID NO. 14, SEQ ID NO. 15 and a complementary sequence thereof, for determining the presence or amount of *Proteus mirabilis;*
   SEQ ID NO. 30, SEQ ID NO. 31, SEQ ID NO. 34, SEQ ID NO. 35 and complementary sequence thereof, for determining the presence or amount of *Streptococcus pneumoniae;*
   SEQ ID NO. 37 and a complementary sequence thereof, for determining the presence or amount of *Staplylococcus aureus;*
   SEQ ID NO. 36 and a complementary sequence thereof, for determining the presence or amount of *Staphylococcus epidermidis;*
   SEQ ID NO. 1, SEQ ID NO. 2 and a complementary sequence thereof, for determining the presence or amount of *Enterococcus faecalis;*
   SEQ ID NO. 21, SEQ ID NO. 22, SEQ ID NO. 23, SEQ ID NO. 24, and a complementary sequence thereof, for determining the presence or amount of *Staphylococcus saprophyticus;*
   SEQ ID NO. 32, SEQ ID NO. 33 and a complementary sequence thereof, for determining the presence or amount of *Streptococcus pyogenes;*
   SEQ ID NO. 25, SEQ ID NO. 26, SEQ ID NO. 27 and a complementary sequence thereof, for determining the presence or amount of *Haemophilus influenzae;* and
   SEQ ID NO. 28, SEQ ID NO. 29 and a complementary sequence thereof, for determining the presence or amount of *Moraxella catarrhalis.*

2. The method of any one of claim 1, which is performed directly on a sample obtained from human patients, animals, environment or food.

3. The method of claim 1, which is performed directly on a sample consisting of one or more bacterial colonies.

4. The method of claim 1, wherein said nucleic acids are amplified by a method selected from the group consisting of:
   a) polymerase chain reaction (PCR),
   b) ligase chain reaction,
   c) nucleic acid sequence-based amplification,
   d) self-sustained sequence replication,
   e) strand displacement amplification
   f) branched DNA signal amplification,
   g) nested PCR, and
   h) multiplex PCR.

5. The method of claim 4 wherein said nucleic acids are amplified by PCR.

6. The method of claim 5 wherein said nucleic acids are all simultaneously detected.

7. The method of claim 6 wherein the PCR protocol achieves within one hour the determination of the presence of said nucleic acids by performing for each amplification cycle an annealing step of only one second at 55° C. and a denaturation step of only one second at 95° C. without any time specifically allowed to an elongation step.

8. A method for the detection, identification or quantification of *Escherichia coli* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Escherichia coli* and capable of hybridizing with any one of SEQ ID NO. 3, SEQ ID NO. 4, SEQ ID NO. 5, SEQ ID NO. 6, SEQ ID NO. 7 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of *Escherichia coli* in said test sample.

9. A method for detecting the presence or amount of *Escherichia coli* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Escherichia coli* DNA and of any one of SEQ ID NO. 3, SEQ ID NO. 4, SEQ ID NO. 5, SEQ ID NO. 6, SEQ ID NO. 7, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of *Escherichia coli* in said test sample.

10. The method of claim 9, wherein said at least one pair of primers is selected from the group consisting of:

a) SEQ ID NO: 42 and SEQ ID NO: 43,
b) SEQ ID NO: 46 and SEQ ID NO: 47,
c) SEQ ID NO: 55 and SEQ ID NO: 56, and
d) SEQ ID NO: 131 and SEQ ID NO: 132.

11. A method for the detection, identification or quantification of *Moraxella catarrhalis* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Moraxella catarrhalis* and capable of hybridizing with any one of SEQ ID NO. 29 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of *Moraxella catarrhalis* in said test sample.

12. A method for detecting the presence or amount of *Moraxella catarrhalis* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Moraxella catarrhalis* DNA and of SEQ ID NO. 29, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of *Moraxella catarrhalis* in said test sample.

13. The method of claim 12, wherein said at least one pair of primers is selected from the group consisting of:

a) SEQ ID NO: 118 and SEQ ID NO: 119, and
b) SEQ ID NO: 160 and SEQ ID NO: 119.

14. A method for the detection, identification or quantification of *Pseudomonas aeruginosa* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Pseudomonas aeruginosa* and capable of hybridizing with any one of SEQ ID NO. 16, SEQ ID NO. 17, SEQ ID NO. 18, SEQ ID NO. 19, SEQ ID NO. 20 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of *Pseudomonas aeruginosa* in said test sample.

15. A method for detecting the presence or amount of *Pseudomonas aeruginosa* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Pseudomonas aeruginosa* DNA and of any one of SEQ ID NO. 16, SEQ ID NO. 17, SEQ ID NO. 18, SEQ ID NO. 19, SEQ ID NO. 20, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of *Pseudomonas aeruginosa* in said test sample.

16. The method of claim 15, wherein said at least one pair of primers is selected from the group consisting of:

a) SEQ ID NO: 83 and SEQ ID NO: 84, and b) SEQ ID NO: 85 and SEQ ID NO: 86.

17. A method for the detection, identification or quantification of *Staphylococcus epidermidis* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Staphylococcus epidermidis* and capable of hybridizing with any one of SEQ ID NO. 36 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of *Staphylococcus epidermidis* in said test sample.

18. A method for detecting the presence or amount of *Staphylococcus epidermidis* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Staphylococcus epidermidis* DNA and of SEQ ID NO. 36, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of *Staphylococcus epidermidis* in said test sample.

19. The method of claim 18, wherein said at least one pair of primers is selected from the group consisting of:

a) SEQ ID NO: 145 and SEQ ID NO: 146, and b) SEQ ID NO: 147 and SEQ ID NO: 148.

20. A method for the detection, identification or quantification of *Staphylococcus aureus* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Staphylococcus aureus* and capable of hybridizing with any one of SEQ ID NO. 37 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of *Staphylococcus aureus* in said test sample.

21. A method for detecting the presence or amount of *Staphylococcus aureus* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Staphylococcus aureus* DNA and of SEQ ID NO. 37, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of *Staphylococcus aureus* in said test sample.

22. The method of claim 21, wherein said at least one pair of primers is selected from the group consisting of:
 a) SEQ ID NO: 149 and SEQ ID NO: 150,
 b) SEQ ID NO: 149 and SEQ ID NO: 151, and
 c) SEQ ID NO: 152 and SEQ ID NO: 153.

23. A method for the detection, identification or quantification of *Streptococcus pneumoniae* directly from a test sample or from bacterial colonies, which comprises the following steps:
 a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
 b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Streptococcus pneumoniae* and capable of hybridizing with any one of SEQ ID NO. 30, SEQ ID NO. 31, SEQ ID NO. 34, SEQ ID NO. 35 and a sequence complementary thereof, under conditions such that the nucleic acid of said probe can selectively hybridize with said bacterial DNA, whereby a hybridization complex is formed, and
 c) detecting the presence of said hybridization complex on said inert support or in said solution as an indication of the presence or amount of *Streptococcus pneumoniae* in said test sample.

24. A method for detecting the presence or amount of *Streptococcus pneumoniae* in a test sample which comprises the following steps:
 a) treating said sample with an aqueous solution containing at least one pair of oligonucleotide primers having at least twelve nucleotides in length, one of said primers being capable of hybridizing selectively with one of the two complementary strands of *Streptococcus pneumoniae* DNA and of any one of SEQ ID NO. 30, SEQ ID NO. 31, SEQ ID NO. 34, SEQ ID NO. 35, that contain a target sequence, and the other of said primers being capable of hybridizing with the other of said strands so as to form an extension product which contains the target sequence as a template;
 b) synthesizing an extension product of each of said primers which extension product contains the target sequence, and amplifying said target sequence, if any, to a detectable level; and
 c) detecting the presence or amount of said amplified target sequence as an indication of the presence or amount of *Streptococcus pneumoniae* in said test sample.

25. The method of claim 24, wherein said at least one pair of primers is selected from the group consisting of;
 a) SEQ ID NO: 78 and SEQ ID NO: 79,
 b) SEQ ID NO: 156 and SEQ ID NO: 157, and
 c) SEQ ID NO: 158 and SEQ ID NO: 159.

26. A method for the detection, identification or quantification of a bacterial species bearing exotoxin A gene speA directly from a test sample or from bacterial colonies, which comprises the following steps:
 a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
 b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of a bacterial species bearing exotoxin A gene speA and capable of hybridizing with any one of SEQ ID NO. 33 and a sequence complementary thereof, under conditions such that the nucleic acid of said probe can selectively hybridize with said bacterial DNA, whereby a hybridization complex is formed, and
 c) detecting the presence of said hybridization complex on said inert support or in said solution as an indication of the presence or amount of a bacterial species bearing exotoxin A gene speA in said test sample.

27. A method for detecting the presence or amount of a bacterial species bearing exotoxin A gene speA in a test sample which comprises the following steps:
 a) treating said sample with an aqueous solution containing at least one pair of oligonucleotide primers having at least twelve nucleotides in length, one of said primers being capable of hybridizing selectively with one of the two complementary strands of a bacterial species bearing exotoxin A gene speA DNA and of SEQ ID NO. 33, that contain a target sequence, and the other of said primers being capable of hybridizing with the other of said strands so as to form an extension product which contains the target sequence as a template;
 b) synthesizing an extension product of each of said primers which extension product contains the target sequence, and amplifying said target sequence, if any, to a detectable level; and
 c) detecting the presence or amount of said amplified target sequence as an indication of the presence or amount of a bacterial species bearing exotoxin A gene speA in said test sample.

28. The method of claim 27, wherein said at least one pair of primers is SEQ ID NO: 143 and SEQ ID NO: 144.

29. A method for the detection, identification or quantification of *Enterococcus faecalis* directly from a test sample or from bacterial colonies, which comprises the following steps:
 a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
 b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Enterococcus faecalis* and capable of hybridizing with any one of SEQ ID NO. 1, and SEQ ID NO. 2 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of *Enterococcus faecalis* in said test sample.

30. A method for detecting the presence or amount of *Enterococcus faecalis* in a test sample which comprises the following steps:
   a) treating said sample with an aqueous solution containing at least one pair of oligonucleotide primers having at least twelve nucleotides in length, one of said primers being capable of hybridizing selectively with one of the two complementary strands of *Enterococcus faecalis* DNA and of any one of SEQ ID NO. 1 and SEQ ID NO. 2, that contain a target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of *Enterococcus faecalis* in said test sample.

31. The method of claim 30, wherein said at least one pair of primers is selected from the group consisting of:
   a) SEQ ID NO: 38 and SEQ ID NO: 39, and
   b) SEQ ID NO: 40 and SEQ ID NO: 41.

32. A method for detecting the presence or amount of any bacterial species in a test sample which comprises the following steps:
   a) treating said sample with an aqueous solution containing a pair of universal primers which sequence is defined in SEQ ID NO: 126 and SEQ ID NO: 127, one of said primers being capable of hybridizing selectively with one of the two complementary strands of said any bacterial species DNA that contain a target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of said any bacterial species in said test sample.

33. A method as defined in claim 1, which comprises the evaluation of the presence of a bacterial resistance to β-lactam antibiotics mediated by the bacterial antibiotic resistance gene bla$_{tem}$ directly from a test sample or from bacterial colonies, which comprises the steps of:
   a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 161 or a sequence complementary thereof under conditions such that the nucleic acid of said probe or primers can selectively hybridize with said gene; and
   b) detecting the presence of a hybridization complex or of an amplification product as an indication of a bacterial resistance to β-lactam antibiotics mediated by the bacterial antibiotic resistance gene bla$_{tem}$.

34. A method as defined in claim 1, which comprises the evaluation of the presence of a bacterial resistance to β-lactam antibiotics mediated by the bacterial antibiotic resistance gene bla$_{rob}$ directly from a test sample or from bacterial colonies, which comprises the steps of:
   a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 162 or a sequence complementary thereof under conditions such that the nucleic acid of said probe or primers can selectively hybridize with said gene; and
   b) detecting the presence of a hybridization complex or of an amplification product as an indication of a bacterial resistance to β-lactam antibiotics mediated by the bacterial antibiotic resistance gene bla$_{rob}$.

35. A method as defined in claim 1, which comprises the evaluation of the presence of a bacterial resistance to β-lactam antibiotics mediated by the bacterial antibiotic resistance gene bla$_{shv}$ directly from a test sample or from bacterial colonies, which comprises the steps of:
   a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 163 or a sequence complementary thereof under conditions such that the nucleic acid of said probe or primers can selectively hybridize with said gene; and
   b) detecting the presence of a hybridization complex or of an amplification product as an indication of a bacterial resistance to β-lactam antibiotics mediated by the bacterial antibiotic resistance gene bla$_{shv}$.

36. A method as defined in claim 1, which comprises the evaluation of the presence of a bacterial resistance to aminoglycoside mediated by the bacterial antibiotic resistance gene aadB directly from a test sample or from bacterial colonies, which comprises the steps of:
   a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 164 or a sequence complementary thereof under conditions such that the nucleic acid of said probe or primers can selectively hybridize with said gene; and
   b) detecting the presence of a hybridization complex or of an amplification product as an indication of a bacterial resistance to aminoglycoside antibiotics mediated by the bacterial antibiotic resistance gene aadB.

37. A method as defined in claim 1, which comprises the evaluation of the presence of a bacterial resistance to aminoglycoside antibiotics mediated by the bacterial antibiotic resistance gene aacC1 directly from a test sample or from bacterial colonies, which comprises the steps of:
   a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 165 or a sequence complementary thereof under conditions such that the nucleic acid of said probe or primers can selectively hybridize with said gene; and b) detecting the presence of a hybridization complex or of an amplification product as an indication of a bacterial resistance to aminoglycoside antibiotics mediated by the bacterial antibiotic resistance gene aacC1.

38. A method as defined in claim 1, which comprises the evaluation of the presence of a bacterial resistance to aminoglycoside antibiotics mediated by the bacterial antibiotic resistance gene aacC2 directly from a test sample or from bacterial colonies, which comprises the steps of:

a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 166 or a sequence complementary thereof under conditions such that the nucleic acid of said probe or primers can selectively hybridize with said gene; and b) detecting the presence of a hybridization complex or of an amplification product as an indication of a bacterial resistance to aminoglycoside antibiotics mediated by the bacterial antibiotic resistance gene aacC2.

39. A method as defined in claim 1, which comprises the evaluation of the presence of a bacterial resistance to aminoglycoside antibiotics mediated by the bacterial antibiotic resistance gene aacC3 directly from a test sample or from bacterial colonies, which comprises the steps of:

a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 167 or a sequence complementary thereof under conditions such that the nucleic acid of said probe or primers can selectively hybridize with said gene; and b) detecting the presence of a hybridization complex or of an amplification product as an indication of a bacterial resistance to aminoglycoside antibiotics mediated by the bacterial antibiotic resistance gene aacC3.

40. A method as defined in claim 1, which comprises the evaluation of the presence of a bacterial resistance to aminoglycoside antibiotics mediated by the bacterial antibiotic resistance gene aacA4 directly from a test sample or from bacterial colonies, which comprises the steps of:

a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 168 or a sequence complementary thereof under conditions such that the nucleic acid of said probe or primers can selectively hybridize with said gene; and b) detecting the presence of a hybridization complex or of an amplification product as an indication of a bacterial resistance to aminoglycoside antibiotics mediated by the bacterial antibiotic resistance gene aacA4.

41. A method as defined in claim 1, which comprises the evaluation of the presence of a bacterial resistance to β-lactam antibiotics mediated by the bacterial antibiotic resistance gene mecA directly from a test sample or from bacterial colonies, which comprises the steps of:

a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 169 or a sequence complementary thereof under conditions such that the nucleic acid of said probe or primers can selectively hybridize with said gene; and b) detecting the presence of a hybridization complex or of an amplification product as an indication of a bacterial resistance to β-lactam antibiotics mediated by the bacterial antibiotic resistance gene mecA.

42. A method as defined in claim 1, which comprises the evaluation of the presence of a bacterial resistance to vancomycin mediated by the bacterial antibiotic resistance genes vanH, vanA and vanX directly from a test sample or from bacterial colonies, which comprises the steps of:

a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 170 or a sequence complementary thereof under conditions such that the nucleic acid of said probe or primers can selectively hybridize with said gene; and b) detecting the presence of a hybridization complex or of an amplification product as an indication of a bacterial resistance to vancomycin mediated by the bacterial antibiotic resistance genes vanH, vanA and vanX.

43. A method as defined in claim 1, which comprises the evaluation of the presence of a bacterial resistance to streptogramin A mediated by the bacterial antibiotic resistance gene satA directly from a test sample or from bacterial colonies, which comprises the steps of:

a) contacting the bacterial DNA with a probe or with amplification primers, said probe or primers comprising at least one single stranded nucleic acid which nucleotidic sequence ha at least twelve nucleotides in length capable of hybridizing with the nucleotide sequence defined in SEQ ID NO. 173 or a sequence complementary thereof under conditions such that the nucleic acid of said probe or primers can selectively hybridize with said gene; and b) detecting the presence of a hybridization complex or of an amplification product as an indication of a bacterial resistance to streptogramin A mediated by the bacterial antibiotic resistance gene satA.

44. A method as defined in claim 1, which comprises the evaluation of the presence of a bacterial resistance to aminoglycoside antibiotics mediated by the bacterial antibiotic resistance gene aacA-aphD directly from a test sample or from bacterial colonies, which comprises the steps of:

a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 174 or a sequence complementary thereof under conditions such that the nucleic acid of said probe or primers can selectively hybridize with said gene; and b) detecting the presence of a hybridization complex or of an amplification product as an indication of a bacterial resistance to aminoglycoside antibiotics mediated by the bacterial antibiotic resistance gene aacA-aphD.

45. A method as defined in claim 1, which comprises the evaluation of the presence of a bacterial resistance to virginiamycin mediated by the bacterial antibiotic resistance gene vat directly from a test sample or from bacterial colonies, which comprises the steps of:
  a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 175 or a sequence complementary thereof under conditions such that the nucleic acid of said probe or primers can selectively hybridize with said gene; and
  b) detecting the presence of a hybridization complex or of an amplification product as an indication of a bacterial resistance to virginiamycin mediated by the bacterial antibiotic resistance gene vat.

46. A method as defined in claim 1, which comprises the evaluation of the presence of a bacterial resistance to virginiamycin mediated by the bacterial antibiotic resistance gene vga directly from a test sample or from bacterial colonies, which comprises the steps of:
  a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 176 or a sequence complementary thereof under conditions such that the nucleic acid of said probe or primers can selectively hybridize with said gene; and
  b) detecting the presence of a hybridization complex or of an amplification product as an indication of a bacterial resistance to virginiamycin mediated by the bacterial antibiotic resistance gene vga.

47. A method as defined in claim 1, which comprises the evaluation of the presence of a bacterial resistance to erythromycin mediated by the bacterial antibiotic resistance gene msrA directly from a test sample or from bacterial colonies, which comprises the steps of:
  a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 177 or a sequence complementary thereof under conditions such that the nucleic acid of said probe or primers can selectively hybridize with said gene; and
  b) detecting the presence of a hybridization complex or of an amplification product as an indication of a bacterial resistance to erythromycin mediated by the bacterial antibiotic resistance gene msrA.

48. A method as defined in claim 1, which comprises the evaluation of the presence of a bacterial resistance to β-lactams, aminoglycosides, chloramphenicol or trimethoprim mediated by the bacterial antibiotic resistance gene int directly from a test sample or from bacterial colonies, which comprises the steps of:
  a) contacting the bacterial DNA with a probe or with amplification primers, said probe or primers comprising at least one single stranded nucleic acid which nucleotidic sequence has at least twelve nucleotides in length capable of hybridizing with the nucleotide sequence defined in SEQ ID NO. 171 or a sequence complementary thereof under conditions such that the nucleic acid of said probe or primers can selectively hybridize with said gene; and
  b) detecting the presence of a hybridization complex or of an amplification product as an indication of a bacterial resistance to β-lactams, aminoglycosides, chloramphenicol or trimethoprim mediated by the bacterial antibiotic resistance gene int.

49. A method as defined in claim 1, which comprises the evaluation of the presence of a bacterial resistance to β-lactams, aminoglycosides, chloramphenicol or trimethoprim mediated by the bacterial antibiotic resistance gene sul directly from a test sample or from bacterial colonies, which comprises the steps of:
  a) contacting the bacterial DNA with a probe or withamplification primers, said probe or primers comprising at least one single stranded nucleic acid which nucleotidic sequence has at least twelve nucleotides in length capable of hybridizing with the nucleotide sequence defined in SEQ ID NO. 172 or a sequence complementary thereof under conditions such that the nucleic acid of said probe or primers can selectively hybridize with said gene; and
  b) detecting the presence of a hybridization complex or of an amplification product as an indication of a bacterial resistance to β-lactams, aminoglycosides, chloramphenicol or trimethoprim mediated by the bacterial antibiotic resistance gene sul.

50. A nucleic acid having the nucleotide sequence of any one of SEQ ID NO: 3, SEQ ID NO: 4, SEQ ID NO: 29, SEQ ID NO: 36, SEQ ID NO: 37, a part thereof and variants thereof which, when in single stranded form, ubiquitously and specifically hybridize with a target bacterial DNA as a probe or as a primer.

51. An oligonucleotide having a nucleotide sequence of any one of SEQ ID NOs: 38 to 43, SEQ ID NOs: 83 to 86, SEQ ID NO: 118, SEQ ID NO: 119, SEQ ID NO: 127, SEQ ID NO: 131, SEQ ID NO: 132, SEQ ID NOs: 141 to 153, SEQ ID NO: 158, SEQ ID NO: 159 and SEQ ID NO: 160.

52. A recombinant plasmid comprising a nucleic acid as defined in claim 51.

53. A recombinant host which has been transformed by a recombinant plasmid according to claim 52.

54. A recombinant host according to claim 53 wherein said host is *Escherichia coli*.

55. A diagnostic kit for the detection and/or quantification of the nucleic acids of any combination of the bacterial resistance genes defined in any one of claims 33 to 49 comprising any combination of probes or primers defined therein.

56. A diagnostic kit for the detection and/or quantification of nucleic acids of any bacterial species comprising the primers defined in SEQ ID NOs. 126 and 127.

57. A diagnostic kit for the simultaneous detection and/or quantification of nucleic acids of any bacterial antibiotic resistance genes selected from the group consisting of: $bla_{tem}$, $bla_{rob}$, $bla_{shv}$, aadB, aacC1, aacC2, aacC3, aacA4, mecA, vanA, vanH, vanX, satA, aacA-aphD, vat, vga, msrA, sul and int, and of any combination of the bacterial species defined in claim 1, comprising any combination of the bacterial probes defined in claim 1 and any combination of the probes to the antibiotic resistance genes defined in any one of SEQ ID NOs: 161 to 177 in whole or in part.

58. A diagnostic kit for the simultaneous detection and/or quantification of nucleic acids of any antibiotic resistance genes selected from the group consisting of: $bla_{tem}$, $bla_{rob}$, $bla_{shv}$, aadB, aacC1, aacC2, aacC3, aacA4, mecA, vanA, vanH, vanX, satA, aacA-aphD, vat, vga, msrA, sul and int, and of any combination of the bacterial species defined in claim 1, comprising any combination of the pairs of primers defined in claim 1 and any combination of pairs of primers that anneal to the antibiotic resistance genes defined in any one of SEQ ID NOs: 161 to 177.

59. A diagnostic kit for the simultaneous detection and/or quantification of any bacterial species, of any bacterial antibiotic resistance genes selected from the group consisting of: bla$_{tem}$, bla$_{rob}$, bla$_{shv}$, aadB, aacC1, aacC2, aacC3, aacA4, mecA, vanA, vanH, vanX, satA, aacA-aphD, vat, vga, msrA, sul and int, and of any combination of the bacterial species defined in claim 1, comprising any combination of pairs of primers defined in claim 1, a pair of universal primers and any combination of pairs of primers that anneal to the antibiotic resistance genes defined in any one of SEQ ID NOs.: 161 to 177.

60. The method of claim 1, wherein the probe for detecting nucleic acid sequences from said bacterial species has at least twelve nucleotides in length and is capable of hybridizing with any sequence selected from the group consisting of the following probes for the detection of the following species:

SEQ ID NO: 44, SEQ ID NO: 45, SEQ ID NO: 48, SEQ ID NO: 49, SEQ ID NO: 50, SEQ ID NO: 51, SEQ ID NO: 52, SEQ ID NO: 53, SEQ ID NO: 54, and a sequence complementary thereof for the detection of *Escherichia coli;*

SEQ ID NO: 70, SEQ ID NO: 71, SEQ ID NO: 72, SEQ ID NO: 73, SEQ ID NO: 76, SEQ ID NO: 77, SEQ ID NO: 80, SEQ ID NO: 81, SEQ ID NO: 82, and a sequence complementary thereof for the detection of *Proteus mirabilis;*

SEQ ID NO: 96, SEQ ID NO: 97, SEQ ID NO: 100, SEQ ID NO: 101, SEQ ID NO: 102, SEQ ID NO: 103, SEQ ID NO: 104, and a sequence complementary thereof for the detection of *Staphylococcus saprophyticus;*

SEQ ID NO: 108, SEQ ID NO: 109, SEQ ID NO: 110, SEQ ID NO: 111, SEQ ID NO: 114, SEQ ID NO: 115, SEQ ID NO: 116, SEQ ID NO: 117, and a sequence complementary thereof for the detection of *Moraxella catarrhalis;*

SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, and a sequence complementary thereof for the detection of *Pseudomonas aeruginosa;*

SEQ ID NO: 105, SEQ ID NO: 106, SEQ ID NO: 107, and a sequence complementary thereof for the detection of *Haemophilus influenzae;* and SEQ ID NO: 120, SEQ ID NO: 121, and a sequence complementary thereof for the detection of *Streptococcus pneumoniae.*

61. A method for the detection, identification or quantification of *Klebsiella pneumoniae* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Klebsiella pneumoniae* and capable of hybridizing with any one of SEQ ID NO. 8, SEQ ID NO. 9, SEQ ID NO. 10, SEQ ID NO. 11 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of *Klebsiella pneumoniae* in said test sample.

62. A method for detecting the presence or amount of *Klebsiella pneumoniae* in a test sample which comprises the following steps:

a) treating said sample with an aqueous solution containing at least one pair of oligonucleotide primers having at least twelve nucleotides in length, one of said primers being capable of hybridizing selectively with one of the two complementary strands of *Klebsiella pneumoniae* DNA and of any one of SEQ ID NO. 8, SEQ ID NO. 9, SEQ ID NO. 10, SEQ ID NO. 11, that contain a target sequence, and the other of said primers being capable of hybridizing with the other of said strands so as to form an extension product which contains the target sequence as a template;

b) synthesizing an extension product of each of said primers which extension product contains the target sequence, and amplifying said target sequence, if any, to a detectable level; and c) detecting the presence or amount of said amplified target sequence as an indication of the presence or amount of *Klebsiella pneumoniae* in said test sample.

63. The method of claim 62, wherein said at least one pair of primers is selected from the group consisting of:

a) SEQ ID NO: 61 and SEQ ID NO: 62,
b) SEQ ID NO: 67 and SEQ ID NO: 68,
c) SEQ ID NO: 135 and SEQ ID NO: 136, and
d) SEQ ID NO: 137 and SEQ ID NO: 138.

64. A method for the detection, identification or quantification of *Proteus mirabilis* directly from a test sample or from bacterial colonies, which comprises the following steps:

a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;

b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Proteus mirabilis* and capable of hybridizing with any one of SEQ ID NO. 12, SEQ ID NO. 13, SEQ ID NO. 14, SEQ ID NO. 15, and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of *Proteus mirabilis* in said test sample.

65. A method for detecting the presence or amount of *Proteus mirabilis* in a test sample which comprises the following steps:
   a) treating said sample with an aqueous solution containing at least one pair of oligonucleotide primers having at least twelve nucleotides in length, one of said primers being capable of hybridizing selectively with one of the two complementary strands of *Proteus mirabilis* DNA and of any one of SEQ ID NO. 12, SEQ ID NO. 13, SEQ ID NO. 14, SEQ ID NO. 15, that contain a target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of *Proteus mirabilis* in said test sample.

66. The method of claim 65, wherein said at least one pair of primers is selected from the group consisting of:
   a) SEQ ID NO: 74 and SEQ ID NO: 75, and
   b) SEQ ID NO: 133 and SEQ ID NO: 134.

67. A method for the detection, identification or quantification of *Staphylococcus saprophyticus* directly from a test sample or from bacterial colonies, which comprises the following steps:
   a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Staphylococcus saprophyticus* and capable of hybridizing with any one of SEQ ID NO. 21, SEQ ID NO. 22, SEQ ID NO. 23, SEQ ID NO. 24 and a sequence complementary thereof, under conditions such that the nucleic acid of said probe can selectively hybridize with said bacterial DNA, whereby a hybridization complex is formed, and
   c) detecting the presence of said hybridization complex on said inert support or in said solution as an indication of the presence or amount of *Staphylococcus saprophyticus* in said test sample.

68. A method for detecting the presence or amount of *Staphylococcus saprophyticus* in a test sample which comprises the following steps:
   a) treating said sample with an aqueous solution containing at least one pair of oligonucleotide primers having at least twelve nucleotides in length, one of said primers being capable of hybridizing selectively with one of the two complementary strands of *Staphylococcus saprophyticus* DNA and of any one of SEQ ID NO. 21, SEQ ID NO. 22, SEQ ID NO. 23, SEQ ID NO. 24, that contain a target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of *Staphylococcus saprophyticus* in said test sample.

69. The method of claim 68, wherein said at least one pair of primers is selected from the group consisting of:
   a) SEQ ID NO: 98 and SEQ ID NO: 99, and
   b) SEQ ID NO: 139 and SEQ ID NO: 140.

70. A method for the detection, identification or quantification of *Haemophilus influenzae* directly from a test sample or from bacterial colonies, which comprises the following steps:
   a) depositing and fixing on an inert support or leaving in solution the bacterial DNA of the sample or of the bacterial colonies isolated from the sample or inoculating said sample or said bacterial colonies on an inert support and lysing in situ said inoculated sample or bacterial colonies to release the bacterial DNA, said bacterial DNA being made in a substantially single stranded form;
   b) contacting said single stranded DNA with a probe, said probe comprising at least one single stranded nucleic acid which nucleotide sequence has at least twelve nucleotides in length and is capable of specifically and ubiquitously hybridizing with DNA from strains or representatives of *Haemophilus influenzae* and capable of hybridizing with any one of SEQ ID NO. 25, SEQ ID NO. 26, SEQ ID NO. 27 and a sequence complementary thereof, under conditions such that the nucleic acid of said probe can selectively hybridize with said bacterial DNA, whereby a hybridization complex is formed, and
   c) detecting the presence of said hybridization complex on said inert support or in said solution as an indication of the presence or amount of *Haemophilus influenzae* in said test sample.

71. A method for detecting the presence or amount of *Haemophilus influenzae* in a test sample which comprises the following steps:
   a) treating said sample with an aqueous solution containing at least one pair of oligonucleotide primers having at least twelve nucleotides in length, one of said primers being capable of hybridizing selectively with one of the two complementary strands of *Haemophilus influenzae* DNA and of any one of SEQ ID NO. 25, SEQ ID NO. 26, SEQ ID NO. 27, that contain a target sequence, and the other of said primers being capable of hybridizing with the other of said strands so as to form an extension product which contains the target sequence as a template;
   b) synthesizing an extension product of each of said primers which extension product contains the target sequence, and amplifying said target sequence, if any, to a detectable level; and
   c) detecting the presence or amount of said amplified target sequence as an indication of the presence or amount of *Haemophilus influenzae* in said test sample.

72. The method of claim 71, wherein said at least one pair of primers comprises the following pair: SEQ ID NO: 154 and SEQ ID NO: 155.

73. A method for the detection of the presence or amount of any bacterial species directly from a test sample or from bacterial colonies, which comprises the following steps:

a) depositing and fixing on an inert support or leaving in solution the bacterial DNA of the sample or of the bacterial colonies isolated from this sample, or inoculating said sample or said bacterial colonies on an inert support, and lysing in situ said inoculated sample or to release the bacterial DNA, said bacterial DNA being in a substantially single stranded form;

b) contacting said single stranded DNA with a universal probe which sequence is selected from the group consisting of SEQ ID NO: 122, SEQ ID NO: 123, SEQ ID NO: 124, SEQ ID NO: 125, SEQ ID NO: 128, SEQ ID NO: 129, SEQ ID NO: 130 and a sequence complementary thereof, under conditions such that the nucleic acid of said probe can selectively hybridize with said bacterial DNA, whereby a hybridization complex is formed, and c) detecting the presence of said hybridization complex on said inert support or in said solution as an indication of the presence or amount of said any bacterial species in said test sample.

74. A method as defined in claim 26, wherein said bacterial species is *Streptococcus pyogenes* and said probe further comprises at least one single stranded nucleic acid which nucleotide sequence is capable of specifically and ubiquitously hybridizing with DNA from strains or representatives of *Streptococcus pyogenes* and with any one of SEQ ID NO. 32 and a complementary sequence thereof, whereby *Streptococcus pyogenes* and associated exotoxin A speA gene are both detectable.

75. A method as defined in claim 27, wherein said bacterial species is *Streptococcus pyogenes* and said at least one pair of primers further comprises at least one pair of primers having at least twelve nucleotides in length and being capable of hybridizing with any one of SEQ ID NO. 32 and a sequence complementary thereof, whereby *Streptococcus pyogenes* and associated exotoxin A speA gene are both detectable.

76. The method as defined in claim 27, wherein said at least one pair of primers further comprises SEQ ID NO: 141 and SEQ ID NO: 142 specific and ubiquitous for *Streptococcus pyogenes*, whereby *Streptococcus pyogenes* and associated exotoxin A speA gene are both detectable.

77. A diagnostic kit for the detection and/or quantification of the nucleic acids of any combination of the bacterial species defined in any one of claims 8, 11, 14, 17, 20, 23, 26, 29, 60, 61, 64, 67 and 70, comprising any combination of probes defined therein.

78. A diagnostic kit for the detection or quantification of the nucleic acids of any combination of the bacterial species defined in any one of claims 9, 10, 12, 13, 15, 16, 18, 19, 21, 22, 24, 25, 27, 28, 30, 31, 62, 63, 65, 66, 68, 69, 71, 72, 74 and 75 comprising any combination of pairs of primers defined therein.

* * * * *